US012697402B2

(12) United States Patent
Wang et al.

(10) Patent No.: US 12,697,402 B2
(45) Date of Patent: Aug. 4, 2026

(54) DETECTION OF COLONIC NEOPLASIA IN VIVO USING NEAR-INFRARED PEPTIDE TARGETED AGAINST OVEREXPRESSED cMET

(71) Applicant: THE REGENTS OF THE UNIVERSITY OF MICHIGAN, Ann Arbor, MI (US)

(72) Inventors: Thomas D. Wang, Ann Arbor, MI (US); Juan Zhou, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1353 days.

(21) Appl. No.: 17/432,070

(22) PCT Filed: Feb. 21, 2020

(86) PCT No.: PCT/US2020/019229
§ 371 (c)(1),
(2) Date: Aug. 18, 2021

(87) PCT Pub. No.: WO2020/172535
PCT Pub. Date: Aug. 27, 2020

(65) Prior Publication Data
US 2022/0193271 A1      Jun. 23, 2022

Related U.S. Application Data

(60) Provisional application No. 62/808,637, filed on Feb. 21, 2019.

(51) Int. Cl.
*C07K 7/06* (2006.01)
*A61K 49/00* (2006.01)

(52) U.S. Cl.
CPC ...... *A61K 49/0056* (2013.01); *A61K 49/0032* (2013.01); *A61K 49/0043* (2013.01); *C07K 7/06* (2013.01)

(58) Field of Classification Search
None
See application file for complete search history.

(56) References Cited

U.S. PATENT DOCUMENTS

| | | | | |
|---|---|---|---|---|
| 6,919,426 | B2 * | 7/2005 | Boone | A61P 13/00 |
| | | | | 424/178.1 |
| 2005/0227301 | A1 | 10/2005 | Glover et al. | |
| 2010/0061929 | A1 | 3/2010 | Wang et al. | |
| 2012/0219505 | A1 | 8/2012 | Wang et al. | |
| 2014/0127139 | A1 | 5/2014 | Ballet et al. | |
| 2015/0038672 | A1 | 2/2015 | Schmitthenner et al. | |
| 2015/0056209 | A1 * | 2/2015 | Witztum | C07K 7/08 |
| | | | | 424/139.1 |
| 2015/0216398 | A1 | 8/2015 | Yang et al. | |

FOREIGN PATENT DOCUMENTS

| | | |
|---|---|---|
| CN | 107073065 A | 8/2017 |
| WO | WO-2016/029125 A1 | 2/2016 |

OTHER PUBLICATIONS

Alencar et al., Colonic Adenocarcinomas: Near-Infrared Microcatheter Imaging of Smart Probes for Early Detection—Study in Mice, Radiology 244:232-238 (2007).
Bardelli et al., "Amplification of the MET Receptor Drives Resistance to Anti-EGFR Therapies in Colorectal Cancer," Cancer Discov 3:658-673 (2013).
Birchmeier et al., "Met, Metastasis, Motility and More," Nat Rev Mol Cell Biol 4:915-925 (2003).
Boccaccio et al., "MET-Mediated Resistance to EGFR Inhibitors: an Old Liaison Rooted in Colorectal Cancer Stem Cells," Cancer Res 74:3647-3651 (2014).
Brown et al, "Risk factors and operative mortality in surgery for colorectal cancer," Ann R Coll Surg Engl 73:269-272 (1991).
Burggraaf et al., "Detection of colorectal polyps in humans using an intravenously administered fluorescent peptide targeted against cMet," Nat Med 21:955-961 (2015).
Carraro et al., "Obstructing Colonic Cancer: Failure and Survival Patterns Over a Ten-Year Follow-Up After One-Stage Curative Surgery," Dis Colon Rectum 44:243-250 (2001).
Chen et al., "Design and Development of Molecular Imaging Probes," Curr Top Med Chem 10:1227-1236 (2010).
Chen et al., "Multiplexed Targeting of Barrettis Neoplasia with a Heterobivalent Ligand: Imaging Study on Mouse Xenograft in Vivo and Human Specimens ex Vivo," J Med Chem 61:5323-5331 (2018).
Christensen et al., "cMet as a target for human cancer and characterization of inhibitors for therapeutic intervention," Cancer Lett 225:1-26 (2005).
Clapper et al., "Detection of Colorectal Adenomas Using a Bioactivatable Probe Specific for Matrix Metalloproteinase Activity," Neoplasia 13:685-691 (2011).
Cwirla et al., "Peptides on phage: A vast library of peptides for identifying ligands," Proc. Natl. Acad. Sci., 83:6378-6382 (1990).
Dame et al., "Identification, isolation and characterization of human LGR5-positive colon adenoma cells," Development 145, 16 pages (2018).
Di Renzo et al., "Overexpression and Amplification of the Met/HGF Receptor Gene during the Progression of Colorectal Cancer," Clin Cancer Res 1:147-154 (1995).
Essler et al., "Molecular specializatin of breast vasculature: A breast-homing phage-displayed peptide binds to aminopeptidase P in breast vasculature," Proc. Natl. Acad. Sci. USA, 99:2252-2257 (2002).
Farrar et al., "Colorectal Cancers Found After a Complete Colonoscopy," Clin. Gastroenterol. Hepatol. 4:1259-1264 (2006).
Favoriti et al., "Worldwide burden of colorectal cancer: a review," Updates Surg 68:7-11 (2016).

(Continued)

*Primary Examiner* — Noble E Jarrell
(74) *Attorney, Agent, or Firm* — MARSHALL, GERSTEIN & BORUN LLP

(57) ABSTRACT

The disclosure provides peptides, including labeled peptides, that selectively bind to the cMet protein. The disclosure also provides methods of detecting dysplastic cells and tissue, e.g., in the colon, providing early identification of precancerous and cancerous tissue.

1 Claim, 28 Drawing Sheets

Specification includes a Sequence Listing.

(56)        References Cited

OTHER PUBLICATIONS

Fearon et al., "A Genetic Model for Colorectal Tumorigenesis," Cell 61:759-767 (1990).

Ferlay et al., "Cancer incidence and mortality worldwide: sources, methods and major patterns in GLOBOCAN 2012," Int J Cancer 136:E359-386 (2015).

Ferlay et al., "Estimates of worldwide burden of cancer in 2008: GLOBOCAN 2008," Int. J. Cancer 127:2893-2917 (2010).

Fields et al., "Solid phase peptide synthesis utilizing 9-fluorenylmethoxycarbonyl amino acids," Int J Pept Protein Res 35:161-214 (1990).

Hay et al., "Nuclear Imaging of Met-Expressing Human and Canine Cancer Xenografts with Radiolabeled Monoclonal Antibodies (MetSeek)," Clin Cancer Res 11:7064s-7069s (2005).

Heresbach et al., "Miss rate for colorectal neoplastic polyps: a prospective multicenter study of back-to-back video colonoscopies," Endoscopy 40:284-290 (2008).

Hinoi et al., "Mouse Model of Colonic Adenoma-Carcinoma Progression Based on Somatic Apc Inactivation," Cancer Res 67:9721-9730 (2007).

Hsiung et al., "Detection of colonic dysplasia in vivo using a targeted heptapeptide and confocal microendoscopy," Nat Med 14:454-458 (2008).

Hung et al., "Development of a mouse mode for sporadic and metastatic colon tumors and its use in assessing drug treatment," Proc. Natl. Acad. Sci. USA, 107:1565-1570 (2010).

International Search Report and Written Opinion from International Application No. PCT/US20/19229 mailed Jul. 2, 2020.

Ishikawa et al., "Development of functional human blood and immune systems in NOD/SCID/IL2 receptor $\gamma$ chain$^{null}$ mice," Blood 106:1565-1573 (2005).

Jagoda et al., "Immuno-PET of the Hepatocyte Growth Factor Receptor Met Using the 1-Armed Antibody Onartuzumab," J Nucl Med 53:1592-1600 (2012).

Joshi et al., "Design and Synthesis of Near-Infrared Peptide for in Vivo Molecular Imaging of HER2," Bioconjug Chem 27:481-494 (2016).

Joshi et al., "Detection of Sessile Serrated Adenomas in the Proximal Colon Using Wide-Field Fluorescence Endoscopy," Gastroenterology 152:1002-1013 (2017).

Joshi et al., "Detection of Sessile Serrated Adenomas in the Proximal Colon Using Wide-Field Fluorescence Endoscopy," Gastroenterology 152:1002-1013 e1009 (2017).

Joshi et al., "Multimodal endoscope can quantify wide-field fluorescence detection of Barrettis neoplasia," Endoscopy 48:A1-A13 (2016).

Joshi et al., "Near-infrared-labeled peptide multimer functions as phage mimic for high affinity, specific targeting of colonic adenomas in vivo (with videos)," Gastrointest Endosc 76:1197-1206 (2012).

Joyce et al., "Stage-specific vascular markers revealed by phage display in a mouse model of pancreatic islet tumorigenesis," Cancer Cell, 4:393-403 (2003).

Kaminski et al., "Advanced imaging for detection and differentiation of colorectal neoplasia: European Society of Gastrointestinal Endoscopy (ESGE) Guideline," Endoscopy 46:435-449 (2014).

Lee et al., "Peptides and Peptide Hormones for Molecular Imaging and Disease Diagnosis," Chem Rev 110:3087-3111 (2010).

Lee et al., "Targeting Bladder Tumor Cells In vivo and in the Urine with a Peptide Identified by Phage Display," Mol. Cancer Res., 5(1):11-19 (2007).

Li et al., "Affinity Peptide for Targeted Detection of Dysplasia in Barrett's Esophagus," Gastroenterology 139:1472-80 (2010).

Liu et al., "In vivo targeting of colonic dysplasia on fluorescence endoscopy with near-infrared octapeptide," Gut 62:395-403 (2013).

Lu et al., "Single chain anti-cMet antibody conjugated nanoparticles for in vivo tumor-targeted imaging and drug delivery," Biomaterials 32:3265-3274 (2011).

Ludtke et al., "In Vivo Selection and Validation of Liver-Specific Ligands Using a New T7 Phage Peptide Display System," Drug Deliv., 14:357-369 (2007).

Marten et al., "Detection of Dysplastic Intestinal Adenomas Using Enzyme-Sensing Molecular Beacons in Mice," Gastroenterology 122:406-414 (2002).

Matsumura et al., "HGF regulates VEGF expression via the cMet receptor downstream pathways, PI3K/Akt, MAPK and STAT3, in CT26 murine cells," Int J Oncol 42:535-542 (2013).

Maulik et al., "Role of the hepatocyte growth factor receptor, cMet, in oncogenesis and potential for therapeutic inhibition," Cytokine Growth Factor Rev 13:41-59 (2002).

Miyoshi et al., "In vitro expansion and genetic modification of gastrointestinal stem cells in spheroid culture," Nat Protoc 8:2471-2482 (2013).

Naran et al., "Inhibition of HGF/MET as therapy for malignancy," Expert Opin Ther Targets 13:569-581 (2009).

Pasqualini et al., "Organ targeting in vivo using phage display peptide libraries," Nature, 380:364-366 (1996).

Paul et al., "Analyzing protein-protein interactions by quantitative mass spectrometry," Methods 54:387-395 (2011).

Rex, ". Reducing costs of colon polyp management," Lancet Oncol 10:1135-1136 (2009).

Robertson et al., "Colorectal cancers soon after colonoscopy: a pooled multicohort analysis," Gut 63:949-956 (2014).

Sanduleanu et al., "Interval cancers after colonoscopy—insights and recommendations," Nat. Rev. Gastroenterol. Hepatol. 9:550-554 (2012).

Sato et al., "Long-term Expansion of Epithelial Organoids From Human Colon, Adenoma, Adenocarcinoma, and Barrettis Epithelium," Gastroenterology 141:1762-1772 (2011).

Sato et al., "Single Lgr5 stem cells build crypt-villus structures in vitro without a mesenchymal niche," Nature 459:262-265 (2009).

Sattler et al, "c-Met and Hepatocyte Growth Factor: Potential as Novel Targets in Cancer Therapy," Curr Oncol Rep 9:102-108 (2007).

Scott et al., "Searching for Peptide Ligands with an Epitope Library," Science, 249:386-390 (1990).

Shultz ete al., "Human Lymphoid and Myeloid Cell Development in NOD/LtSz-scid IL2R$\gamma^{null}$ Mice Engrafted with Mobilized Human Hemopoietic Stem Cells," J Immunol 174:6477-6489 (2005).

Soetikno et al., "Prevalence of Nonpolyploid (Flat and Depressed) Colorectal Neoplasms in Asymptomatic and Symptomatic Adults," Jama 299(9):1027-1035 (2008).

Song et al., "Potent antitumor activity of cabozantinib, a cMet and VEGFR2 inhibitor, in a colorectal cancer patient-derived tumor explant model," Int J Cancer 136:1967-1975 (2015).

Stoffel et al., "Chromoendoscopy Detects More Adenomas than Colonoscopy Using Intensive Inspection without Dye Spraying," Cancer Prev Res 1:507-513 (2008).

Sturm et al., "Targeted Imaging of Esophageal Neoplasia with a Fluorescently Labeled Peptide: First-in-Human Results," Sci Transl Med 5(184):184ra161, 10 pages (2013).

Su et al., "Multiple Intestinal Neoplasia Caused by a Mutation in the Murine Homolog of the APC Gene," Science 256:668-670 (1992).

Sugimoto et al., "Reconstruction of the Human Colon Epithelium In Vivo," Cell Stem Cell 22:171-176 (2018).

Thomas et al., "In vitro binding evaluation of $^{177}$Lu-AMBA, a novel $^{177}$Lu-labeled GRP-R agonist for systemic radiotherapy in human tissues," Clin Exp Metastasis 26:105-119 (2009).

Torre et al., "Global Cancer Statistics, 2012" CA Cancer J Clin 65:87-108 (2015).

Towner et al., "In vivo detection of c-Met expression in a rat C6 glioma model," J Cell Mol Med 12(1):174-186 (2008).

Tsai et al., "A Method for Cryogenic Preservation of Human Biopsy Specimens and Subsequent Organoid Culture," Cell Mol Gastroenterol Hepatol 6(2):218-222 (2018).

Uehara et al., "Placental defect and embryonic lethality in mice lacking hepatocyte growth factor/scatter factor," Nature 373:702-705 (1995).

Van Rijn eet al., "Polyp Miss Rate Determined by Tandem Colonoscopy: A Systematic Review," Am J Gastroenterol 101:343-350 (2006).

(56)        References Cited

OTHER PUBLICATIONS

Wang et al., "In vivo identification of colonic dysplasia using fluorescence endoscopic imaging," Gastrointestinal Endoscopy 49(4):447-55 (1999).

Winawer et al., "Prevention of Colorectal Cancer by Colonoscopic Polypectomy," N Engl J Med 329(27):1977-1981 (1993).

Winawer et al., "Randomized Comparison of Surveillance Intervals After Colonoscopic Removal of Newly Diagnosed Adenomatous Polyps," N Engl J Med 328(13):901-906 (1993).

Xue et al., "Iron Uptake via DMT1 Integrates Cell Cycle with JAK-STAT3 Signaling to Promote Colorectal Tumorigenesis," Cell Metab 24:447-461 (2016).

You et al., "Biopanning and Characterization of Peptides with Fe3O4 Nanoparticles-Binding Capability Via Phage Display Random Peptide Library Technique," Colloids Surf B Biointerfaces, pp. 537-545, Abstract (2016).

Yui et al., "Functional engraftment of colon epithelium expanded in vitro from a single adult Lgr5+ stem cell," Nat Med 18:618-623 (2012).

Zhou et al., "EGFR Overexpressed in Colonic Neoplasia Can be Detected on Wide-Field Endoscopic Imaging," Clin Transl Gastroenterol 6:e101, 11 pages (2015).

You et al., Selectively tumor targeted Fe3O4 magnetic nanoparticles modified with peptide, Mat. Sci., 5: 111-118, (2018).

Li et al., Novel bi-functional 14-mer peptides with both ovarian carcnimoa cells targeting and magnetic Fe3O4 nanoparticles affinity, Mat., 12(5): 755, (2019).

Wu et al., Detection of colonic neoplasia in vivo using near-infrared-labeled peptide targeting cMet, Sci. Rep., 9: 17917, (2019).

* cited by examiner

A

Cy5.5

QQTNWSL

GGGSK

B

Cy5.5

TLQWNQS

GGGSK

Figure 1
(to be continued)

(continuation)

(to be continued)

(continuation)

(to be continued)

(continuation)

A.

B.

C.

(to be continued)

(continuation)

(to be continued)

(continuation)

(to be continued)

(continuation)

(to be continued)

(continuation)

(to be continued)

(continuation)

(to be continued)

(continuation)

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1

Gln Gln Thr Asn Trp Ser Leu
1               5

<210> SEQ ID NO 2
<211> LENGTH: 5
<212> TYPE: PRT
<213> ORGANISM: Artificial Seuqence
<220> FEATURE:
```

-continued

```
<223> OTHER INFORMATION: Synthetic Linker

<400> SEQUENCE: 2

Gly Gly Gly Ser Lys
1               5

<210> SEQ ID NO 3
<211> LENGTH: 7
<212> TYPE: PRT
<213> ORGANISM: Artificial Seuqence
<220> FEATURE:
<223> OTHER INFORMATION: Synthetic Polypeptide

<400> SEQUENCE: 3

Thr Leu Gln Trp Asn Gln Ser
1               5
```

DETECTION OF COLONIC NEOPLASIA IN VIVO USING NEAR-INFRARED PEPTIDE TARGETED AGAINST OVEREXPRESSED cMET

CROSS-REFERENCE TO RELATED APPLICATIONS

This application claims priority to Provisional U.S. Patent Application No. 62/808,637, filed Feb. 21, 2019, which is hereby incorporated by reference in its entirety.

STATEMENT OF GOVERNMENT INTEREST

This invention was made with government support under CA193377 awarded by the National Institutes of Health. The government has certain rights in the invention.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "53791A_Seglisting.txt", which was created on Feb. 13, 2020 and is 828 bytes in size. The subject matter of the Sequence Listing is incorporated herein in its entirety by reference.

FIELD

The disclosure is directed to peptide reagents, methods for detecting colon pre-cancer (dysplasia) or cancer using the peptide reagents, and methods for targeting dysplastic or cancerous colon cells using the peptide reagents.

BACKGROUND

Colorectal cancer (CRC) is the third most commonly diagnosed cancer, and the fourth cause of oncological death worldwide. It accounts for about 8% of all cancer deaths, with an estimated 693,900 deaths occurred in 2012[1-4]. Most patients have developed an advanced stage of CRC when showing obvious syndrome-like obstruction or intestinal bleeding, consistent with the high mortality rate and poor survival of CRC patients[5,6]. Finding CRC at an early stage, when it is still small and hasn't spread, is crucial to reduce mortality. Currently, widely used standard white light endoscopy for CRC screening frequently misses premalignant dysplasia, which is small, flat and has a patchy shape[7,8]. The rates of missed polyps and adenomas were as high as 28% and 20%, respectively[9]. Moreover, some invisible flat lesions can be even more aggressive than visible polyps, and are more likely to contain carcinoma than polyps[10]. The rates of missed smaller and flat lesions is as high as 25%[11]. Finding invisible polyps and flat lesions efficiently is a current problem for early cancer detection. Also, interval cancers occur when CRC arises within 5 years after a colonoscopy exam, and are increasing in incidence (Farrar et al., Clin. Gastroenterol. Hepatol. 4:1259-1264 (2006), Sanduleanu et al., Nat. Rev. Gastroenterol. Hepatol. 9:550-554 (2012), Robertson, Gut 63:949-956 (2014)).

Methods of advanced imaging are being developed to improve performance for early CRC detection. Chromoendoscopy uses topically administered intravital dyes and narrow band imaging (NBI) uses filtered light in different spectral bands to highlight mucosal changes suspicious for disease (Stoffel, Cancer Prev Res 1:507-513 (2008), Kaminski, Endoscopy 46:435-449 (2014)). In these approaches, contrast is generated from non-specific mechanisms that are unrelated to the biological processes that drive CRC progression, and have shown limited effectiveness in clinical studies.

Pre-clinical mouse models of disease provide an important ool for studying mechanisms of disease development. It has been established that mutations in the adenomatous polyposis coli (APC) gene are likely to be critical events in the initiation of the majority of adenomas and CRC. Previously reported genetically engineered mouse models that mimic human APC gene mutations mainly develop adenomas in the small intestine (e.g., APCM in model[56], not the distal colon, making it difficult to image the polyps and their progression in vivo using currently available small animal endoscopy tools. Hinoi et al.[57], describes genetically engineered mice (termed CPC:Apc mice) in which a somatic mutation in an Apc allele leads to a truncated Apc protein and causes the development of adenomas in the distal colon as early as 10 weeks. Others have developed mouse models that grow tumors in the distal colon using implantation of cancerous cells[58] or adenovirus activated mutations[59] and report binding of cathepsin B smart probes, but surgical intervention was needed to generate polyps and the ensuing response to injury may have resulted in target alteration.

Colonoscopy has been widely accepted by physicians for decades as a procedure useful in detecting and removing polyps. Small and flat colorectal lesions, however, are difficult to visualize by traditional white-light (WL) endoscopy. To improve the ability of endoscopy to detect and characterize colorectal lesions, a variety of endoscopic imaging techniques have been developed. Combination of molecular targeted fluorescence reagents and wide-field techniques have shown encouraging results in detecting precancerous lesions in CRC. Studies have identified several clinical and pathological biomarkers that are associated with the prognosis of CRC. As a tyrosine kinase receptor, cMet (mesenchymal-epithelial transition factor), activated by hepatocyte growth factor, regulates multiple biological processes, such as cell proliferation, scattering and survival.

As a member of proto-oncogenic transmembrane tyrosine kinases, cMet is widely expressed in epithelial and endothelial cells[14]. cMet is expressed on the surface of normal epithelial cells in the digestive tract and is highly overexpressed in CRC. The 190 kD cMet heterodimer consists of two subunits linked by disulfide bonds, including an extracellular 50 kD α-chain and a transmembrane 145 kD β-chain. The binding of cMet to its ligand, i.e., hepatocyte growth factor (HGF), triggers cMet dimerization and autophosphorylation, which in turn phosphorylates and activates downstream mitogen-activated protein kinase (MAPK), phosphatidylinositol 3-kinase (PI3K), and signal transducer and activator of transcription (STAT) signaling pathways[15]. This pathway plays an important role in tumor growth, invasion, angiogenesis, and metastasis[16]. cMet is essential for cell proliferation, mitogenesis, morphogenesis, and angiogenesis[16]. Elevated levels of cMet have been detected in a number of cancers, such as colorectal, pancreatic, gastric, hepatocellular, and breast cancers, as well as many sarcomas[17-19], making cMet an important target for antineoplastic therapies.

Endoscopic imaging with use of exogenous fluorescent-labeled probes can yield imaging results that provide precise localization of neoplastic lesions, and fluorescence provides improved contrast. To date, diagnostic molecules that have been used as targeting agents include antibodies and antibody fragments to detect pre-malignant and malignant lesions in various types of cancer. The use of antibodies and antibody fragments is limited, however, by immunogenicity, cost of production and long plasma half-life. Small molecules, RNA aptamers, and activatable probes have also been used. Peptides represent a newer class of imaging agent that is compatible with clinical use in the digestive tract, in particular with topical administration. Some monoclonal antibodies have been developed as fluorescent imaging agents targeting cMet[22,23]. As noted, such agents have a relatively high molecular weight and large size, which limits their ability to penetrate tissue, increases their immunogenicity, and reduces their circulatory half-life.

Phage display is a powerful combinatorial technique for peptide discovery that uses methods of recombinant DNA technology to generate a complex library of peptides, often expressing up to $10^7$-$10^9$ unique sequences that can bind to cell surface antigens. The DNA of candidate phages can be recovered and sequenced, elucidating positive binding peptides that can then be synthetically fabricated. Phage display identified peptide binders to high grade dysplasia in Barrett's esophagus[60] and human colonic dysplasia[61] using the commercially available NEB M13 phage system. The T7 system has proven effective in in vivo panning experiments identifying peptides specific to pancreatic islet vasculature[62], breast vasculature[63], bladder tumor cells[64], and liver tissue[65]. Panning with intact tissue presents additional relevant cell targets while accounting for subtle features in the tissue microenvironment that may affect binding.

Recent advances in in vitro organoid culture technologies have opened a new window onto the development of novel models for human cancer research. Lgr5+ stem cell-derived 'mini-gut' organoids phenocopy the epithelium of intestinal crypts and villi[30] showing that organoids can display self-organizing capacities, phenocopying essential aspects of the organs from which they are derived. Organoids can be derived from healthy and tumor tissues, and advances in efficient organoid orthotopic xenotransplant methods[31] enable the development of more physiological preclinical cancer models for early cancer detection.

Therefore, a need continues to exist in the art for improved animal models for CRC and new products and methods for early detection of dysplasia. New products and methods for early detection would have important clinical applications for increasing the survival rate for CRC and reducing healthcare costs.

SUMMARY

Transformed cells and tissues express molecular changes well in advance of gross morphological changes, thus providing an opportunity for the early detection of cancer. Peptides that bind to pre-cancerous colorectal lesions have the potential to guide tissue biopsy for lesions that are endoscopically "invisible," and such peptides can be identified and isolated using combinatorial phage display screening. Peptides have in vivo advantages in the gastrointestinal tract because they can be delivered topically to identify early molecular changes on the surface of epithelial cells located on the most superficial layer of mucosa where cancer originates. In addition, they can exhibit rapid binding kinetics and also diffuse into diseased mucosa. Further, smaller peptides reduce the opportunity for non-specific interactions, thereby reducing the background problem found with larger targeting molecules such as proteins (e.g., antibodies), antibody fragments, and even peptides on the order of about 25 or more amino acids. The relatively small, i.e., no larger than 20 amino acids, peptides are smaller in size and lower in molecular weight than these other targeting molecules. These properties help overcome many challenges for probe delivery, including irregular microvasculature, heterogeneous uptake, and transport barriers. Improved diffusion and extravasation through leaky vessels also can result in higher concentrations and deeper penetration of the relatively small peptides of the disclosure, relative to these other targeting molecules. Also, the peptides of the disclosure have a relatively low potential for immunogenicity. The peptides of the disclosure are also suitable for administration to humans by a number of routes including intra-rectal delivery and, preferably, intravenous delivery.

Disclosed herein are data establishing the capability of cMet-targeted peptides, such as the cMet-targeted peptide QQTNWSL (SEQ ID NO:1), to detect premalignant colonic lesions in vivo in a patient-derived organoid mouse model. In some exemplified embodiments, the cMet-targeted peptide QQTNWSL (SEQ ID NO:1) is attached to a linker such as the GGGSK linker of SEQ ID NO:2, in turn attached to, and thereby labeled with, the fluorophore Cy5.5 (hereafter, QQT*-Cy5.5). The data support the disclosure of such peptides, including the QQT*-Cy5.5 peptide, as agents capable of detecting precancerous dysplasia in an efficient and convenient manner.

A combination of a molecular imaging tool with a fluorescent peptide targeting cMet, which is overexpressed in premalignant CRC dysplasia, is expected to enhance diagnostic efficacy. Disclosed herein is a 7-amino-acid peptide conjugated to near-infrared (NIR) fluorescent cyanine dye that specifically binds to cMet. The binding to cMet was shown with cMet high/low expressed cell lines in vitro and the specificity of this peptide for cMet was validated in knockdown and competition studies. The disclosed peptide exhibits a high binding affinity of 57 nM and the time constant is 1.6 min, which support rapid binding with topical administration. This peptide is also shown to bind to human adenoma/SSA organoid and to spontaneous colonic adenomas that express high levels of cMet in vivo. Specific uptake in human adenoma/SSA organoid and spontaneous adenomas shows feasibility for real-time in vivo imaging with this peptide. Immunofluorescence studies of human proximal colon specimens further demonstrated the peptide can be used endoscopically to detect premalignant lesions and to guide tissue biopsy.

As an exemplary targeting peptide for colonic dysplasia according to the disclosure, the QQT*-Cy5.5 peptide is a short amino-acid protein fragment that functions as a targeting ligand that is highly specific for cMet, a cell surface target that plays a key role in many biological processes. Peptides are promising for clinical translation to detect imaging biomarkers upregulated in colorectal and other cancers. They are intrinsically high in diversity, and can be designed to bind to a broad range of cell surface targets with high specificity and affinity on the nanomolar scale. With topical application, peptides can be delivered effectively to mucosal surfaces in the digestive tract with high concentrations to maximize target interactions and achieve rapid binding with minimal risk for toxicity. This probe platform has flexibility to be labeled with a broad range of fluorophores for multiplexed imaging, and is inexpensive to mass manufacture. Peptides also have low potential for immunogenicity that allows for repeat use. These features of peptides are well suited for clinical use in high volume procedures, such as colonoscopy.

In one aspect, the disclosure provides a peptide comprising the amino acid sequence set forth in SEQ ID NO:1. In some embodiments, the peptide is derivatized, such as by attachment to a linker. In some embodiments, the linker comprises the sequence set forth in SEQ ID NO:2 (GGGSK). In some embodiments, the derivatized peptide is labeled, such as with a fluorescent label. In some embodiments, the label is FITC, Cy5.5, Cy 7, Li-Cor, a radiolabel, biotin, luciferase, 1,8-ANS (1-Anilinonaphthalene-8-sulfonic acid), 1-Anilinonaphthalene-8-sulfonic acid (1,8-ANS), 5-(and-6)-Carboxy-2', 7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-iso-thiocyanate pH 9.0, eYFP (Enhanced Yellow Fluorescent Protein), FDA, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, Fura-2, GFP (S65T), HcRed, Indo-1 Ca2+, Indo-1, Ca free, Indo-1, Ca saturated, JC-1, JC-1 pH 8.2, Lissamine rhodamine, Lucifer Yellow, CH, Magnesium Green, Magnesium Green Mg2+, Magnesium Orange, Marina Blue, mBanana, mCherry, mHoneydew, mOrange, mPlum, mRFP, mStrawberry, mTangerine, NBD-X, NBD-X, MeOH, NeuroTrace 500/525, green fluorescent Nissl stain-RNA, Nile Blue, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 7.0, Rhodol Green antibody conjugate pH 8.0, Sapphire, SBFI-Na+, Sodium Green Na+, Sulforhodamine 101, Tetramethylrhodamine antibody conjugate pH 8.0, Tetramethylrhodamine dextran pH 7.0, Texas Red-X antibody conjugate pH 7.2, $^{11}$C, $^{13}$N, $^{15}$O, $^{18}$F, $^{32}$P, $^{52}$Fe, $^{62}$Cu, $^{64}$Cu, $^{67}$Cu, $^{67}$Ga, $^{68}$Ga, $^{86}$Y, $^{89}$Zr, $^{90}$Y, $^{94m}$Tc, $^{94}$Tc, $^{95}$Tc, $^{99}$mTc, $^{103}$Pd, $^{105}$Rh, $^{109}$Pd, $^{111}$Ag, $^{111}$In $^{123}$I, $^{124}$I, $^{125}$I, $^{131}$I, $^{140}$La, $^{149}$Pm, $^{153}$Sm, $^{154-159}$Gd, $^{165}$Dy, $^{166}$Dy, $^{166}$Ho, $^{169}$Yb, $^{175}$Yb, $^{175}$Lu, $^{177}$Lu, $^{186}$Re, $^{188}$Re, $^{192}$Ir, $^{198}$Au, $^{199}$Au, or $^{212}$Bi.

In some embodiments of the peptide according to the disclosure, the peptide is labeled with a fluorescent label that emits in the near-infrared range of the electromagnetic spectrum. In some embodiments, the fluorescent label is FITC or a cyanine dye, such as the Cy5.5 or Cy7 dye. In some embodiments, the peptide consists of the sequence set forth in SEQ ID NO:1.

Another aspect according to the disclosure is drawn to a method of detecting intestinal neoplasia comprising: (a) contacting intestine tissue with a labeled peptide comprising the sequence set forth in SEQ ID NO:1; (b) measuring the binding of the labeled peptide to the intestine tissue; and (c) detecting intestinal neoplasia based on the measurement of binding. In some embodiments, the intestine tissue is colorectal tissue. In some embodiments, the colorectal tissue is colonic tissue. In some embodiments, the intestinal neoplasia is a precancerous lesion. In some embodiments, the intestinal neoplasia is cancer, such a colorectal cancer. In some embodiments, the intestine tissue binding the labeled peptide is not discernible as a polyp by endoscopic examination. In some embodiments, the intestine tissue is a polyp. In some embodiments, the binding occurs in vivo. Some embodiments of the method further comprise fluorescence imaging in vivo. In some of these embodiments, the fluorescence imaging is obtained using a wide-area endoscope.

As noted above, the disclosure provides peptides that bind to cMet presented on dysplastic colon cells and/or cancerous colon cells. An example of the peptides provided is the QQT*-Cy5.5 peptide, i.e., the peptide of SEQ ID NO:1 labeled with Cy5.5.

The disclosure also provides reagents comprising a peptide according to the disclosure. In some embodiments, the reagents comprise a detectable label attached to a peptide according to the disclosure. The detectable label may be detectable, for example, by microscopy, including fluorescence microscopy, ultrasound, PET, SPECT, or magnetic resonance imaging. In an embodiment, the label detectable by microscopy is a member of the cyanine family of dyes, fluorescein isothiocyanate (FITC), 7-diethylaminocoumarin-3-carboxylic acid, CF-633 or 5-carboxytetramethylrhodamine. An exemplary cyanine dye is Cy5.5.

In some embodiments, a detectable label is attached to a peptide according to the disclosure by a peptide linker. The terminal amino acid of the linker may be a lysine, such as in the exemplary linker GGGSK (SEQ ID NO:2), as noted above. In certain aspects, the linker is an Ahx linker, an amino terminal linker comprising 6-amino hexanoic acid.

In other embodiments, the reagents comprise a therapeutic moiety attached to a peptide according to the disclosure. The therapeutic moiety may be a chemopreventative or chemotherapeutic agent. In certain aspects, the therapeutic moiety is an anti-cancer agent, such as potent cytotoxins selectively active in rapidly dividing cells. Such cytotoxins include several groups of chemotherapeutics, e.g., auristatins, maytansines and calicheamicins, as well as duocarymycins and pyrrolobenzodiazepine (PBD) dimers, all of which induce DNA damage in target cells such as neoplastic cells of the colon. Exemplary auristatins are monomethyl auristatin E (MMAE) and monomethyl auristatin F (MMAF). The disclosure contemplates maytansines and derivatives thereof, such as maytansanoids. The advantageous properties of using the disclosed peptides as targeting agents also allows earlier generations of cytotoxic agents to be usefully employed as anti-cancer agents while limiting toxicities to acceptable levels. These older cytotoxic agents include, but are not limited to, vinca alkaloids, anthracyclines, glivec, taxol, camptothecin, doxorubicin, methotrexate, 5-fluorouracil, chlorambucil, and any anti-cancer agent known in the art. In a related aspect, the disclosure provides a therapeutic moiety that is an anti-inflammatory agent, such as a NSAID, e.g., celecoxib.

In yet a further aspect, the invention provides a composition comprising a reagent of the invention and a pharmaceutically acceptable excipient.

In an additional aspect, the disclosure provides a method of determining the effectiveness of a treatment for colon cancer and/or cancer metastasis, or recurrence of cancer in a patient comprising the step of administering a reagent comprising a peptide according to the disclosure attached to a detectable label to the colon of the patient, visualizing a first amount of cells labeled with the reagent, and comparing the first amount to a previously visualized second amount of cells labeled with the reagent, wherein a decrease in the first amount of cells labeled relative to the previously visualized second amount of cells labeled is indicative of effective treatment. In some embodiments, a decrease of 5% is indicative of effective treatment. In other embodiments, a decrease of about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or more is indicative of effective treatment. In some embodiments, the method further comprises obtaining a biopsy of the cells labeled by the reagent.

In another aspect, the invention provides a method for delivering a therapeutic agent to dysplastic colon cells of a patient comprising the step of administering a reagent comprising a peptide according to the disclosure attached to a therapeutic moiety to the patient.

In yet another aspect, the disclosure provides a method for delivering a therapeutic agent to colon cancer cells of a patient comprising the step of administering a reagent comprising a peptide according to the disclosure attached to a therapeutic moiety to the patient.

In still another aspect, the invention provides a kit for administering a composition according to the disclosure to a patient in need thereof, where the kit comprises a composition according to the disclosure, instructions for use of the composition and a device for administering the composition to the patient.

Other features and advantages of the disclosure will be better understood by reference to the following detailed description, including the drawing and the examples.

8 els show differences in biochemical structures. E) Peak absorbance and F) maximum fluorescence emission were seen at $\lambda_{abs}$=675 nm and $\lambda_{em}$=710 nm, respectively.

Figure 2:
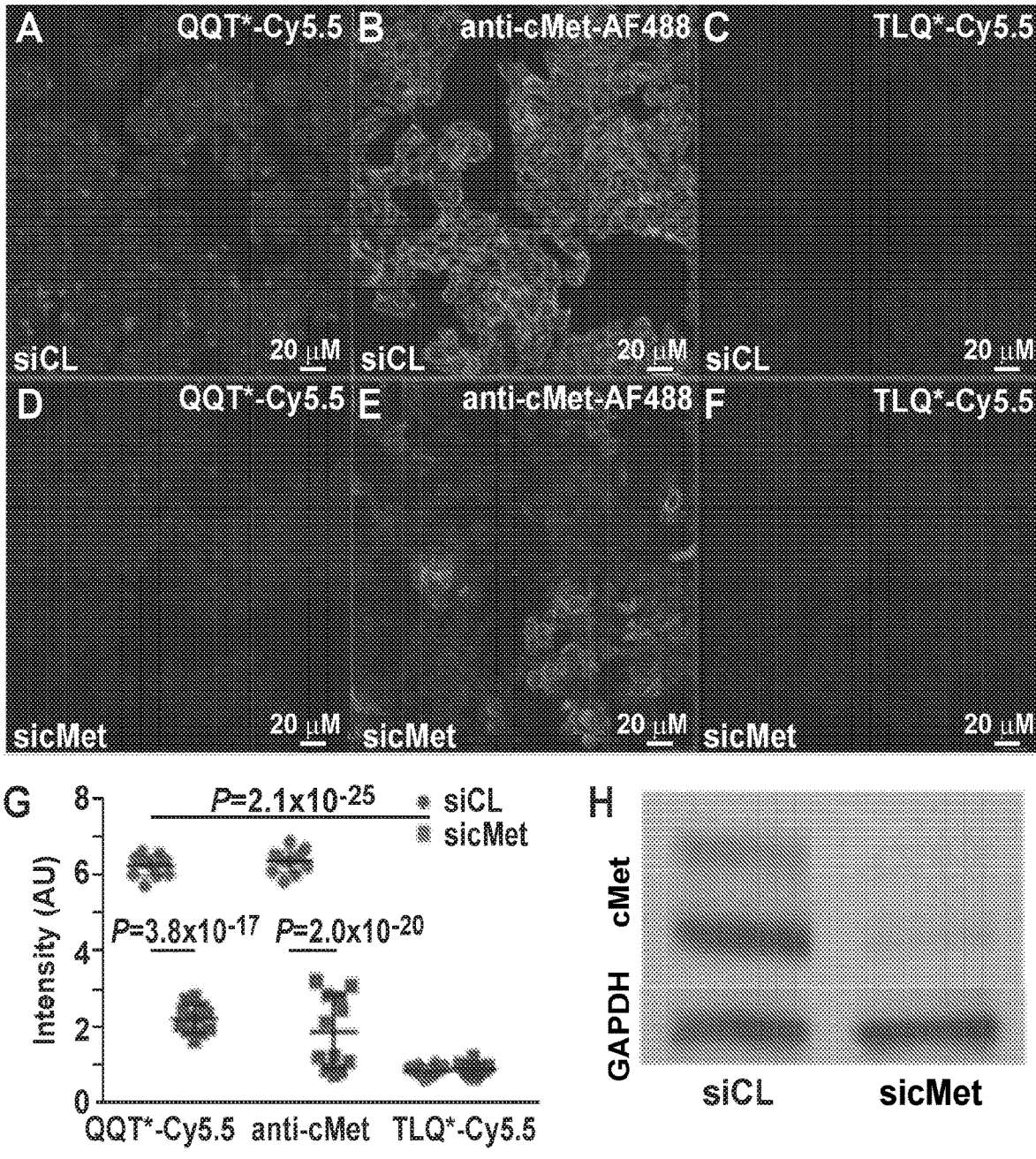

FIG. 2. In vitro validation with cMet knockdown. A) QQT*-Cy5.5 peptide (red) and B) AF488-labeled anti-cMet antibody (green) showed strong binding to the surface (arrow) of human HT29 colorectal cancer cells transfected with siCL non-targeting siRNA (control) using confocal microscopy. C) Control peptide TLQ*-Cy5.5 (red) showed minimal binding. Fluorescence intensities for D) peptide and E) antibody were reduced with HT29 knockdown cells transfected with sicMet-targeting siRNA. F) TLQ*-Cy5.5 (red) showed little binding. G) QQT*-Cy5.5 and anti-cMet-AF488 showed significantly reduced intensity reduction with knockdown of cMet by 2.9- and 4.1-fold, respectively. TLQ*-Cy5.5 showed a non-significant decrease (0.96-fold, P=0.52). Significantly greater intensity was measured for QQT*-Cy5.5 versus TLQ*-Cy5.5 (8.1-fold). A two-way ANOVA model was fit with terms for 6 conditions and 6 replicate slides on log-transformed data. Measurements were an average of 5 randomly chosen cells on 6 slides for each condition. H) Western blot showed cMet expression for each condition.

Figure 3:
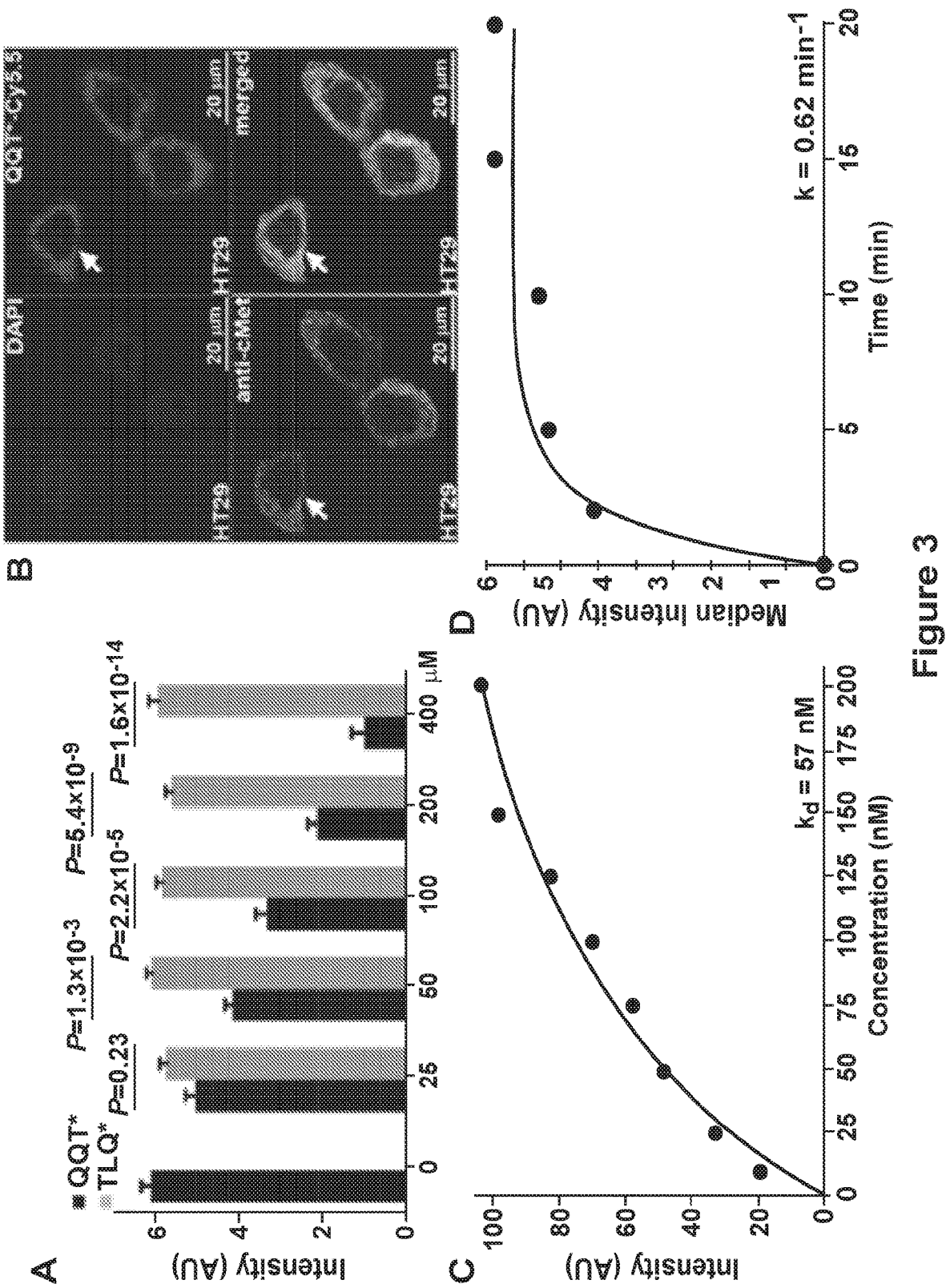

FIG. 3. Peptide specific for cMet. A) The addition of unlabeled QQT* to compete for binding with QQT*-Cy5.5 to HT29 cells resulted in a significant decrease in fluorescence intensity in a concentration-dependent manner. TLQ* showed no significant change. A two-way ANOVA model was fit with terms for the labeled peptide, concentrations of the unlabeled peptides, and their interactions, on log-transformed data. Measurements were an average of 5 randomly chosen cells on 3 slides for each condition. B) Binding of QQT*-Cy5.5 (red) and anti-cMet-AF488 (green) co-localized to the surface (arrows) of HT29 cells with ρ=0.73. C) The apparent dissociation constant $k_d$=57 nM, $R^2$=0.98, was measured for binding of QQT*-Cy5.5 to HT29 cells. D) The apparent association time constant k=0.62 min$^{-1}$ (1.6 min), $R^2$=0.97, was measured for binding of QQT*-Cy5.5 to HT29 cells. Results are representative of 3 independent experiments.

Figure 4:
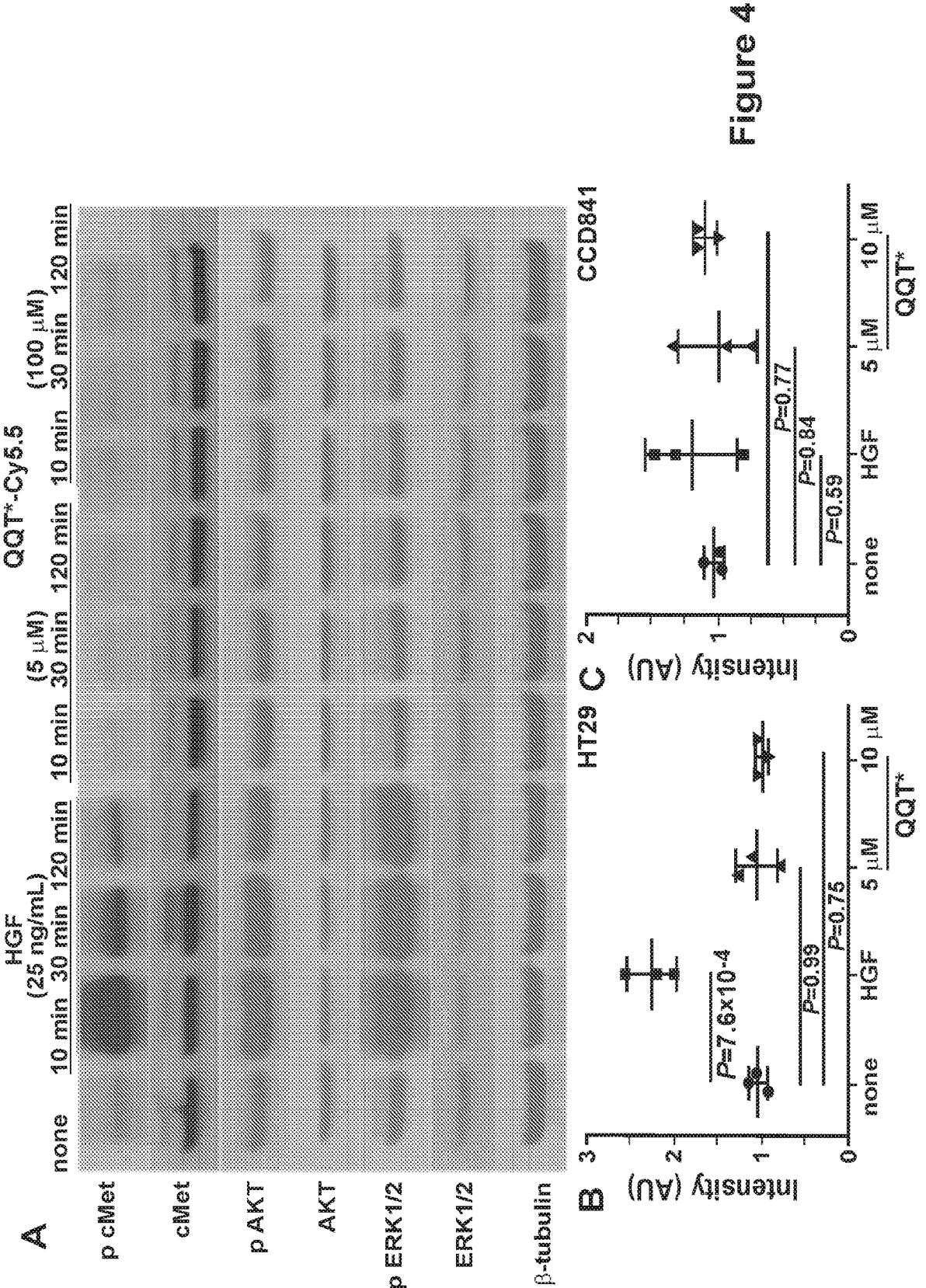

FIG. 4. Peptide effect on cell signaling and growth. Peptide binding does not affect cell signaling. (A) HGF (25 ng/mL) induced phosphorylation of cMet and downstream AKT and Erk1/2 in HT29 cells after 10, 30 and 120 min (i.e., minutes) of incubation from Western blot. HGF (100 ng/mL) was used as a positive control and no HGF (none) served as a negative control. Incubation with QQT*-Cy5.5 at either 5 or 100 μM showed no effect on p-cMet (phosphorylation activity for cMet) expression or downstream AKT and Erk1/2 signaling. (3-tubulin was used as a loading control. This group of bands is cropped from different parts of the same gel. An alamar blue assay showed increased growth of (B) HT29 but not (C) CCD841 cells with addition of HGF after 48 hours. No change is seen with either 5 or 100 μM of QQT*-Cy5.5. An ANOVA model with terms for 4 groups is fit to log-transformed data with 3 independent experiments.

Figure 5:
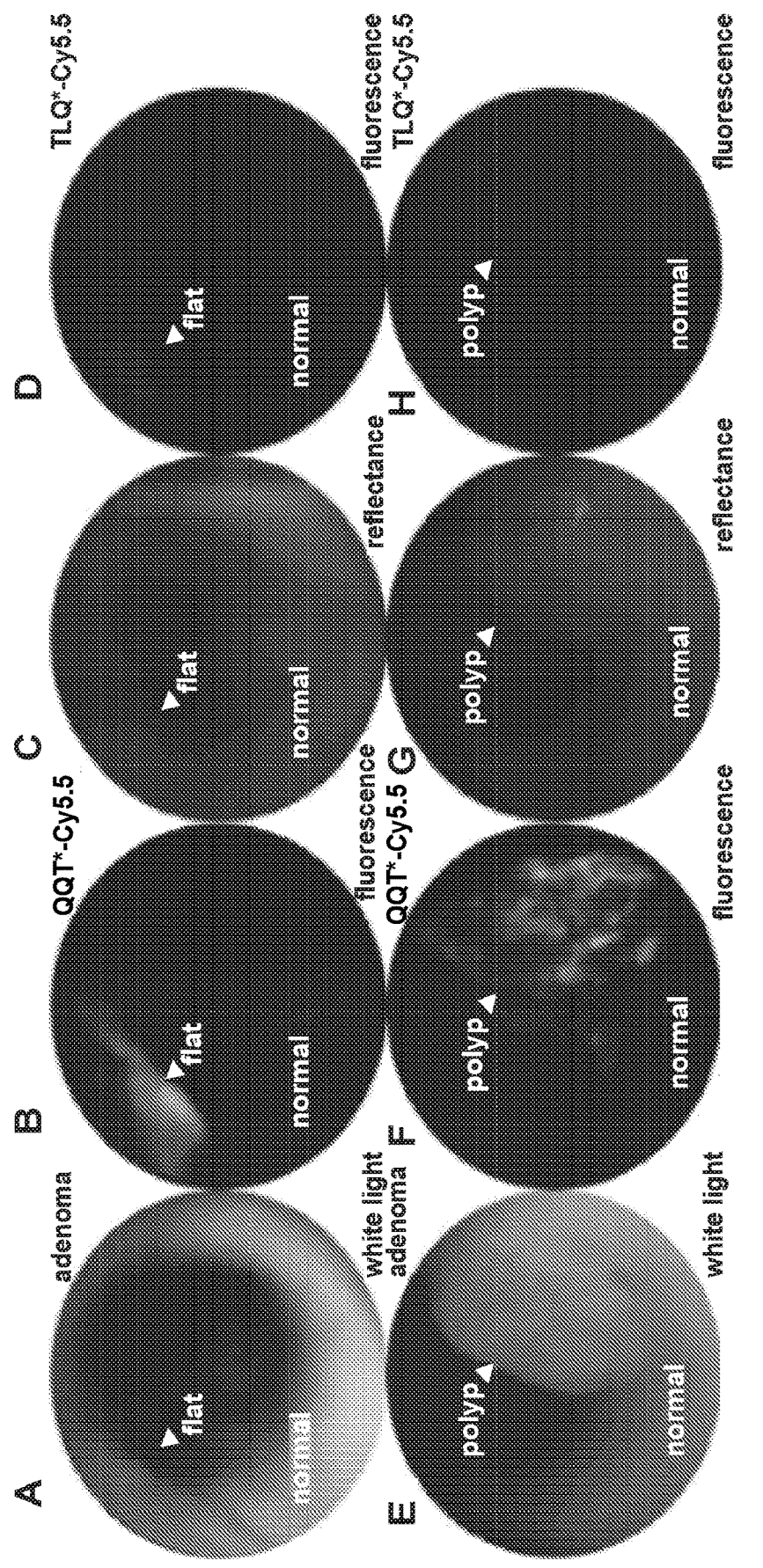
Figure 5:
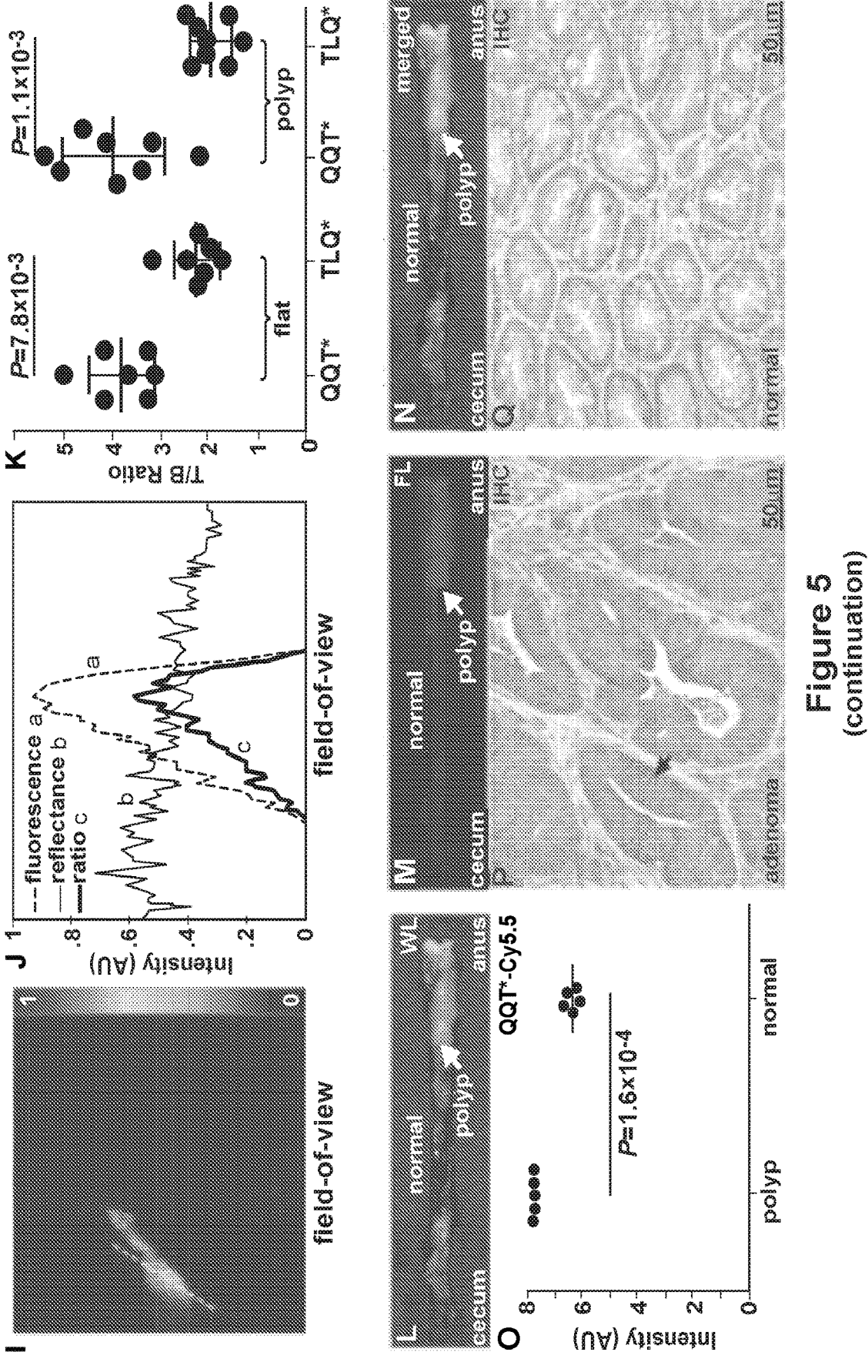

FIG. 5. Endoscopic imaging of human colon organoids in vivo. In vivo imaging in CPC;Apc mice. (A) White light image shows no grossly visible lesion (flat). (B) NIR fluorescence image after intra-rectal administration of QQT*-Cy5.5 shows increased intensity from the flat lesion (arrow). (C) Co-registered reflectance image is acquired from the same lesion. (D) Fluorescence image collected using TLQ*-Cy5.5 (control) shows minimal signal. (E) White light image of colon shows presence of a polyp (arrow). (F) QQT*-Cy5.5 shows increased fluorescence intensity from the polyp (arrow). (G) Co-registered reflectance image of polyp is collected. (H) TLQ*-Cy5.5 shows minimal signal. (I) Ratio of the fluorescence and reflectance images from the flat lesion in (A) is shown. (J) Fluorescence (red), reflectance (green), and ratio (blue) intensities from the dashed line in (I) are shown. (K) From n=8 mice, QQT*-Cy5.5 shows significantly higher mean (±SD) T/B ratio from flat lesions (n=7) and polyps (n=8) versus adjacent normal mucosa by paired t-tests on log-transformed data with 1.7 and 2.1-fold change, respectively. (L) White light image of excised colon shows numerous polyps (arrow) on exposed mucosal surface. (M) Fluorescence image collected ex vivo shows increased intensity from polyps after topical administration of QQT*-Cy5.5. (N) Merged image. (O) From n=5 mice, the mean fluorescence intensity from adenoma is 2.6-fold higher than that from normal-appearing adjacent normal mucosa by paired t-test on log-transformed data. Immunohistochemistry (IHC) shows higher expression of cMet in (P) dysplasia versus (Q) normal.

Figure 6:
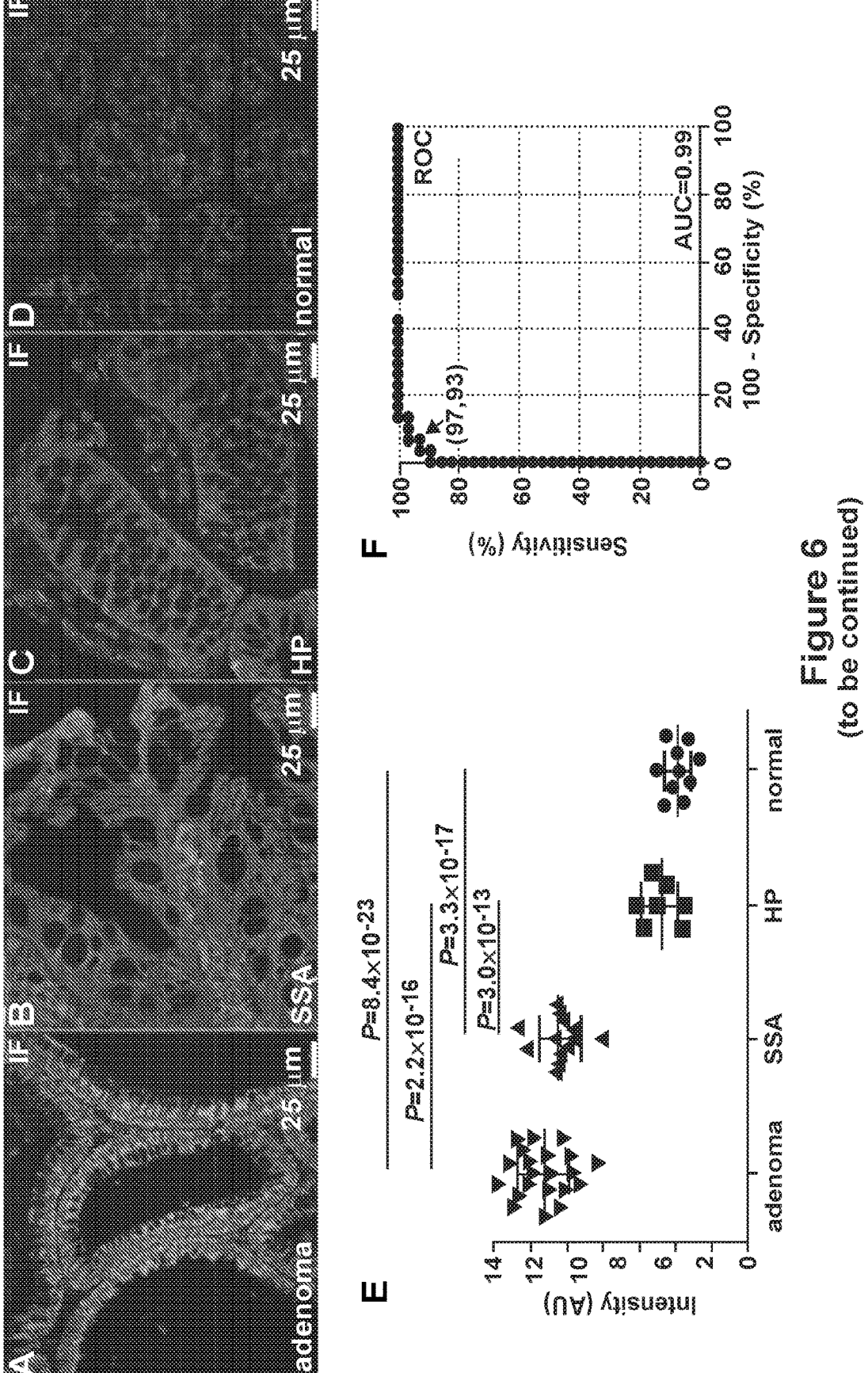
Figure 6:
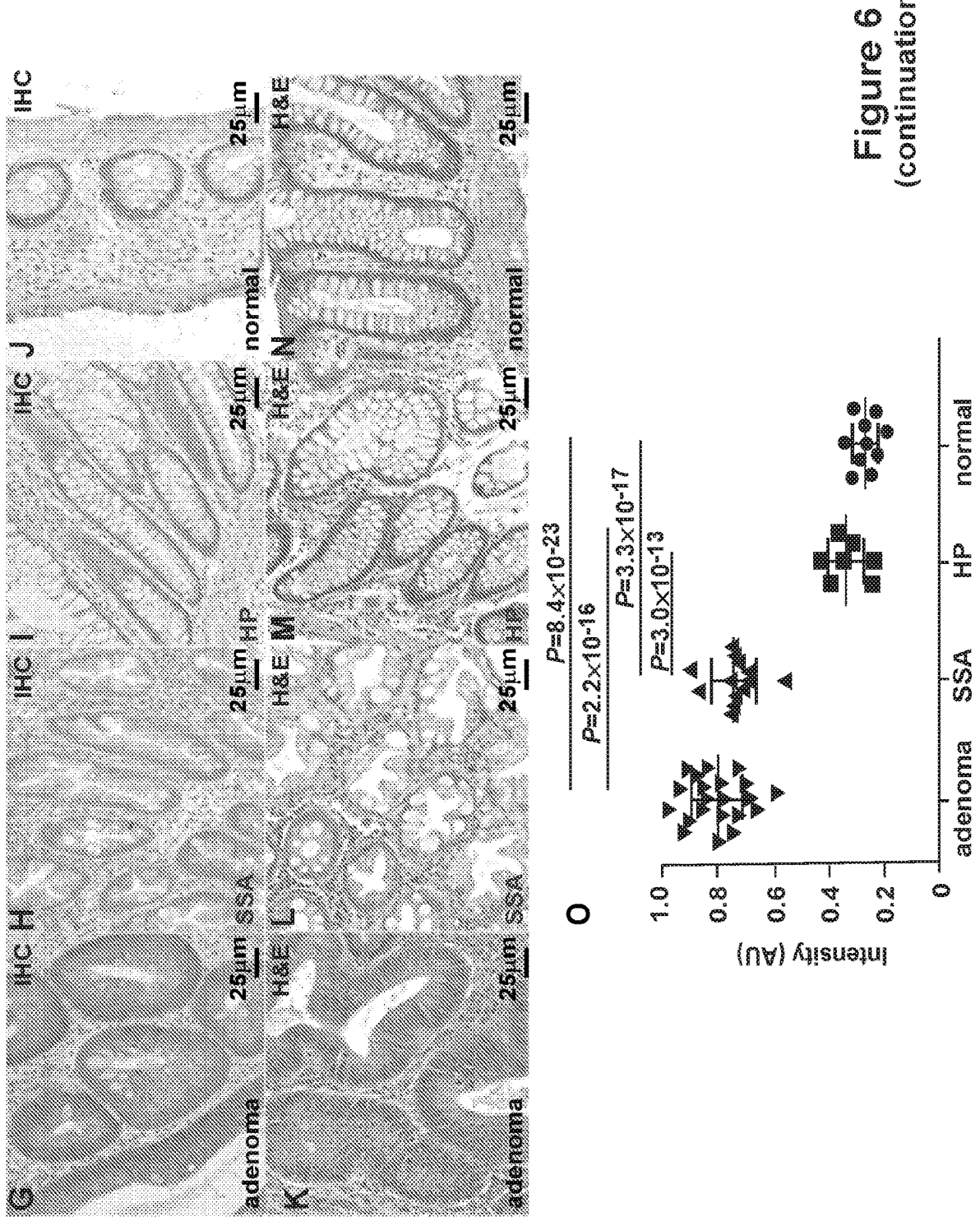

FIG. 6. Ex vivo validation with human colon specimens. Merged images showed co-localization of binding between QQT*-Cy5.5 (red) and anti-cMet-AF488 (green) to A) adenoma, B) SSA, C) hyperplastic polyp (HP), and D) normal mucosa using confocal microscopy. A Pearson's correlation coefficient of $\rho$=0.82, 0.79, 0.86, and 0.75, respectively, were measured. cMet expression was supported by immunohistochemistry (IHC) of E) adenoma, F) SSA, G) HP, and H) normal colonic mucosa. Representative histology (H&E) is shown for I) adenoma, J) SSA, K,M) HP, and L,N) normal colonic mucosa; O) the mean fluorescence intensity is significantly higher for adenoma (n=21) versus normal (n=10) and HP (n=7) with 3.0 and 2.4-fold change, respectively, using an ANOVA model with terms for 4 groups on log-transformed data with 3 replicate intensity measures per sample. For SSA (n=13), the mean fluorescence intensity is also significantly higher than that for normal and HP by 2.8 and 2.2-fold change, respectively. Measurements are the mean of 3 regions of interest (ROI) with dimensions of 20×20 $\mu m^2$ on each slide.

Figure 7:
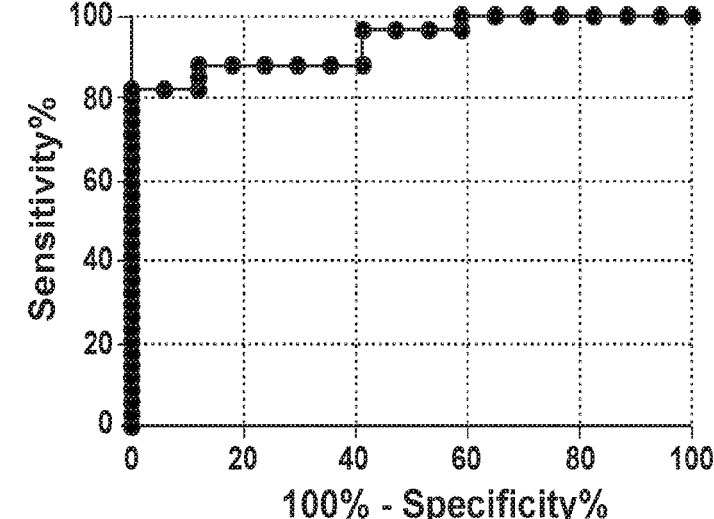
Figure 7:
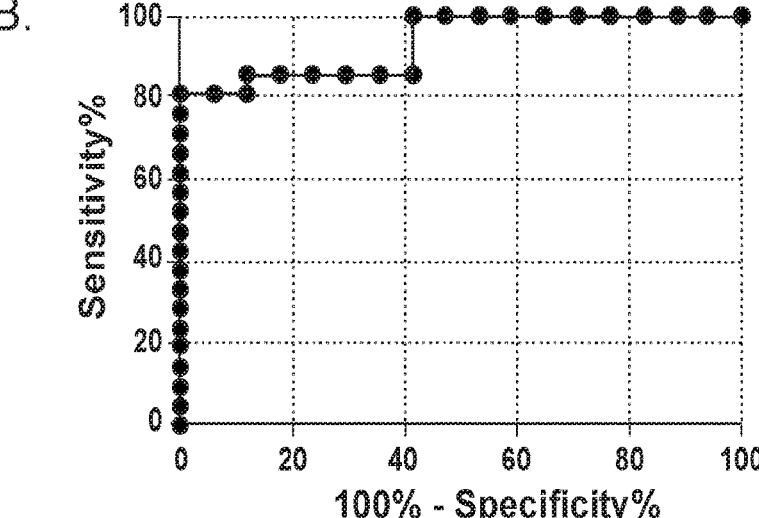
Figure 7:
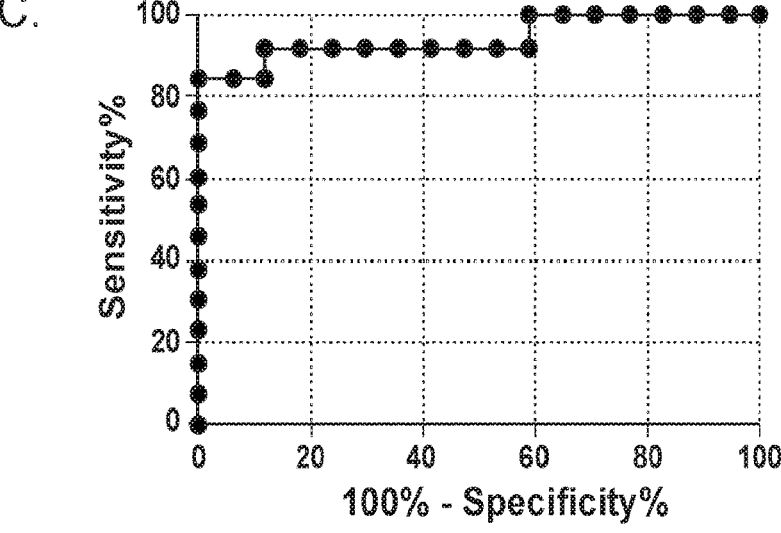

FIG. 7. Quantified immunofluorescence results with human colon specimens. A) The mean fluorescence intensity for adenoma (n=21) was significantly greater than HP (n=7) and normal (n=10) with a 2.4- and a 3.0-fold change, respectively, by two-sample t-test. The result for SSA (n=13) was also significantly greater than that for HP and normal by 2.2- and 2.8-fold change, respectively. The measurements were an average of 3 regions of interest (ROI) with dimensions of 25×25 pixels on each slide. An ANOVA model was fit with terms for 4 groups with 3 replicate intensity measures per sample. B) ROC curve showed 86% sensitivity and 88% specificity with area-under-curve (AUC) of 0.94 for distinguishing adenoma from normal and HP, and C) 92% sensitivity and 88% specificity with AUC=0.95 for distinguishing SSA from normal and HP.

Figure 8:
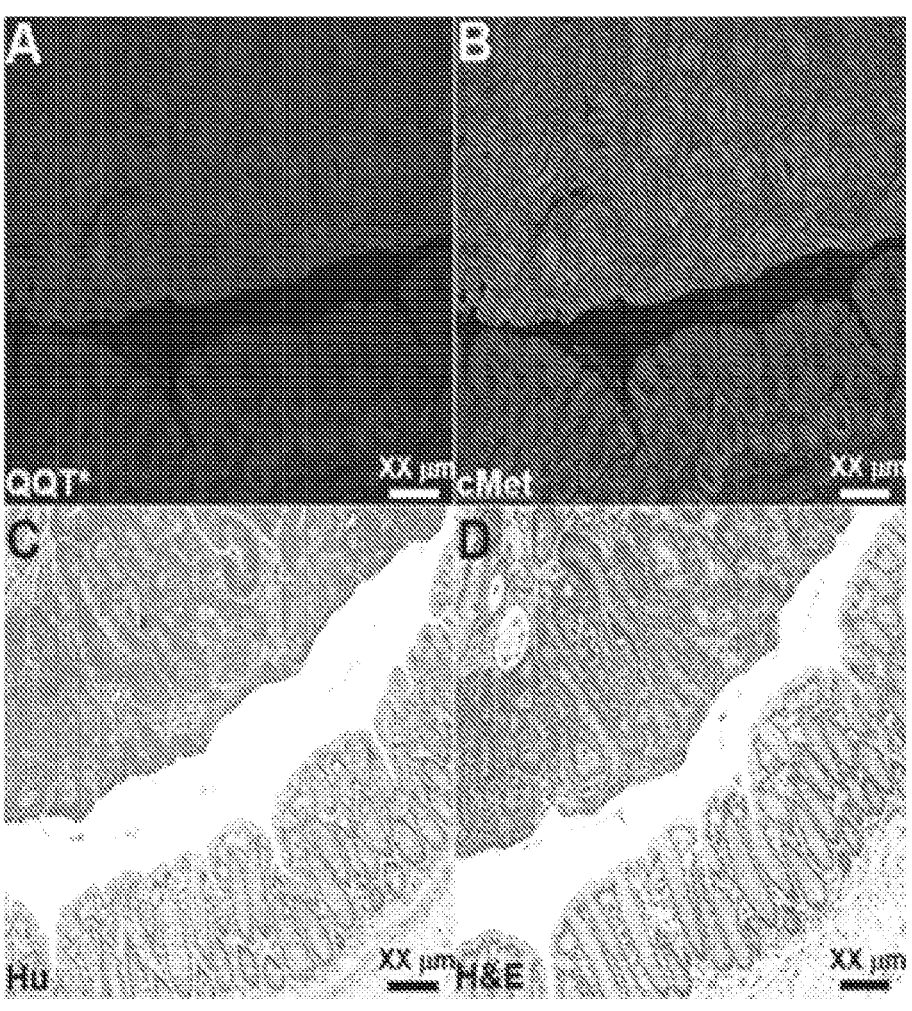
Figure 8:
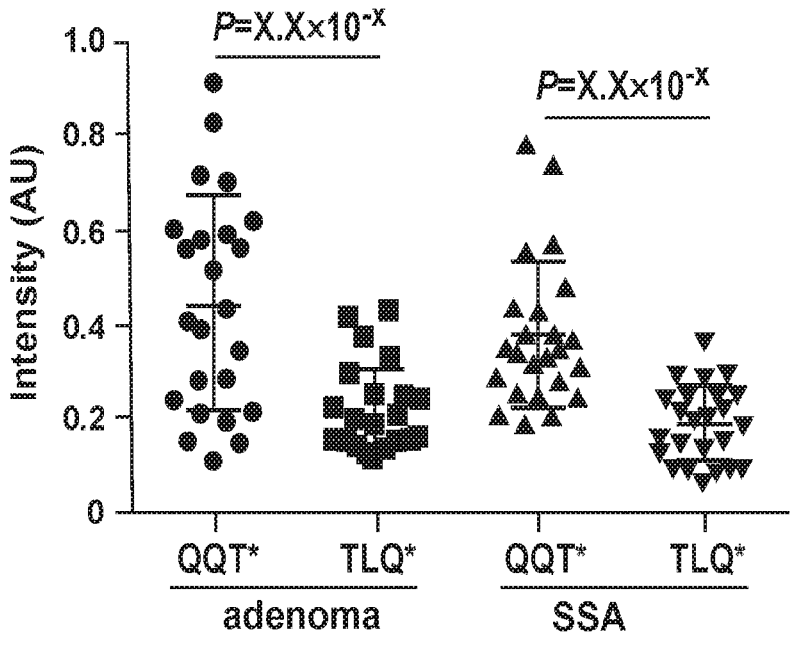

FIG. 8. On confocal microscopy, A) QQT*-Cy5.5 peptide (red) and B) AF568-labeled anti-cMet antibody (yellow) bind to adenoma human colon organoids. C) Human specific cytokeratin staining of organoids shows the success of transplantation. D) H&E staining of organoid xenograft. Statistical result of in vivo imaging with of QQT*-Cy5.5 and control TLQ*-Cy5.5 in human adenoma organoid xenografts. The fluorescence intensity is significantly higher with QQT* than TLQ* by 3.2-fold.

Figure 9:
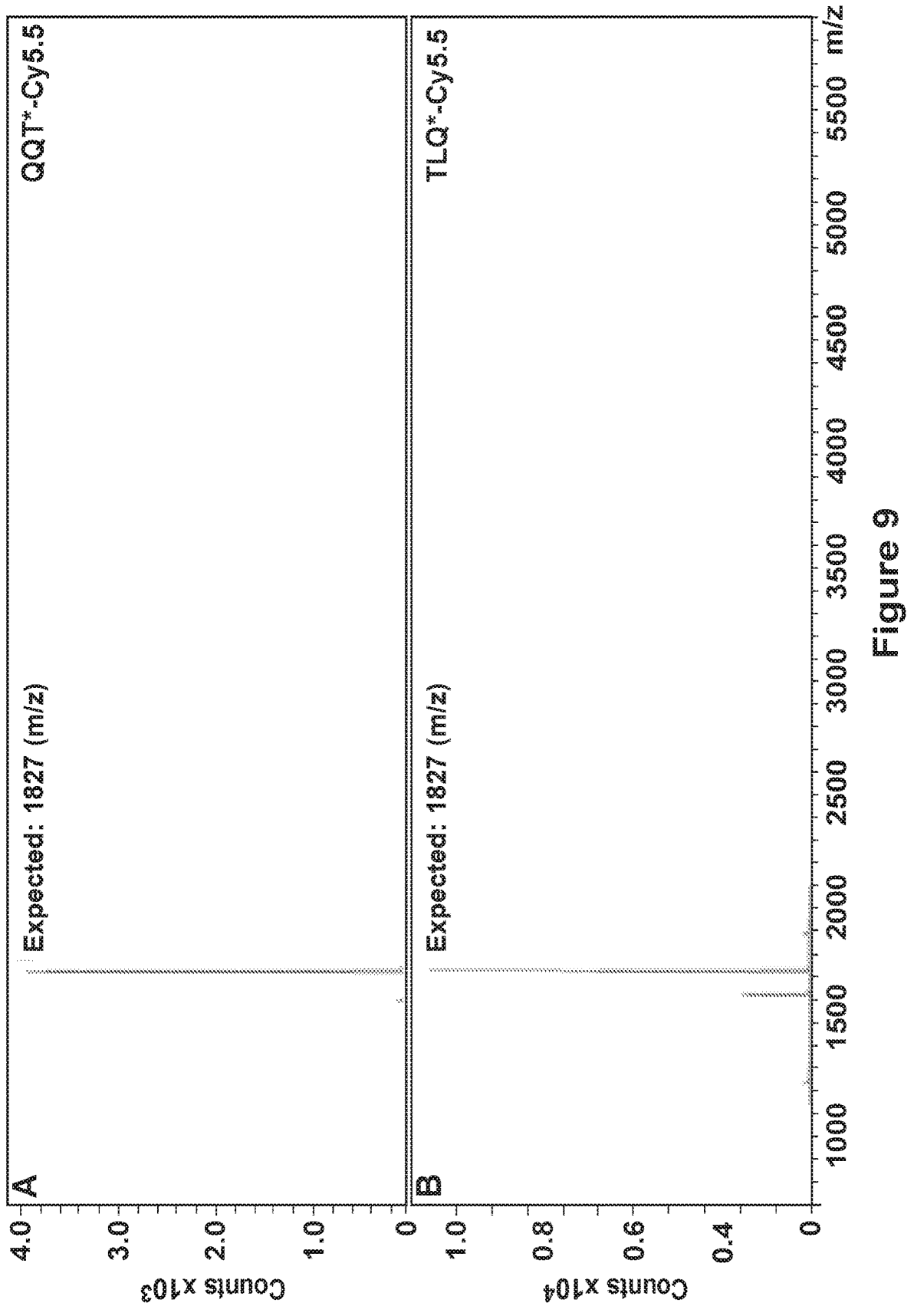

FIG. 9. Mass spectrometry of Cy5.5-labeled peptides. Experimental mass-to-charge (m/z) ratios for A) QQT*-Cy5.5 and B) TLQ*-Cy5.5 were found to be 1827.67, which showed agreement with the expected value.

Figure 10:
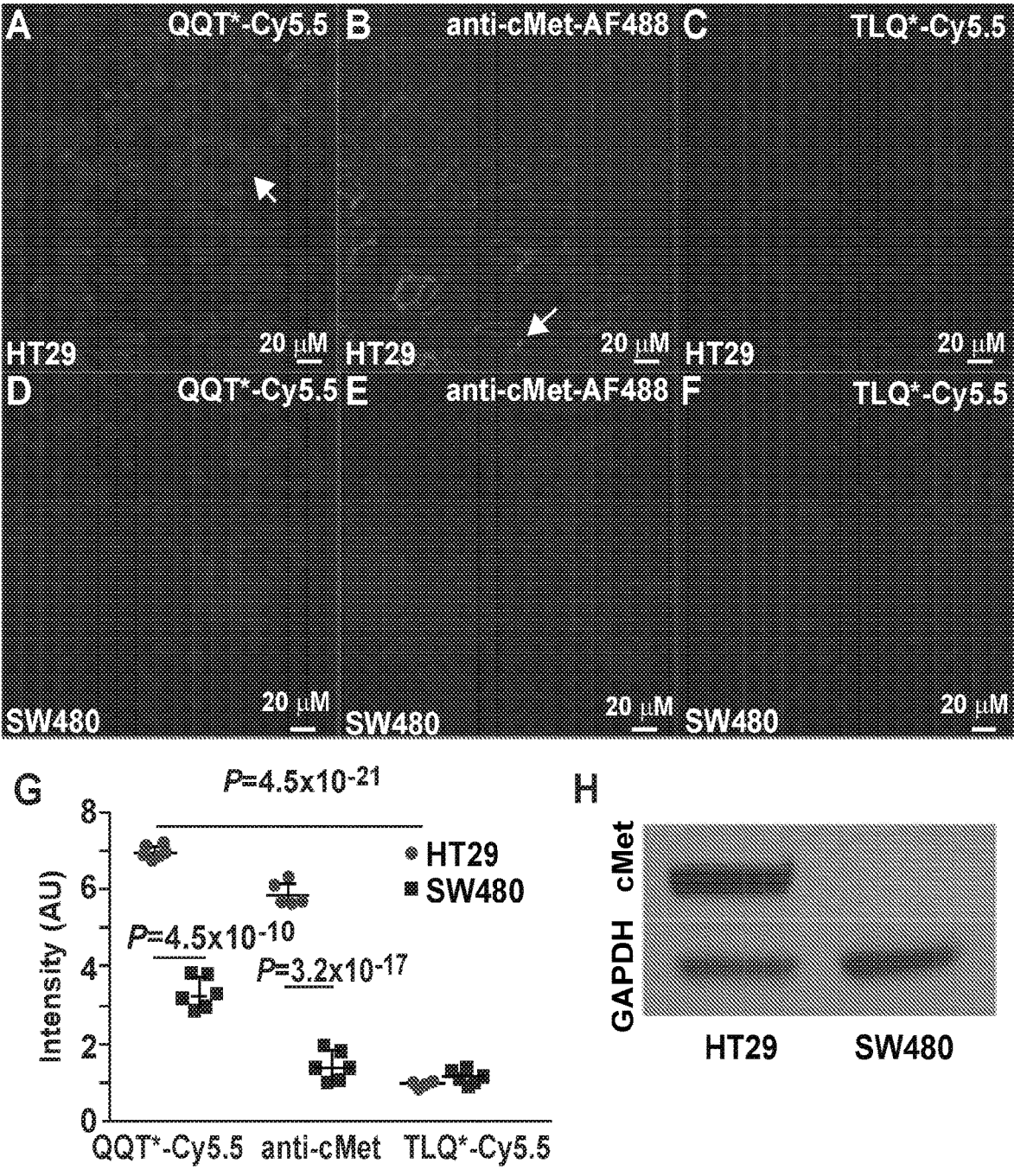

FIG. 10. Peptide validation with human colorectal cancer cells in vitro. On confocal microscopy, A) QQT*-Cy5.5 (red) and B) anti-cMet-AF488 (green) showed strong binding to surface (arrow) of HT29 cells (cMet+). C) Control peptide TLQ*-Cy5.5 (red) showed minimal binding. By comparison, reduced signal was seen with D) peptide and E) antibody to SW480 cells (cMet−). F) TLQ*-Cy5.5 (red) showed little binding. G) Quantified results showed that the mean intensity for QQT*-Cy5.5 and anti-cMet-AF488 were significantly greater with HT29 versus SW480 cells with 2.1- and 4.3-fold change, P=4.5×10⁻¹⁰ and 3.2×10⁻¹⁷, respectively. TLQ*-Cy5.5 showed a non-significant decrease (0.85 fold-change, P=0.07). Intensity of QQT*-Cy5.5 for HT29 was significantly greater than TLQ*-Cy5.5 for HT29 cells (7.5-fold change, P=4.5×10⁻²¹). Two-way ANOVA models were fit with terms for 6 conditions and 6 replicate slides on log-transformed data. Measurements were an average of 5 randomly chosen cells on 6 slides for each condition. H) Western blot showed cMet expression levels for each cell.

Figure 11:
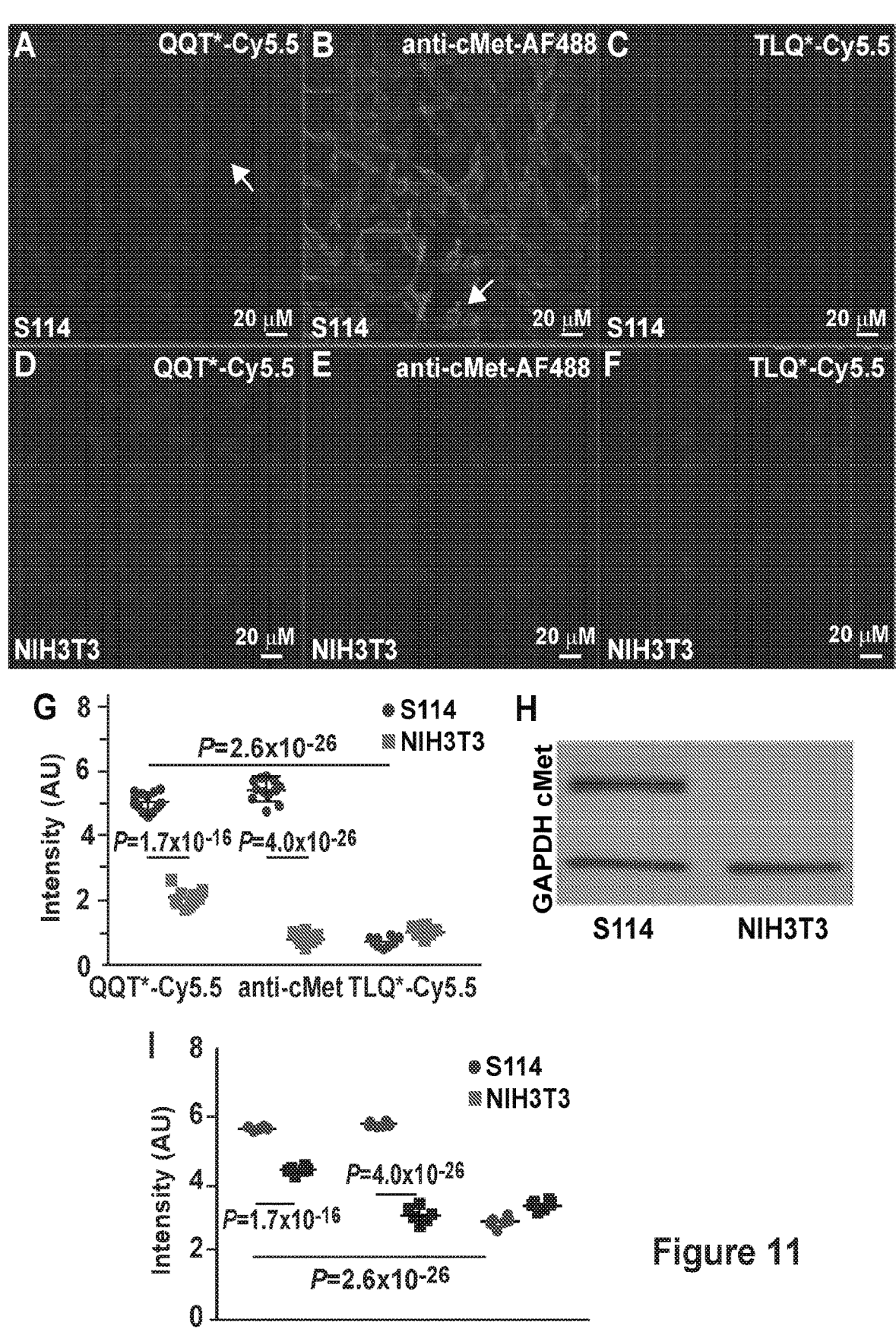

FIG. 11. Peptide validation with mouse cells in vitro. On confocal microscopy, A) QQT*-Cy5.5 (red) and B) anti-cMet-AF488 (green) showed strong binding to the surface (arrow) of S114 cells (cMet+). C) Control peptide TLQ*-Cy5.5 (red) showed minimal binding. By comparison, reduced signal was seen with D) peptide and E) antibody to NIH3T3 cells (cMet−). F) TLQ*-Cy5.5 (red) showed little binding. G) Quantified results showed that the mean intensity for QQT*-Cy5.5 and anti-cMet-AF488 were significantly greater with S114 versus NIH3T3 cells with 2.4- and 6.7-fold change, P=1.7×10⁻¹⁶ and 4.0×10⁻²⁶, respectively. TLQ*-Cy5.5 showed a non-significant decrease (0.72-fold change, P=8.2×10⁻⁷). Intensity of QQT*-Cy5.5 for S114 was significantly greater than TLQ*-Cy5.5 for S114 cells (7.0-fold change, P=2.6×10⁻²⁶). Two-way ANOVA models were fit with terms for 6 conditions and 6 replicate slides on log-transformed data. Measurements were an average of 5 randomly chosen cells on 6 slides for each condition. H) Western blot showed cMet expression levels for each cell. I) The mean intensity was significantly greater for QQT*-Cy5.5 and anti-cMet-AF488 with S114 versus NIH3T3 cells with 2.4 and 6.7-fold change, respectively. TLQ*-Cy5.5 shows a non-significant increase. The mean intensity was significantly greater for QQT*-Cy5.5 versus TLQ*-Cy5.5 with 7.0-fold change. The S114 versus NIH3T3 difference was significantly higher for QQT*-Cy5.5 than the same difference for TQL*-Cy5.5 (P=1.3×10⁻⁸). An ANOVA model was fit to log-transformed data with terms for 6 conditions. There were 6 replicate slides per condition and 10 cells measured per slide.

Figure 12:
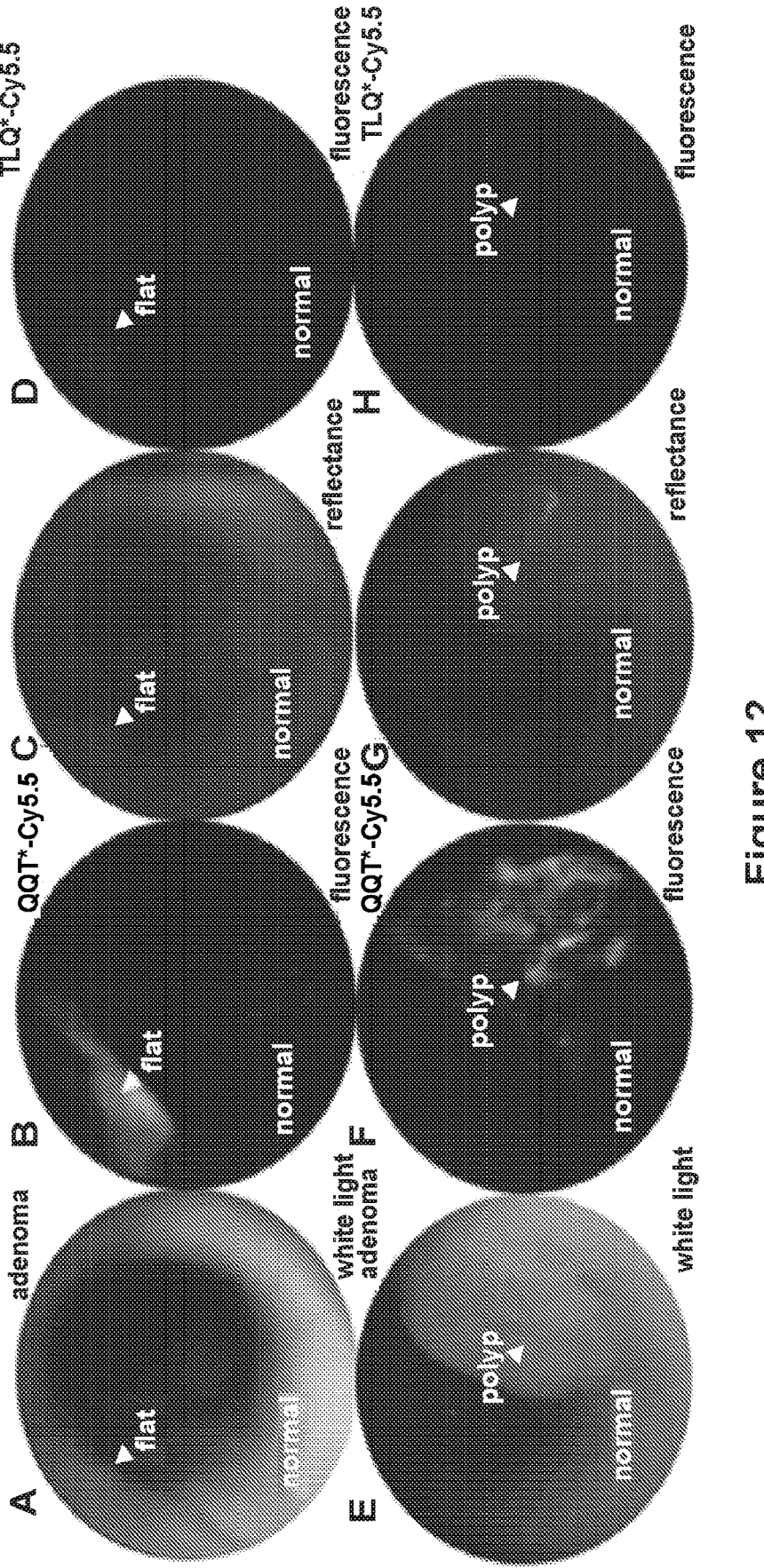
Figure 12:
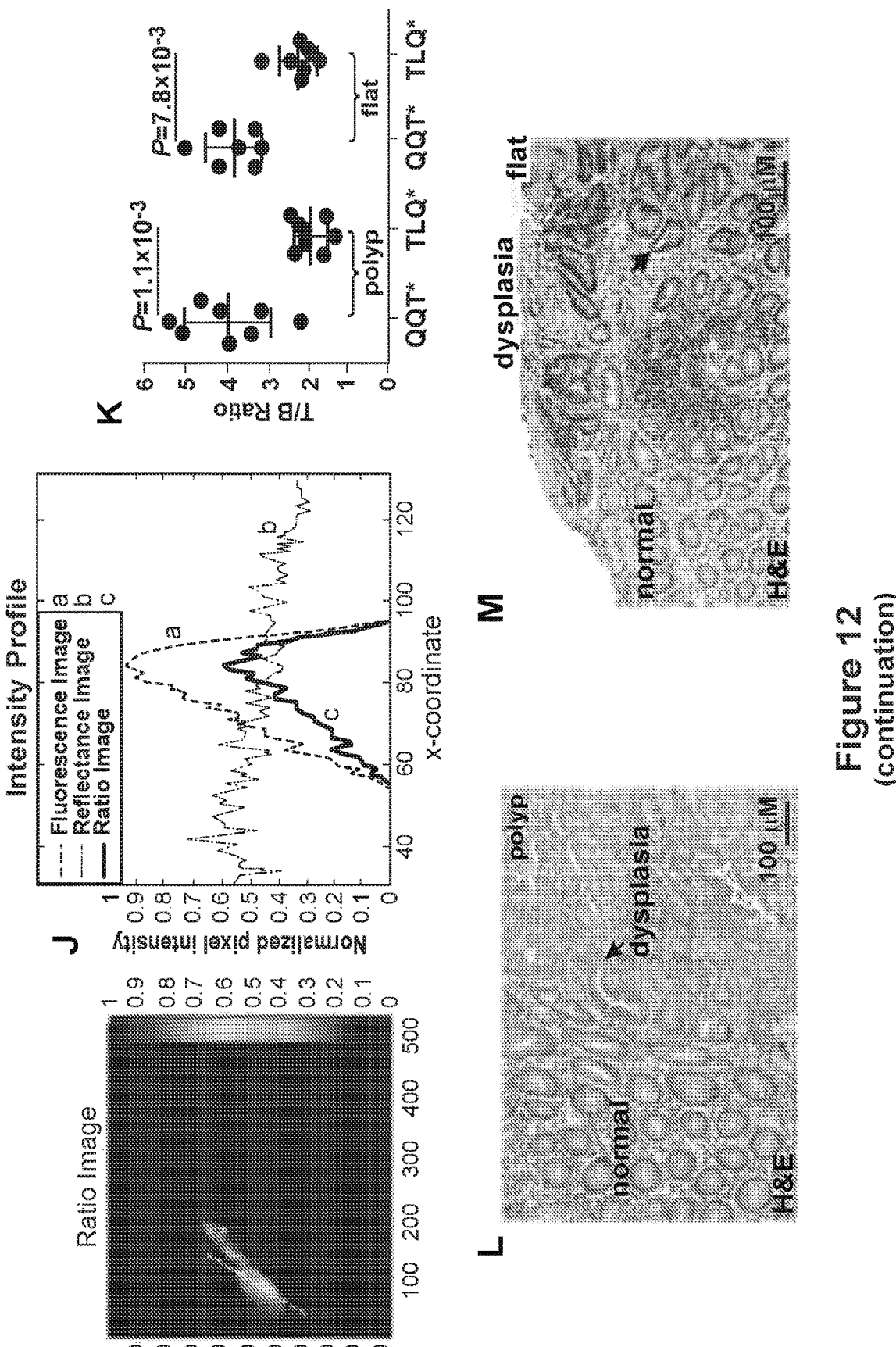

FIG. 12. In vivo imaging in CPC;Apc mouse. A) White light image showed no grossly visible lesions (polyps), consistent with the presence of a flat lesion. B) NIR fluorescence image with QQT*-Cy5.5 showed the presence of a flat lesion (arrow). C) Reflectance image registered with fluorescence was acquired. D) Image of same region with TLQ*-Cy5.5 (control) showed minimal signal. E) White light endoscopic image of colon showed presence of a spontaneous polyp (arrow) and normal-appearing mucosa. F) NIR fluorescence image after topical administration of QQT*-Cy5.5 showed increased intensity from polyp (arrow). G) Reflectance image registered with fluorescence was acquired. H) Image with TLQ*-Cy5.5 showed minimal signal. I) The ratio of the fluorescence and reflectance images from the flat lesion is shown in FIG. S4A. J) Fluorescence (red), reflectance (green), and ratio (blue) values from dashed line in FIG. S4I. K) From n=8 mice, QQT*-Cy5.5 showed higher mean (±SD) T:B ratio from polyps (n=8) and flat lesions (n=7) compared with that from adjacent normal mucosa, 3.85±1.1 and 3.76±0.67, respectively, $P=1.1\times10^{-3}$ and $P=7.8\times10^{-3}$ by paired t test. Histology (H&E) of the L) polyp and M) flat lesion with adjacent normal mucosa showed signs of low-grade dysplasia.

Figure 13:
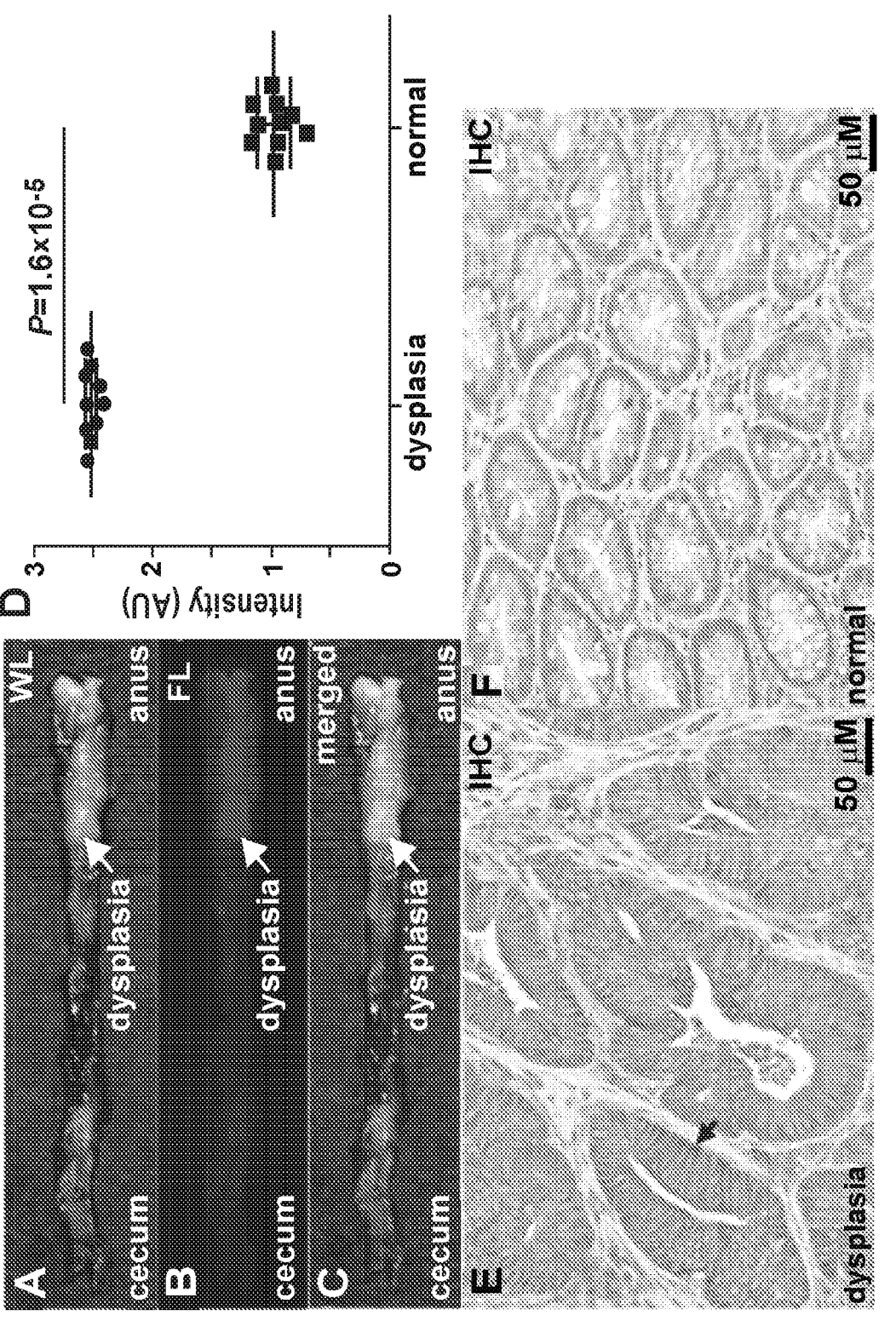
Figure 13:
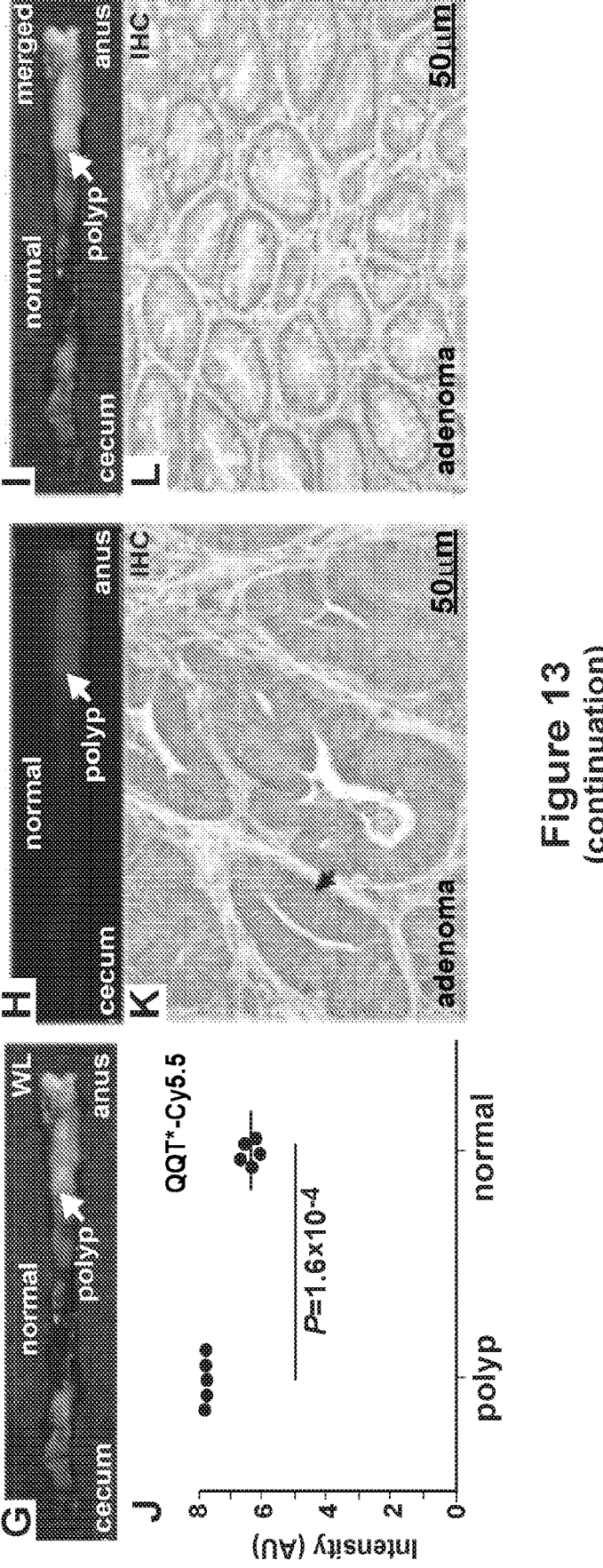

FIG. 13. Macroscopic validation of cMet expression in CPC;Apc mouse colon. A) White light image showed numerous dysplastic polyps (arrow) on exposed mucosal surface of excised mouse colon. B) Fluorescence image showed increased intensity from the polyps after topical administration of QQT*-Cy5.5. C) Merged image is shown. D) From n=5 mice, the mean fluorescence intensity from 10 regions of dysplasia was 2.7-fold higher than that from uninvolved surrounding normal mucosa, $P=1.6\times10^{-5}$ by paired t-test. Overexpression of cMet in E) dysplasia versus F) normal mucosa is supported by immunohistochemistry (IHC). (G-I) Images of tissue samples are shown. (J) Fluorescence intensity from polyp versus normal samples is shown. (K) Image of tissue sample is shown. (L) White light image of excised colon shows numerous polyps (arrow) on exposed mucosal surface. (M) fluorescence image collected ex vivo shows increased intensity from polyps after topical administration of QQT*-Cy5.5. (N) Merged image. (O) From n=5 mice, the mean fluorescence intensity from adenoma is 2.6-fold higher than that from normal-appearing adjacent normal mucosa by paired t-test on log-transformed data. Immunohistochemistry (IHC) shows higher expression of cMet in (P) dysplasia versus (Q) normal.

Figure 14:
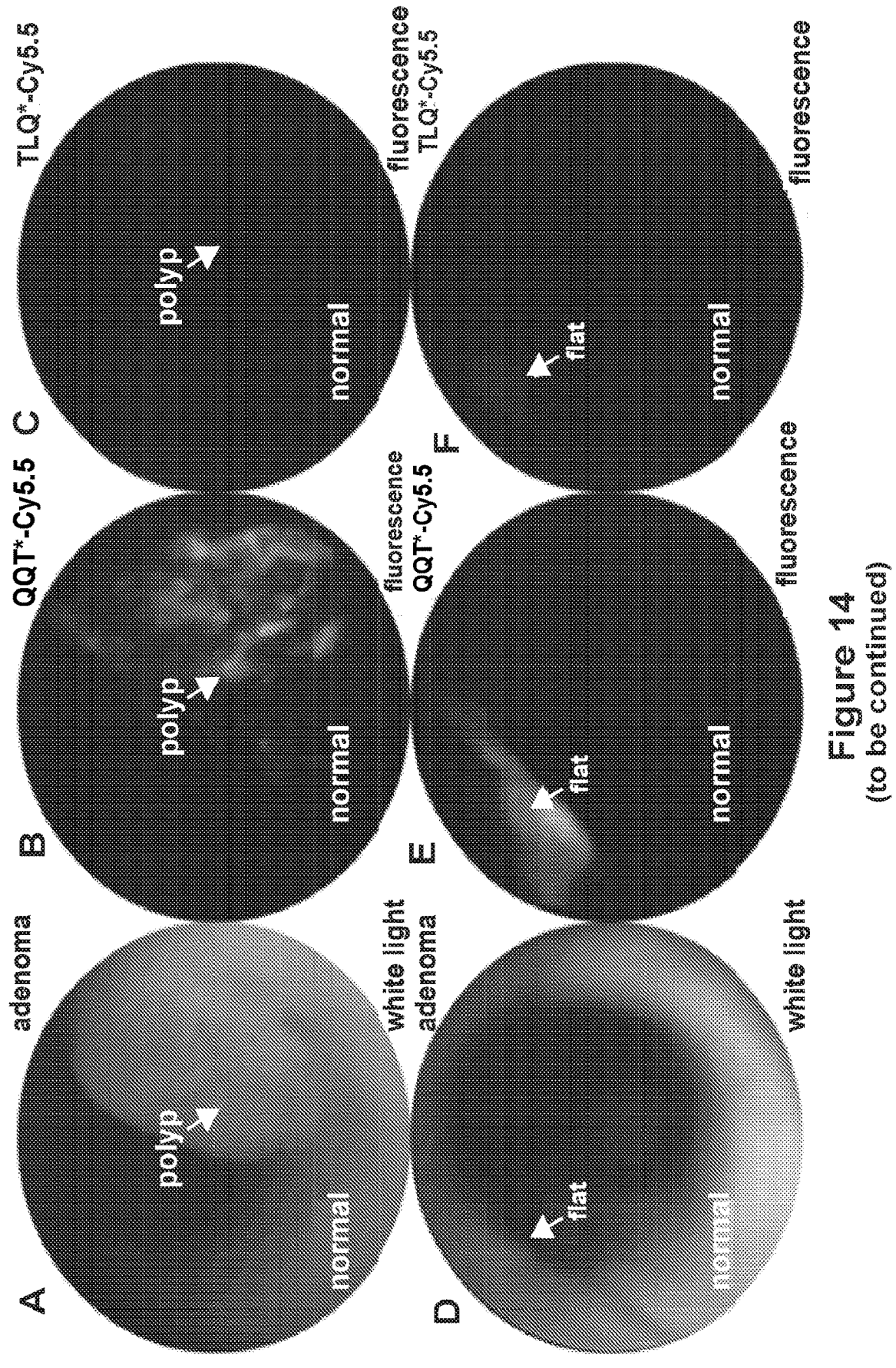
Figure 14:
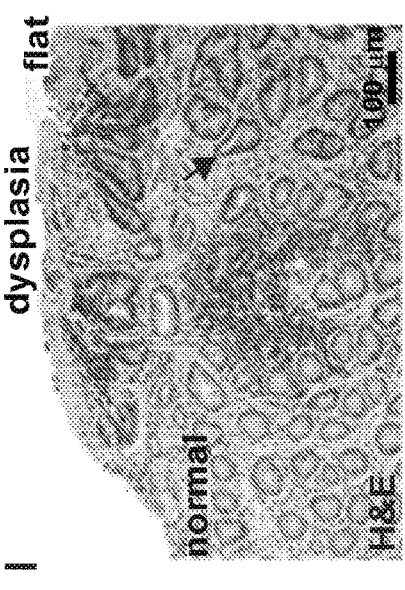
Figure 14:
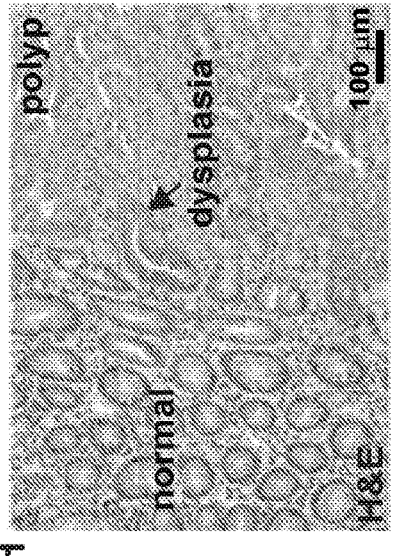
Figure 14:
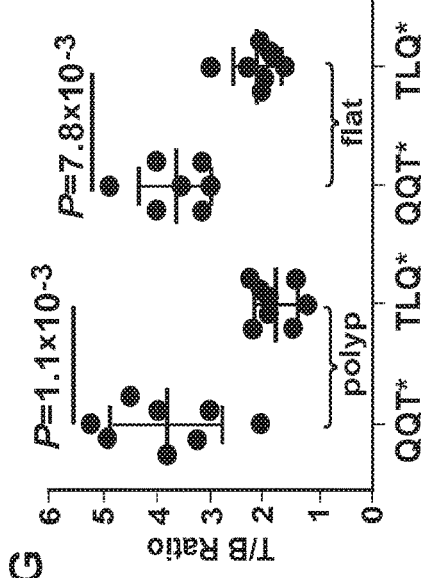

FIG. 14. In vivo imaging in CPC;Apc mouse. A) White light endoscopic image of colon showed presence of a spontaneous polyp (arrow) and normal-appearing mucosa. B) NIR fluorescence image after topical administration of QQT*-Cy5.5 showed increased intensity from polyp (arrow). C) Image of same region with TLQ*-Cy5.5 (control) showed minimal signal. D) White light image showed no grossly visible lesions (polyps). E) NIR fluorescence image with QQT*-Cy5.5 showed presence of flat lesion (arrow). F) Image with TLQ*-Cy5.5 showed minimal signal. G) From n=8 mice, QQT*-Cy5.5 showed higher mean (±SD) T:B ratio from polyps (n=8) and flat lesions (n=7) compared with that from adjacent normal mucosa, 3.85±1.1 and 3.76±0.67, respectively, $P=1.1\times10^{-3}$ and $P=7.8\times10^{-3}$ by paired t test. Histology (H&E) of the H) polyp and I) flat lesion with adjacent normal mucosa showed signs of low-grade dysplasia.

Figure 15:
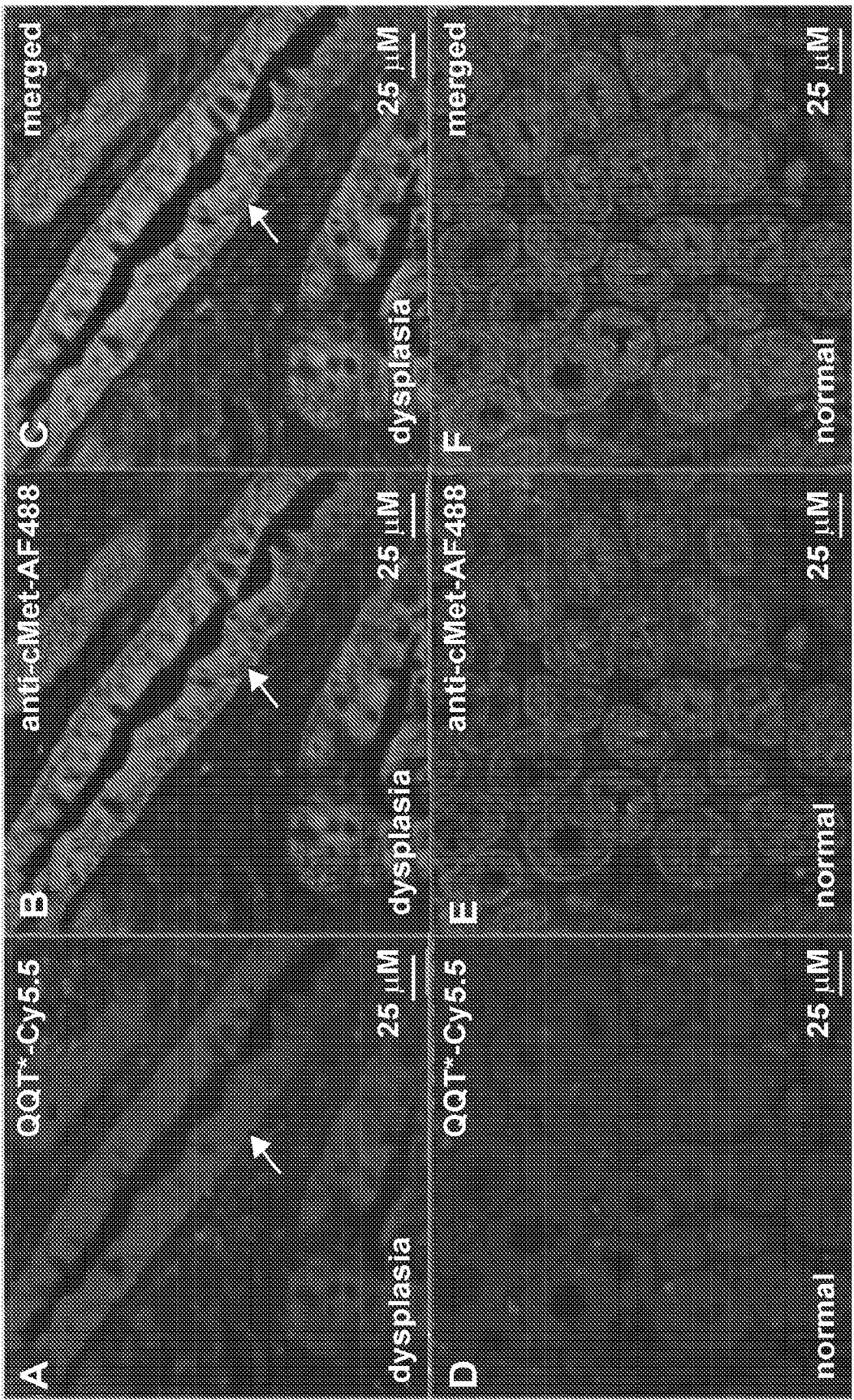
Figure 15:
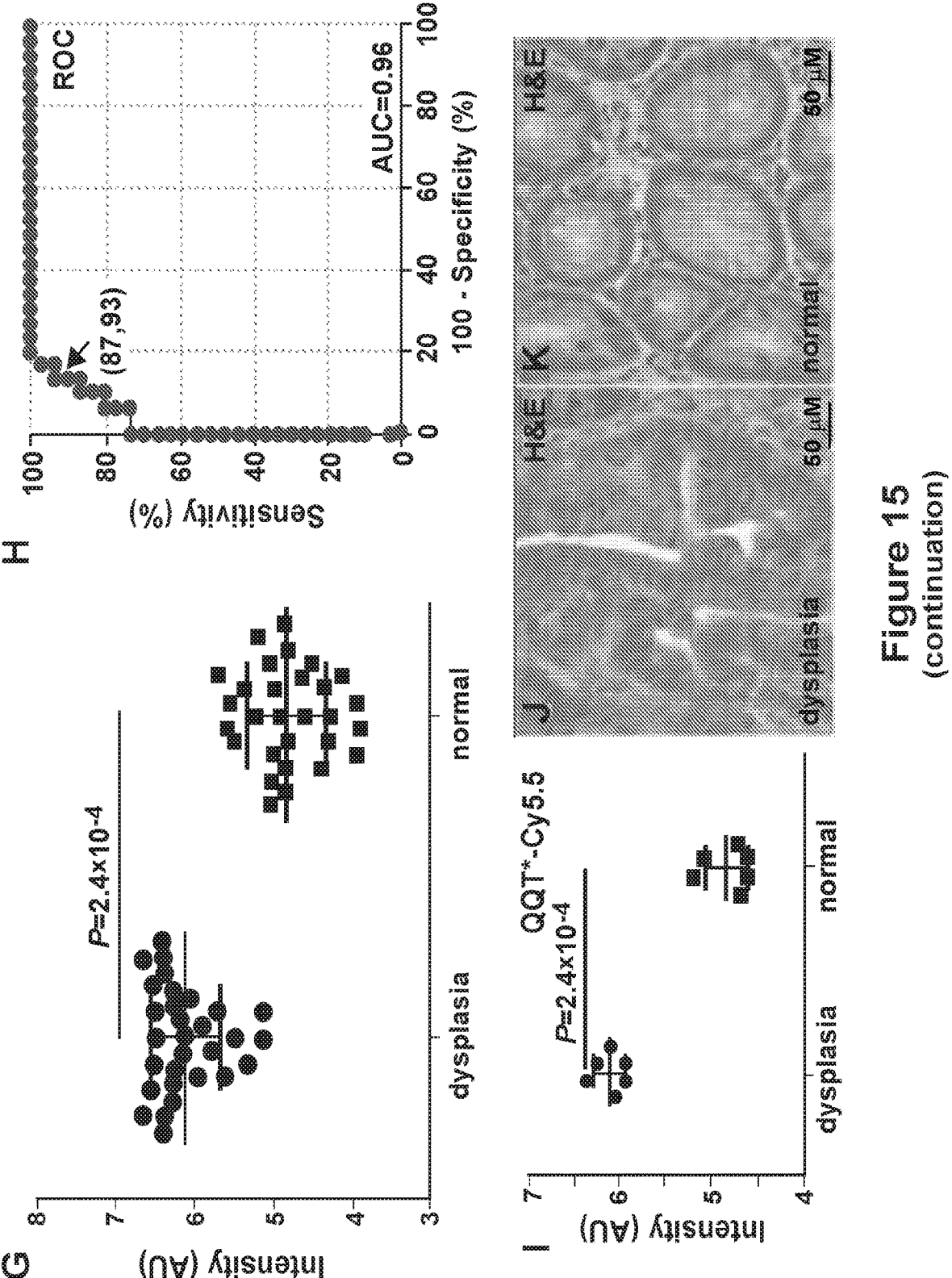

FIG. 15. Microscopic validation of cMet expression in CPC;Apc mouse colon. On confocal microscopy, binding of A) QQT*-Cy5.5 peptide (red) and B) AF488-labeled anti-cMet antibody (green) co-localized to the surface of dysplastic colonocytes (arrows) in tubular adenoma. C) On the merged image, a Pearson's correlation coefficient of □=0.78 was measured. D-F) Reduced signal was seen for normal mucosa. G, I) Adenoma (n=30) showed significantly higher mean (±SD) fluorescence intensities than normal (n=30), 6.2±0.17 and 4.9±0.25, respectively, $P=2.4\times10^{-4}$ by paired t-test on log-transformed data. H) ROC curve shows 93% sensitivity and 87% specificity with AUC=0.96 to distinguish dysplasia from normal. J, K) Histology (H&E) is shown.

Figure 16:
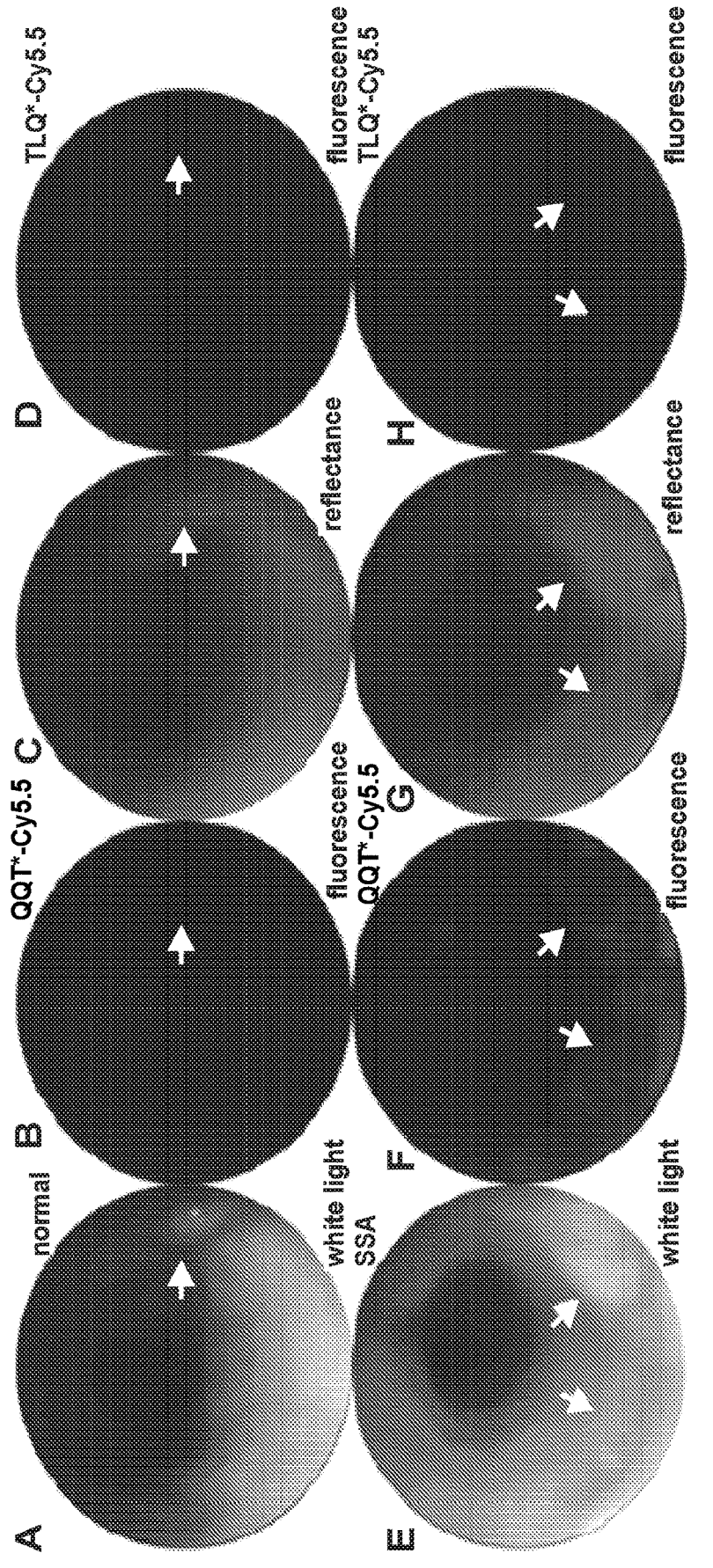
Figure 16:
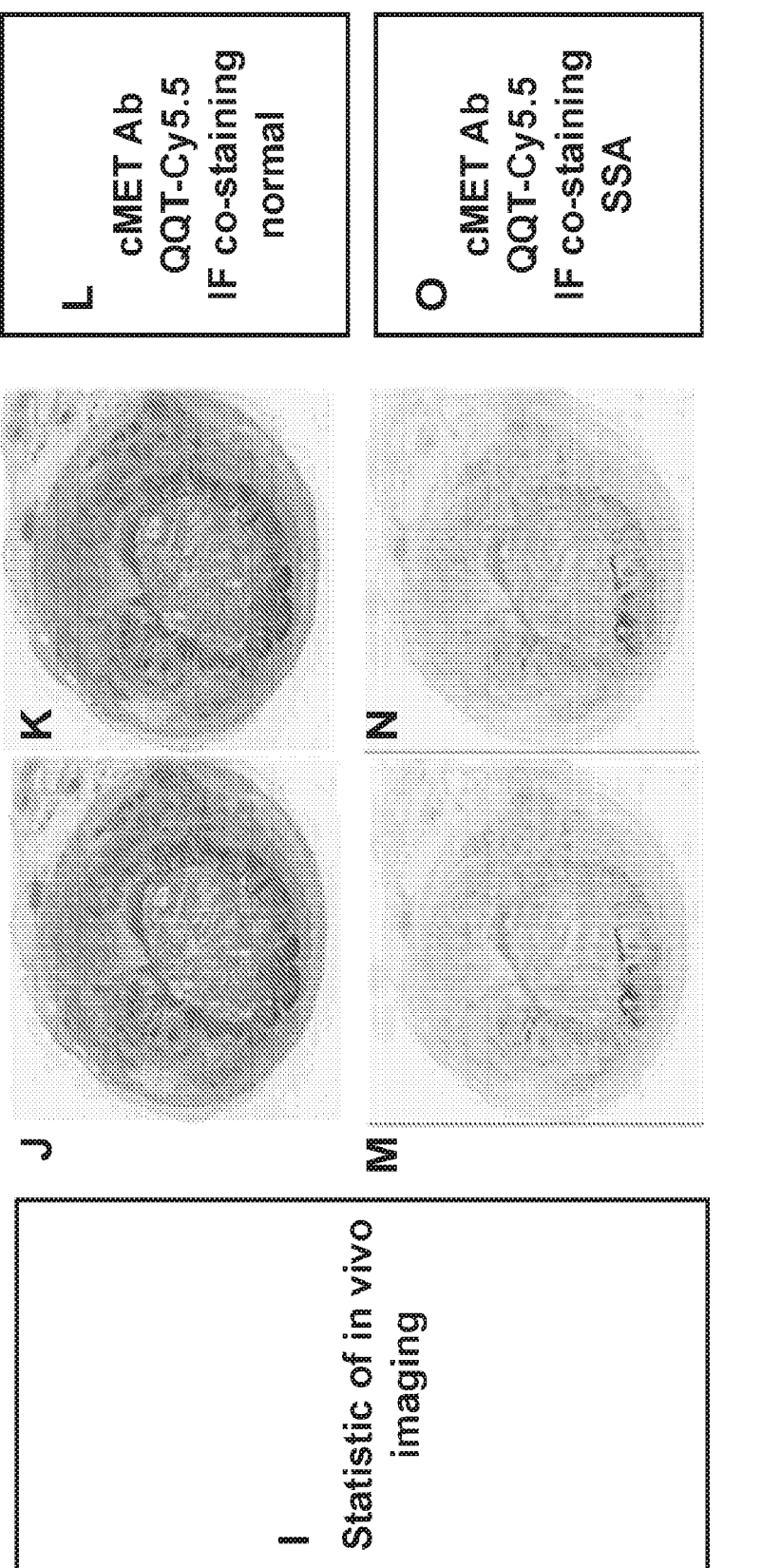

FIG. 16. In vivo imaging of normal and SSA human colon organoids. White light images showed patient-derived normal mucosa (arrow) A) and patient-derived SSA (arrow) E) implanted in the colon of a NOD/SCID mouse. Fluorescence images were collected after topical administration of QQT*-Cy5.5, and showed intense signal from SSA organoid (arrow) F) while minimal intensity from normal organoid (arrow) B). C,G) Registered reflectance image are shown. After 3 days, imaging using TLQ*-Cy5.5 (control) from the same normal D) and SSA H) organoids showed little signal (arrow). I) For in vivo imaging, the mean fluorescence intensity for SSA organoids was found to be significantly greater than from normal organoids. H&E staining show the histology of transplanted normal J) and SSA M) organoids. Human-specific hcytokeratin staining showed the success of normal K) and SSA N) organoid transplantation. IF co-localization of cMet and QQT*-Cy5.5 on normal L) and adenoma O) organoids.

Figure 17:
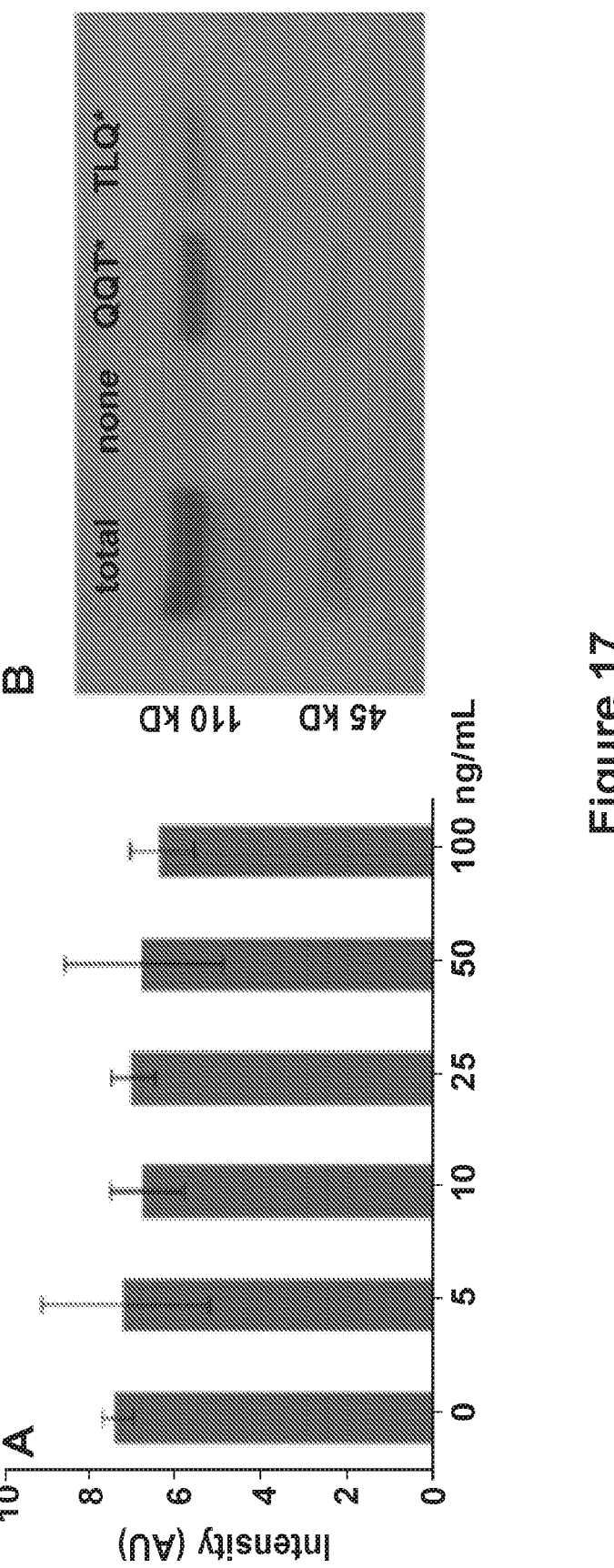

FIG. 17. Peptide characterization. A) Binding by QQT*-Cy5.5 to HT29 cells showed no change with addition of HGF using confocal microscopy. B) A strong band is seen for QQT* binding to mouse cMet-ECD versus that for TLQ* from pull-down assay. Key: total—20 µg mouse cMet-ECD with no EHS beads; none—EHS beads with no peptide; QQT*—target peptide immobilized on EHS beads; TLQ*—control peptide immobilized on EHS beads.

Figure 18:

FIG. 18. Western blots. Uncropped gels are shown for A) cMet knockdown with siRNA in HT29 cells (FIG. 2H), B) cMet expression in HT29 and SW480 cells (FIG. 10H), C) cMet expression in S114 and NIH3T3 cells (FIG. 11H), and D-H) detection of downstream cMet signaling in HT29 cells (FIG. 4) treated with HGF (25 ng/mL) or QQT*-Cy5.5 (5 or 10 µM), I) binding of QQT* to mouse cMet-ECD (FIG. 17). All of the blots are from the same gel, but were developed on different films.

Figure 19:
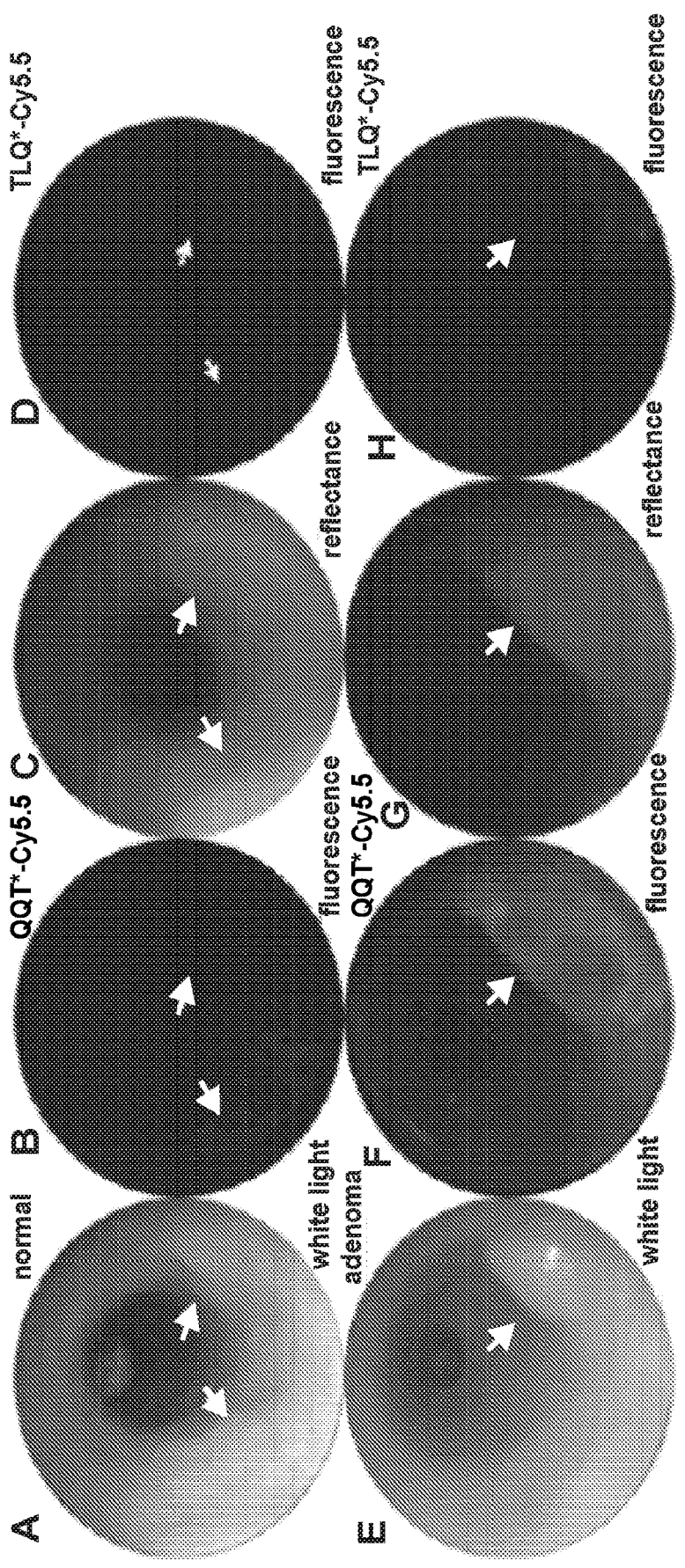
Figure 19:
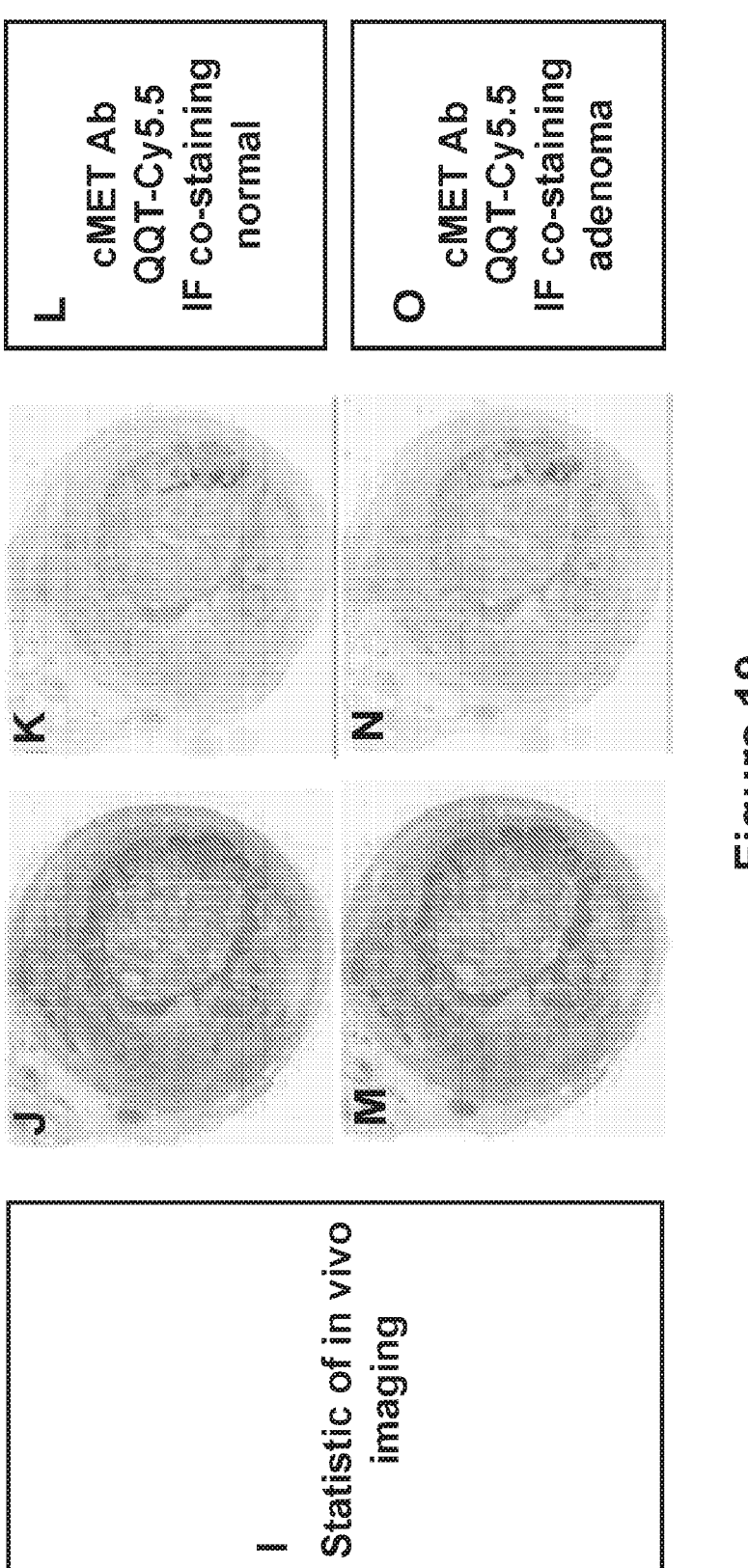

FIG. 19. Endoscopic imaging of human colon organoids in vivo. A) White light and B) reflectance images are shown for adenoma implanted in the colon of a NOD/SCID mouse. Fluorescence images collected following topical administration of C) QQT*-Cy5.5 showed strong intensity from adenoma while D) TLQ*-Cy5.5 provided minimal signal. E) White light and F) reflectance images are shown for SSA. Fluorescence image collected with G) QQT*-Cy5.5 showed strong intensity from SSA while H) TLQ*-Cy5.5 provided minimal signal. I) White light and J) reflectance images are shown for normal. Fluorescence images collected with G) QQT*-Cy5.5 and H) TLQ*-Cy5.5 showed minimal signal. The statistical mean T: B ratio for QQT*-Cy5.5 in vivo on SSA was found to be significantly greater than that on normal organoids 19L). H&E histology staining of normal and SSA organoids is shown in 16I, M. IHC staining of human specific hCytokeratin on the same slides demonstrated the successful transplantation of human organoids (16J, N). Using these tissue sections, IF co-staining of cMet antibody and QQT*-Cy5.5 showed minimal signal to normal colon 19K) while strong intensity to SSA organoids 16O).

DETAILED DESCRIPTION

Relatively small peptide-based fluorescent imaging probes specific for cancer biomarkers are expected to increase visualization of precancerous lesions with lower immunogenicity and quicker clearance. A few clinical studies have demonstrated that peptides can be used as diagnostic tool to guide tissue biopsy in the GI tract[27,28]. The relatively smaller size of peptides relative to antibodies allows the peptides to penetrate more easily into deep tissue, with minimal immunogenicity. Peptide-based imaging probes also exhibit high diversity and labeling flexibility at an affordable cost and with rapid binding kinetics. These benefits position peptides as agents well-suited for in vivo imaging and clinical use.

The disclosure provides a fluorescent-labeled peptide that is specific for cMet to detect premalignant dysplasia in CRC. The peptide was shown to detect, in vivo, pre-malignant colonic lesions that are flat in appearance and can easily be missed by colonoscopy with white light illumination. Using the biopanning technology with a phage display library, we identified a heptapeptide that specifically bound to the cMet extracellular domain. After labeling with near-infrared fluorescent dye Cy5.5, we topically administrated this peptide on mouse distal colon surface, which minimize toxicity and reduce the risk of binding to unexpected tissue. This peptide exhibited superior target-to-background (T/B) signal ratio relative to a scrambled control peptide. The functioning of the peptide as a probe or targeting ligand was examined in the experiments disclosed herein and the results demonstrate a peptide specific for cMet that is expected to be useful for endoscopic detection of pre-malignant lesions and for providing guidance in locating tissues for biopsy.

Phage display technology was used to biopan a linear hepta-peptide library against the extra-cellular domain (ECD) of cMet, and identified the heptapeptide sequence QQTNWSL (SEQ ID NO:1). We covalently linked the C-terminus of this linear monomer (black) with the near-infrared (NIR) fluorophore Cy5.5 (red) via a GGGSK (SEQ ID NO:2) linker (blue), hereafter QQT*-Cy5.5. The peptide is separated from the fluorophore to minimize effects of steric hindrance. Cy5.5 was chosen because it is less sensitive to hemoglobin absorption and tissue scattering, minimizes the effects of tissue autofluorescence, and provides the maximum light penetration depth. We achieved greater than 95% purity for both peptides with HPLC and measured an experimental mass-to-charge (m/z) ratio on mass spectrometry of 1827 which agrees with the expected value. We measured an apparent dissociation constant of $K_D$=57 nM for peptide binding to HT29 human colorectal adenocarcinoma cells. Also, we measured an apparent association time constant k=0.622 min-1 (1.61 min).

Overexpression of cMet is an early event in CRC neoplasia, making the detection of cMet expression level a promising method to identify premalignant dysplasia in CRC[20,21]. In addition, its location on the cell membrane makes cMet accessible to imaging agents, such as fluorescent targeting agents. Consistently, elevated cMet levels have been reported in a variety of cancer types, especially colorectal cancer. Various preclinical and clinical findings have confirmed that cMet is a promising target for molecular imaging, which allows the monitoring of abnormal alterations in real time and in vivo.

Disclosed herein is a NIR-labeled cMet targeted peptide for in vivo fluorescence imaging in a Cpc;Apc spontaneously developing polyp mouse model and in a human organoid-transplanted mouse model. QQTNWSL (SEQ ID NO:1) was selected by biopanning with phage display against the cMet extracellular domain. Specific binding to cMet was validated in vitro and ex vivo using standard assays, such as competition and cell binding assays. This peptide exhibited a high binding affinity of kd=57 nM, with binding occurring within 2 min (k=0.622 min-1), which is compatible with clinical use during colonoscopy. In a spontaneous mouse model of CRC, we demonstrated this peptide was shown to be capable of detecting flat and polyploid colonic adenomas in vivo that were diagnosed as low-grade dysplasia on pathology. To more accurately model real human physiology, a human organoid-transplanted mouse model was developed. Through orthotopic injection, this mouse model developed colon polyps derived from human organoids, which authentically recapitulate human CRC.

One of the important goals of advanced imaging techniques is to distinguish benign hyperplastic polyps from malignant lesions, such as serrated polyps, to avoid unnecessary costs and treatments[47]. The imaging results disclosed herein using the organoid-transplanted mouse model showed that the QQT*-Cy5.5 fluorescently labeled peptide bound to human adenoma and SSA, with minimal binding to normal organoids. IF staining of different subtypes of human proximal colon tissues with QQT*-Cy5.5 further confirmed this observation by showing that the fluorescently labeled peptide distinguished either adenoma or SSA from normal and HP with 88% sensitivity and 82% specificity with area-under-curve (AUC) of 0.94.

Molecular imaging probe-based antibodies targeted to cMet have been validated[48,49]. Although antibodies and antibody fragments can achieve high binding affinities, they are limited for diagnostics by slow binding kinetics, long half-lives, and increased background. Compared with antibodies, peptides are much safer and less costly, due to their lower molecular weight. Peptides have several advantages, such as favorable pharmacokinetic and tissue distribution patterns, higher permeability, lower toxicity, less immunogenicity, and easy accessibility for chemical modification[50]. Topical administration of peptides delivers the therapeutic directly to target tissue at risk of harboring disease in high concentrations to maximize binding interactions and to achieve high image contrast with little risk of toxicity. This approach avoids undesired biodistribution of the exogenous agent to other tissues characteristic of administration by, e.g., intravenous injection.

Recently, evidence has accumulated to suggest that cMet communicates with other cell-surface receptor tyrosine kinases (RTKs) and cell-surface proteins associated with tumor formation and progression in colorectal cancer, such as vascular endothelial growth factor receptor (VEGFR)[51,52] and the epidermal growth factor receptor (EGFR)[53,54]. Due to the complexity and heterogeneity of disease in a broad patient population, multiplexed imaging methods using multiple targets may prove beneficial[35,55].

Linkers and Polypeptides

As used herein, a "linker" is a sequence of amino acids, generally uncharged, located at a terminus of a peptide of the disclosure. In some embodiments, the linker sequence terminates with a lysine residue. Uncharged amino acids contemplated by the present disclosure include, but are not limited to, glycine, serine, cysteine, threonine, histidine, tyrosine, asparagine, and glutamine.

In some embodiments, the presence of a linker results in at least a 1% increase in detectable binding of a reagent of the disclosure to dysplastic colon cells or cancerous colon cells compared to the detectable binding of the reagent in the absence of the linker. In various aspects, the increase in detectable binding is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 100-fold or more.

The term "peptide" refers to molecules of 2 to 50 amino acids, molecules of 3 to 20 amino acids, and those of 6 to 15 amino acids. Peptides and linkers as contemplated by the invention may be 5 amino acids in length. In various aspects, a polypeptide or linker may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length.

Exemplary peptides are, in various aspects, randomly generated by methods known in the art, carried in a polypeptide library (for example and without limitation, a phage display library), derived by digestion of proteins, or chemically synthesized. Peptides exemplified in the present disclosure can be obtained using techniques of phage display, a powerful combinatorial method that uses recombinant DNA technology to generate a complex library of polypeptides for selection by preferential binding to cell surface targets [Scott et al., *Science*, 249:386-390 (1990)]. The protein coat of bacteriophage, such as the filamentous M13 or icosahedral T7, is genetically engineered to express a very large number (greater than 109) of different polypeptides with unique sequences to achieve affinity binding [Cwirla et al., *Proc. Natl. Acad. Sci. USA*, 87:6378-6382 (1990)]. Selection is then performed by biopanning the phage library against cultured cells and tissues that over-express the target. The DNA sequences of these candidate phage are then recovered and used to synthesize the polypeptide [Pasqualini et al., *Nature*, 380:364-366 (1996)]. The polypeptides that preferentially bind to dysplastic mucosa are optionally labeled with fluorescence dyes, including but not limited to, FITC, Cy 5.5, Cy 7, and Li-Cor.

Peptides include D and L forms, either purified or in a mixture of the two forms. Also contemplated by the present disclosure are peptides that compete with peptides of the invention for binding to colon cells.

It will be understood that peptides and linkers of the invention optionally incorporate modifications known in the art and that the location and number of such modifications are varied to achieve an optimal effect.

Detectable Markers

As used herein, a "detectable marker" is any label that can be used to identify the binding of a composition of the disclosure to tissue of the intestine such as colon tissue. Non-limiting examples of detectable markers are fluorophores, chemical or protein tags that enable the visualization of a polypeptide. Visualization in certain aspects is carried out with the naked eye, or a device (for example and without limitation, an endoscope) and may also involve an alternate light or energy source.

Fluorophores, chemical and protein tags that are contemplated for use in the invention include but are not limited to FITC, Cy 5.5, Cy 7, Li-Cor, a radiolabel, biotin, luciferase, 1,8-ANS (1-Anilinonaphthalene-8-sulfonic acid), 1-Anilinonaphthalene-8-sulfonic acid (1,8-ANS), 5-(and-6)-Carboxy-2', 7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, eYFP (Enhanced Yellow Fluorescent Protein), FDA, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, Fura-2, GFP (S65T), HcRed, Indo-1 Ca2+, Indo-1, Ca free, Indo-1, Ca saturated, JC-1, JC-1 pH 8.2, Lissamine rhodamine, Lucifer Yellow, CH, Magnesium Green, Magnesium Green Mg2+, Magnesium Orange, Marina Blue, mBanana, mCherry, mHoneydew, mOrange, mPlum, mRFP, mStrawberry, mTangerine, NBD-X, NBD-X, MeOH, NeuroTrace 500/525, green fluorescent Nissl stain-RNA, Nile Blue, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 7.0, Rhodol Green antibody conjugate pH 8.0, Sapphire, SBFI-Na$^+$, Sodium Green Na$^+$, Sulforhodamine 101, Tetramethylrhodamine antibody conjugate pH 8.0, Tetramethylrhodamine dextran pH 7.0, and Texas Red-X antibody conjugate pH 7.2.

Non-limiting examples of chemical tags contemplated by the invention include radiolabels. For example and without limitation, radiolabels that contemplated in the compositions and methods of the present disclosure include $^{11}$C, $^{13}$N, $^{15}$O, $^{18}$F, $^{32}$P, $^{52}$Fe, $^{62}$Cu, $^{64}$Cu, $^{67}$Cu, $^{67}$Ga, $^{68}$Ga, $^{86}$Y, $^{89}$Zr, $^{90}$Y, $^{94m}$Tc, $^{94}$Tc, $^{95}$Tc, $^{99m}$Tc, $^{103}$Pd, $^{105}$Rh, $^{109}$Pd, $^{111}$Ag, $^{111}$In, $^{123}$I, $^{124}$I, $^{125}$I, $^{131}$I, $^{140}$La, $^{149}$Pm, $^{153}$Sm, $^{154-159}$Gd, $^{165}$Dy, $^{166}$Dy, $^{166}$Ho, $^{169}$Yb, $^{175}$Yb, $^{175}$Lu, $^{177}$Lu, $^{186}$Re, $^{188}$Re, $^{192}$, $^{198}$Au, $^{199}$Au, and $^{212}$Bi.

A worker of ordinary skill in the art will appreciate that there are many such detectable markers that can be used to visualize a composition of the disclosure, in vitro, in vivo or ex vivo.

Therapeutic Moieties

Therapeutic moieties contemplated by the invention include, but are not limited to, polypeptides or peptides, small molecules, therapeutic agents, chemotherapeutic agents, or combinations thereof.

The term "small molecule", as used herein, refers to a chemical compound, for instance a peptidomimetic or oligonucleotide that may optionally be derivatized, or any other low molecular weight organic compound, either natural or synthetic.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

In some aspects, the therapeutic moiety is a protein therapeutic. Protein therapeutics include, without limitation, cellular or circulating proteins as well as fragments and derivatives thereof. Still other therapeutic moieties include polynucleotides, including without limitation, protein coding polynucleotides, polynucleotides encoding regulatory polynucleotides, and/or polynucleotides which are regulatory in themselves. Optionally, the compositions comprise a combination of the compounds described herein.

In various aspects, protein therapeutics include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neurotrophic factor, ciliary neurotrophic factor receptor, cytokine-induced neutrophil chemotactic factor 1, cytokine-induced neutrophil, chemotactic factor 2α, cytokine-induced neutrophil chemotactic factor 2β,β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neurotrophic factor receptor α1, glial cell line-derived neurotrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Therapeutic moieties also include, in various embodiments, chemotherapeutic agents. A chemotherapeutic agent contemplated for use in a reagent of the invention includes, without limitation, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as triethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; anti-estrogen such as tamoxifen; androgens including testosterone propionate and fluoxymesterone/equivalents; anti-androgens such as flutamide, gonadotropin-releasing hormone analogs and leuprolide; and non-steroidal anti-androgens such as flutamide.

Dosages of the therapeutic moiety or reagent provided are administered as a dose measured in, for example, mg/kg. Contemplated mg/kg doses of the disclosed therapeutics include about 1 mg/kg to about 60 mg/kg. Specific ranges of doses in mg/kg include about 1 mg/kg to about 20 mg/kg, about 5 mg/kg to about 20 mg/kg, about 10 mg/kg to about 20 mg/kg, about 25 mg/kg to about 50 mg/kg, and about 30 mg/kg to about 60 mg/kg. The precise effective amount for a subject will depend upon the subject's body weight, size, general health, the nature and extent of any condition, and the therapeutic or combination of therapeutics selected for administration. Therapeutically effective amounts for a given situation can be determined by routine experimentation that is within the skill and judgment of the clinician.

"Effective amount" as used herein refers to an amount of a reagent of the invention sufficient to visualize the identified disease or condition, or to exhibit a detectable therapeutic or inhibitory effect. The effect is detected by, for example, an improvement in clinical condition or reduction in symptoms. The precise effective amount for a subject will depend upon the subject's body weight, size, general health, the nature and extent of the condition; and the therapeutic or combination of therapeutics selected for administration. Therapeutically effective amounts for a given situation can be determined by routine experimentation that is within the skill and judgment of the clinician.

Visualization of Reagents

Visualization of binding to colon cells is by any means known to those of ordinary skill in the art. As discussed herein, visualization is, for example and without limitation, in vivo, in vitro, ex vivo, or in situ visualization.

In one embodiment, visualization is performed via imaging and may be performed with a wide-area endoscope (Olympus Corporation, Tokyo, Japan) that is designed specifically to collect fluorescence images with high spatial resolution over large mucosal surface areas on the macroscopic scale (millimeters to centimeters). This capability is needed to rapidly screen large surface areas such as that found in the distal esophagus during endoscopy to localize regions suspicious for disease [Wang et al., Gastrointestinal Endoscopy 1999; 49:447-55]. This technique has been adapted for fluorescence detection, and is compatible with dye-labeled probes. This instrument can image in three different modes, including white light (WL), narrow band imaging (NBI), and fluorescence imaging. Narrow-band imaging is a new technology that represents a variation of conventional white light illumination by altering the spectrum with optical filters to restrict or narrow the range of wavelengths.

The method enhances contrast in the endoscopic images to provide more visual details of the esophageal mucosa by tuning the light to maximize absorption of hemoglobin present in the vasculature of regions of intestinal metaplasia. The WL and NBI images are collected by the central objective lens, and the fluorescence image is collected by a second objective lens located near the periphery. There is a distance of approximately 3 mm between the centers of the white light and fluorescence objectives that results in only a slight misregistration of the two images. Furthermore, there is an air/water nozzle that removes debris from the objective lenses, and a 2.8 mm diameter instrument channel that can be used to deliver biopsy forceps. The objectives are forward viewing and have a field of view (FOV), defined by maximum angle of illumination, of 140 degrees. The WL/NBI imaging modes have a depth of field (DOF), defined by range of distances between the distal end of the endoscope to the mucosal surface whereby the image is in focus, of 7 to 100 mm, and that for fluorescence is 5 to 100 mm. The transverse resolution measured at a distance of 10 mm from the mucosa for WL/NBI is 15 m and for fluorescence is m. A xenon light source provides the illumination for all three modes, which is determined by a filter wheel located in the image processor. Illumination for all three modes of imaging is delivered through the two fiber light guides. In the WL mode, the full visible spectrum (400 to 700 nm) is provided, while in the NBI mode, a filter wheel narrows the spectral bands in the red, green, and blue regime. In the fluorescence mode, a second filter wheel enters the illumination path, and provides fluorescence excitation in the 395 to 475 nm spectral band. In addition, illumination from 525 to 575 nm provides reflected light in the green spectral regime centered at 550 nm. The fluorescence image is collected by the peripherally located CCD detector that has a 490-625 nm band pass filter for blocking the excitation light. Normal mucosa emits bright autofluorescence, thus the composite color appears as bright green. Because the increased vasculature in neoplastic mucosa absorbs autofluorescence, it appears with decreased intensity.

This medical endoscope can be used to collect images after reagent administration and incubation from colon with 1) white light, 2) narrow band, and fluorescence. After entering the colon, a 5 second video is collected and digitized in the white light and narrow band imaging modes. The imaging in this mode is used to assess the spatial extent of the intestinal metaplasia for comprehensive evaluation of polypeptide binding. Then, approximately 3 ml of the fluorescence-labeled peptide is administered topically at a concentration of 10 μM to the colon using a mist spray catheter being careful to cover the full extent of the mucosa. Amounts of reagent of the invention can be determined by one of ordinary skill in the art.

In some embodiments where the detectable label is a radiolabel, the radiolabel is detected by nuclear imaging. Nuclear imaging is understood in the art to be a method of producing images by detecting radiation from different parts of the body after a radioactive tracer material is administered. The images are recorded on computer and on film.

Other methods according to the disclosure involve the acquisition of a tissue sample from a patient. The tissue sample is selected from the group consisting of a tissue or organ of said patient.

Formulations

In various aspects, compositions of the invention are formulated with pharmaceutically acceptable excipients such as carriers, solvents, stabilizers, adjuvants, diluents, and the like, depending upon the particular mode of administration and dosage form. The compositions are generally formulated to achieve a physiologically compatible pH, and range from a pH of about 3 to a pH of about 11, or about pH 3 to about pH 7, depending on the formulation and route of administration. In alternative embodiments, the pH is adjusted to a range from about pH 5.0 to about pH 8. In various aspects, the compositions comprise a therapeutically effective amount of at least one compound as described herein, together with one or more pharmaceutically acceptable excipients. Optionally, the compositions comprise a combination of the compounds described herein, or may include a second active ingredient useful in the treatment or prevention of bacterial growth (for example and without limitation, anti-bacterial or anti-microbial agents), or may include a combination of reagents according to the disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

The following examples are presented by way of illustration and are not intended to limit the scope of the subject matter disclosed herein.

EXAMPLES

Example 1

Cells Lines, Culture Media and Chemicals

Human CRC cell lines HT29, SW480, CCD841 and mouse embryonic fibroblast cell line NIH 3T3 were obtained from the American Type Culture Collection (ATCC, Manassas, VA). The S114 cell line comprised NIH 3T3 cells transformed with human HGF/SF and Met and expressed cMet. We used McCoy's 5A Medium (Gibco) for culturing HT29 cells and Dulbecco's Modified Eagle Medium (Gibco) was used to culture SW480, NIH3T3 and S114 cells. Eagle's Minimum Essential Medium (Lonza) was used for CCD841 cells. All cells were cultured at 37° C. in 5% $CO_2$, and supplemented with 10% fetal bovine serum (FBS). The cells were passaged using 0.25% trypsin containing EDTA (Mediatech, Manassas, VA). Cell numbers were quantitated on a hemocytometer. Peptide synthesis reagents were obtained from Anaspec (Anaspec, Fremont, CA) or AAPPTEC (AAPPTEC, Louisville, KY), were of the highest grade available (>99% purity), and were used without further purification. Solvents and other chemical reagents were purchased from Sigma-Aldrich (St. Louis, MO) unless otherwise noted.

Peptide Specific for cMet

A phage display library of heptapeptides (Ph.D.-7 New England Biolabs) was used to biopanagainst the extracellular domain of purified cMet protein, i.e., cMet-ECD (10692-H08H, Sino Biological Inc.)[32]. Candidate phages with the highest enrichment were selected for further evaluation. Reactivity to HT29 cells was assessed using enzyme-linked immunosorbent assay (ELISA). Binding interactions between the candidate peptides and cMet were assessed with non-intact structures 1UX3 and 2UZX using Pepsite software[55]. Using the above protocol, the phage containing the QQTNWSL (SEQ ID NO:1) (QQT*) peptide was enriched after 4 rounds of biopanning. A random scrambled sequence, i.e., TLQWNQS (SEQ ID NO:3) (TLQ*), was used as a control. Peptides were synthesized using standard Fmoc-mediated solid-phase chemistry[33], labeled the C-terminus of peptides with NIR dye Cy5.5 (Lumiprobe, Hallandale Beach, FL) via a 5-amino-acid (GGGSK; SEQ ID NO:2) linker. Synthesis of both peptides was performed with a PS3 automatic synthesizer (Protein Technologies Inc., Tucson, AZ). Fmoc- and Boc-protected L-amino acids were used and synthesis was assembled on rink amide MBHA resin. The C-terminal lysine was incorporated as Fmoc-Lys (ivDde)—OH, and the N-terminal amino acid was incorporated with Boc protection to avoid unwanted Fmoc removal during deprotection of the ivDde moiety prior to fluorophore labeling. Upon completion of synthesis, the ivDde side chain protecting group was removed with 5% hydrazine in DMF (3×10 min) with continuous agitation at room temperature (RT), and then the resin was transferred to a reaction vessel for manual labeling with dye. The resin was washed with DMF and DCM for 3×1 min. The protected resin-bound peptide was incubated overnight with the Cy5.5-NHS ester in the presence of DIEA and incubated for 24-48 hours with agitation at RT, and the completion of the reaction was monitored by a qualitative Ninhydrin test. The peptide was then cleaved from the resin with chilled trifluoroacetic acid (TFA):triisopropylisilane:water (9.5:0.25:0.25, vol/vol/vol) for 4 hours with agitation in the dark at RT. After separating the peptide from the resin, the filtrate was evaporated with $N_2$ gas followed by precipitation with chilled diethyl ether in an overnight incubation at −20° C. The precipitate was centrifuged at 3000 rpm for 5 min and washed with diethyl ether 3 times. The crude peptides were suspended in 1:1 acetonitrile:$H_2O$ (v/v) and purified via high-performance liquid chromatography (Waters, Milford, MA) with a C18 column using a water (0.1% TFA)-acetonitrile (0.1% TFA) gradient. The final purity of the peptides was confirmed by analytical C18-column. Mass Spectrometry (MALDI-TOF, Bruker AutoFlex Speed) was used to measure the mass-to-charge (m/z) ratios of the products.

Spectral Measurements

The absorbance spectra of peptides were measured using a UV-Vis spectrophotometer (NanoDrop 2000, Thermo Scientific), and the fluorescence emission was collected with a fiber-coupled spectrophotometer (Ocean Optics) using a diode-pumped solid state laser (Technica Laser Inc.) with excitation at λex=671 nm. The spectra were plotted with Origin 6.1 software (OriginLab Corp).

Confocal Fluorescence Microscopy

HT29, SW480, S114 and NIH3T3 cells were inoculated in 12-well cell culture plates with circle glass coverslips to about 80% confluence. The cells were blocked with 1×PBS plus 2% BSA for 1 hour at 4° C., then were incubated with 5 μM peptides for 10 min at RT in the dark, washed thrice, and fixed with 4% PFA for 5 min, washed with 1×PBS, then mounted on glass slides with ProLong Gold reagent containing DAPI (Invitrogen, Waltham, MA). As positive control, after blocking with 2% BSA for 1 hour at 4° C., A 1:3000 dilution of primary monoclonal rabbit anti-cMet antibody (Cell Signaling Technology, #8198) was incubated with cells overnight at 4° C. Afterward, the cells were washed thrice with 1×PBS and further incubated with a 1:500 dilution of AF488-labeled secondary goat ant-rabbit immunoglobulin G antibody (Life Technologies, #A-11029) for 1 hour at RT, washed thrice, and then mounted on glass slides with ProLong Gold reagent containing DAPI. Confocal fluorescence images were collected using a 63× oil-immersion objective (Leica SP5 Inverted 2-Photon FLIM Confocal). Fluorescence intensities from five cells in two independent images were quantified using custom Matlab (Mathworks) software.

Downregulation of cMet with siRNA

We knocked down cMet protein levels with siRNAs and then evaluated the binding of QQT*-Cy5.5 and TLQ*-Cy5.5 to the surface of si-cMet-transfected HT29 cells to validate specific peptide binding. We used siRNA1 (SASI_Hs01_00133002, Sigma) for HT29, siRNA2 (SASI_WI_00000001, Sigma) for S114, and MISSION® siRNA #1 Universal Negative Control (SIC001, Sigma) for a negative control. We transfected cells with Lipofectamine 2000 (11668027, Invitrogen) per manufacturer instructions. Knockdown of cMet was confirmed by Western blot (FIG. 18). The cells were incubated with 5 μM peptide for 5 min at RT (i.e., room temperature), and then fixed and mounted on glass slides with ProLong Gold reagent containing DAPI, as previous described. As positive control, a 1:3000 dilution of primary monoclonal rabbit anti-cMet antibody (Cell Signaling Technology, #8198) was incubated with cells, fixed and mounted on glass slides with ProLong Gold reagent containing DAPI. Confocal fluorescence images were collected using a 63× oil-immersion objective (Leica SP5 Inverted 2-Photon FLIM Confocal).

Competition for Peptide Binding

We used a competition assay between labeled QQT*-Cy5.5 and either unlabeled QQT* or recombinant human hepatocyte growth factor (HGF, 194-HG-005, R&D) to validate the specific binding of QQT**-Cy5.5 to HT29 cells. Approximately $10^3$ HT29 cells were grown to about 70% confluence on coverslips in triplicate. Unlabeled QQT* and either TLQ* peptide at 0, 25, 50, 100, 200 and 400 µM, or HGF at 0, 5, 10, 25, 50 or 100 ng/mL, were first added and incubated with the cells for 30 min (i.e., minutes) at 4° C. The cells were washed with 1×PBS three times and then incubated with 5 µM QQT*-Cy5.5 for another 30 min at 4° C. The cells were washed three times with 1×PBS and then fixed with 4% PFA for 10 min. The cells were washed with 1×PBS and mounted with ProLong Gold reagent containing DAPI (Invitrogen). Confocal fluorescence images were collected at each concentration using a 63× objective (Leica SP5 Inverted 2-Photon FLIM Confocal), and intensities from five cells in three independent images were quantified using custom Matlab (Mathworks, Natick, MA) software.

Effect of Peptide on Cell Signaling

HT29 cells were treated with serum-free medium overnight for starvation before incubation with hHGF (hHGF, 294-HG-005, R&D) or peptides. Recombinant Human HGF Protein was added to HT29 cells at concentrations of 25 ng/ml for 10, 30, or 120 min in separate wells. QQT*-Cy5.5 and TLQ*-Cy5.5 were added at concentrations of 5 or 100 µM for 10, 30, and 120 min. Peptides were added at concentrations of 5 and 100 µM for 10, 30, or 120 min. Cells were then washed with 1×PBS and lysed with Pierce RIPA buffer containing Halt Phosphatase Inhibitor Cocktail (Thermo Fisher) and Halt Protease Inhibitor Cocktail (Thermo Fisher). Protein contents were quantified by Bicinchoninic Acid Assay (BCA). Anti-cMet antibody (Cell Signaling, #8198), phospho-cMet (Tyr1234/1235) antibody (Cell Signaling, #3077), anti-AKT antibody (Cell Signaling, #4691), anti-phospho-AKT antibody (Cell Signaling, #9271), anti-ERK1/2 antibody (Abcam, #ab17942), anti-phospho-ERK1/2 antibody (Abcam, #ab50011), and anti-tubulin antibody (Invitrogen, #32-2600) were used per manufacturer's instructions.

An alamar blue assay was performed using HT29 and CCD841 cells. After culturing in serum free media overnight, about $3\times10^3$ cells were seeded per well in serum free media in 96 well plates at a final volume of 100 µL per well. The cells were incubated with either HGF (25 ng/mL) or peptide (5 and 10 µM) at 37° C. for 48 hours. Alamar blue reagent (10 µL) was added in amounts equal to 10% of the volume in the well, and incubated at 37° C. for 4 hours. Fluorescence with excitation at λex=530-560 nm, and emission at λex=590 nm, was measured.

Characterization of Peptide Binding

We assessed the binding affinity of QQT*-Cy5.5 to HT29 cells by measuring the apparent dissociation constant. HT29 cells were blocked with 0.5% BSA, and then approximately $10^5$ cells were incubated with QQT*-Cy5.5 at concentrations of 0, 10, 25, 50, 75, 100, 125, 150, or 200 nmol/L for 1 hour at 4° C. Cells then were washed 3 times with 1×PBS containing 0.5% BSA to remove unbound peptides before analysis with flow cytometry (FACS Canto; BD Biosciences, San Jose, CA). Sample means were used to calculate the equilibrium dissociation constant $K_D$ using nonlinear regression analysis with Origin 6.1 data analysis software (OriginLab, Northampton, MA). $K_D=1/K_A$ was calculated by performing a least-squares fit of the data to the nonlinear equation $I[X]=(I_0+I_{max}k_a[X])/(I_0+k_a[X])$. $I_0$ and $I_{max}$ are the initial and maximum fluorescence intensities, corresponding to no peptide and peptide saturation, respectively, and [X] represents the concentration of the bound peptide.[34]

The time scale of QQT*-Cy5.5 binding to HT29 cells was assessed by measuring the apparent association time constant k. HT29 cells were blocked with 0.5% BSA, and then approximately $10^5$ cells were incubated with 5 µM QQT*-Cy5.5 for time intervals ranging from 0 to 20 min at 4° C. Cells then were washed 3 times with cold 1×PBS containing 0.5% BSA to remove unbound peptides. After centrifugation, the cells were fixed with 4% PFA for 30 min at 4° C. before analysis with flow cytometry. The median fluorescence intensity (y) at the various time points (t) was taken as a ratio with that of HT29 cells without the addition of peptide using the Flowjo software (LLC, Ashland, OR). The rate constant k was calculated by fitting the data to a first-order kinetics model y (t)=$I_{max}$ [1−exp(−kt)] where $I_{max}$ is the maximum value, using the Prism 5.0 software (GraphPad, La Jolla, CA).

Interactions between peptide and mouse cMet were evaluated using a pull-down assay (Paul et al., Methods 54:387-395 (2011)). Peptides were immobilized on EHS active beads (17-0906-01, GE), and incubated with purified mouse cMet-ECD protein (50622-M08H, Sino Biological). After washing, bound proteins were detected by Western blot (FIG. 18).

Organoid Specimens

The information about patient specimens are listed in Table 1. The normal specimen (#87) in this study was derived from the tissue of a deceased donor; while the adenoma organoids were derived from biopsied large adenoma: #245 (sessile serrated); #590 (tubular); #584 (tubular 20 mm); and #236 (FAP).

To authenticate specimens, short tandem repeat (STR) analysis was employed to identify human genomic DNA for 15 tetranucleotide repeat loci (AMPFLSTR Identifier Plus Assay, Applied Biosystems; University of Michigan DNA Sequencing Core), in addition, the amelogenin gender determination marker was run on the 3730XL Genetic Analyzer (Applied Biosystems). Cultures were frequently tested for *mycoplasma* contamination with the Lonza MycoAlert Kit (service of the UMICH Transgenic Animal Model Core).

TABLE 1

Patient-derived colon normal and adenoma organoids. A targeted colorectal cancer DNA sequencing panel was used to determine the presence of variants for 71 different oncogenes and tumor suppressor genes often mutated in colorectal cancers. Stop codon (*); frame shift (FS).

| Neoplasm | ID | Sex & Age | Location | Variations |
|---|---|---|---|---|
| Normal colon | | 87 | | M (ages 21); ascending |
| Adenoma: Sessile serrated (20 mm) | 245 | F | 54 ascending | BRAF Val600Glu, WBSCR17 Ser432Ser |
| Adenoma (35 mm) | 590 | F | 58 ascending | BUB1B Arg550*, FLCN His429fs, MLH1 Lys443fs, MSH3 Lys381fs, PALB2 Met296fs, TCERG1 Arg889fs, CTNNA1 Met826Thr, CTNNB1 Ser45Phe, MAP2K4 Val127Ala, MLH3 Pro564Ser, PIK3R1 Arg188Cys |
| Adenoma: FAP (2 mm) | 236 | F | 26 ascending | APC Thr1556fs, APC Leu143fs, MLH3 E624Q |
| Adenoma (20 mm) | 584 | M | 61 ascending | APC Thr1556fs, KRAS Ala146Val, MET Arg988Cys, PMS2 Gly29Ala, TP53 Arg267Trp, EP300 Asp1579Asn |

Organoid Culture

Human organoid cultures were previously established from normal and adenomatous tissues[36-38] and provided by the Translational Tissue Modeling Laboratory (TTML; University of Michigan).

Cultures were grown in Matrigel (diluted to 8 mg/mL with growth media; Corning, #354234) in 6-well tissue culture plates (USA Scientific CytoOne, #CC7682-7506). Cultures were passaged by triturating and dissociating the Matrigel in cold Dulbecco's phosphate-buffered saline (DPBS), centrifuging at 300×g, and plating the first day with 2.5 µM CHIR99021 (Tocris; 4423), a highly selective GSK3 inhibitor, and 10 µM Y27632 (Tocris; TB1254-GMP/10), a highly selective p160ROCK inhibitor.

The normal (#87) and sessile serrated (#245) organoids were cultured in LWRN Complete medium containing 50% L-WRN conditioned medium (source of Wnt3a, R-spondin-3 and Noggin)[39], advanced DMEM/F-12 (Gibco, 12634028), N-2 media supplement (Gibco; Ser. No. 17/502, 048), B-27 supplement minus vitamin A (Gibco; Ser. No. 12/587,010), 1 mM N-Acetyl-L-cysteine (Sigma-Aldrich, A9165), 2 mM GlutaMax (Gibco, #35050-061), 10 mM HEPES (Gibco, #15630080), 50 units/mL penicillin, 0.05 mg/mL streptomycin (Gibco, #15070063), 50 µg/ml Primocin (InvivoGen; ##ant-pm-1), 100 ng EGF/mL (R&D Systems, Inc., 236-EG), 10 µM SB202190 (Sigma-Aldrich; S7067), 500 nM A83-01 (R&D Tocris, #2939), and 10 µM Y27632 (Tocris; TB1254-GMP/10). The FAP adenoma (#236) was cultured in LWRN Complete medium without SB 202190.

The tubular adenoma organoid (#590) was cultured in Stemline Complete medium, containing Stemline™ Keratinocyte Medium II (Sigma 50196) and supplemented with Stemline Growth Supplement (Sigma S9945), 2 mM GlutaMax, 4 mM L-glutamine, and 50 µg/ml Primocin. Prior to harvest for transplantation, the #590 cultures were treated with 5 µM Y27632 for 18 hours. The tubular adenoma organoid #584 was cultured in 50% of the above Stemline complete medium and 50% of the above LWRN complete medium.

Cultures were harvested from Matrigel in cold DPBS, triturated 30× with a 1 mL pipette tip, and centrifuged at 300×g for 3 min at 4° C. The organoid pellet was resuspended in 10 mL cold DPBS and mechanically disassociated with the gentle MACS Octo Dissociator (Miltenyi Biotec; 130-096-427) using the programs h_Tumor_01.01 followed by m_Lung-01.01. The organoid fragments were further dissociated by 20× pipetting with a 1 mL pipette tip. Large fragments were removed over a 100 µm BSA-coated cell strainer (Corning, DL 352360). A slow centrifugation at 100×g was done to reduce single cell content. The cell aggregates were resuspended in cold DPBS supplemented with 5% Matrigel and 10 µM Y27632. All plasticware, including gentle MACS C-tubes (Miltenyi; 130-093-237), were treated with 0.1% BSA in DPBS to reduce adherence of organoids.

Organoid Transplant

Acute colitis was induced in 8-week-old NOD.Cg-Prkdcscid Il2rgtm1Wjl/SzJ mice (005557, The Jackson Laboratory)[40,41] by feeding them with 3.0% DSS (molecular weight 40,000; Cat #AAJ6360622; Alfa Aesar) dissolved in drinking water for 5 days (d). At 6 d, the donor organoids were released from the type I collagen gel, dissociated by EDTA, and washed with BSA-containing PBS as with the passage procedure. Approximately 2.5-5E5 cell aggregates in 200 µL were transplanted per mouse as previously described[42,43]. Organoids were instilled into colonic lumen as a suspension by using a syringe and a thin flexible catheter 4 cm in length and 2 mm in diameter. The anal verge was glued for 6 hours after infusion to prevent luminal contents from being excreted immediately, then glue were removed by Ethanol. Mice were maintained as usual after the transplantation. The mice were housed in pathogen-free conditions and supplied water ad libitum under controlled conditions of humidity (50±10%), light (12/12 hour light/dark cycle) and temperature (25° C.). Anesthesia was induced and maintained via a nose cone with inhaled isoflurane mixed with oxygen at a concentration of 2-4% at a flow rate of about 0.5 L/min. Organoid imaging was performed 3 weeks after transplantation.

CPC;Apc Mouse Model

A CPC;Apc mouse model that can develop spontaneous adenomas in distal colon epithelium[44] was also used. Under the control of the Cdx2 promoter (CDX2P-9.5NLS-Cre), Cre recombinase can sporadically delete the adenomatous polyposis coli (APC) allele, resulting in polyploid colonic adenomas or flat lesions. We collected images from mice (n=8) that ranged in age from 7 to 10 months.

In Vivo Imaging with Peptide

In vivo imaging was performed with approval of the University of Michigan Committee on the Use and Care of Animals. CPC;Apc mice were used for in vivo imaging. This mouse line was genetically engineered to sporadically delete an adenomatous polyposis coli (APC) allele under control of a Cdx2 promoter (CDX2P-9.5NLS-Cre) to spontaneously form either flat or polyploid adenomas in the distal colon (Hinoi et al., Cancer Res 67:9721-9730 (2007)). Mice were housed in pathogen-free conditions and supplied water ad libitum under controlled conditions of humidity (50±10%), light (12/12 hour light/dark cycle) and temperature (25° C.). Prior to imaging, the mice were fasted for 4-6 hours. Anesthesia was induced and maintained via a nose cone with inhaled isoflurane mixed with oxygen at a concentration of 2-4% at a flow rate of 0.5 L/min.

A rigid small animal endoscope (Karl Sorz Veterinary Endoscopy) was inserted into the rectum (Liu et al., Gut 62:395-403 (2013)) and used to image the distal colon[45]. Mucus and debris in the distal colon were removed by vigorously rinsing with warm tap water 3×. White-light illumination was applied first to identify the presence of adenomas. The distance between the endoscope tip and the anus, and the clockwise location of polyps, were recorded. QQT*-Cy5.5 solution (100 μM, 1.5 mL) was topically delivered into the distal colon through the instrument channel (3 Fr). After 5 min for incubation, unbound peptides, stool and debris were rinsed away with warm tap water 3× prior to image collection. After 3 days, clearance of the signal from QQT*-Cy5.5 was confirmed endoscopically, and then the same mice were imaged using TLQ*-Cy5.5 for control. A ratio of the fluorescence and reflectance images was determined to correct for differences in distance and geometry over the image field-of-view (FOV) (Joshi et al., Endoscopy 48:A1-A13 (2016)). A total of 3 independent regions with dimensions of 20×20 μm² were identified randomly from the location of the adenoma (target) and from adjacent normal colonic mucosa (background).

The mean fluorescence intensity was used to calculate the target-to-background (T/B) ratios. Images were processed and analyzed using custom software in Matlab (Mathworks) (Joshi et al., Gastroenterology 152:1002-1013 e1009 (2017)). Matlab software was used to quantify the fluorescence intensity. The fluorescence intensity of regions of interest (ROI) was corrected by taking the ratio of fluorescence to reflectance, the fluorescence of interested region was taken as target (T), and adjacent mouse normal colon region with equal area was picked for use as background (B)[46]. Streams that showed minimum motion artifact and absence of debris (stool, mucus) were selected for image quantification. Individual frames were exported using the custom Matlab software.

Ex Vivo Validation of High Expression of cMet in Mouse Colonic Neoplasia

After imaging was completed, the mice were euthanized. The colon was resected and divided longitudinally, the colon was excised, flushed with PBS, and opened longitudinally for imaging with the NIR fluorescence imaging system (Pearl®, LI-COR Biosciences). Images were collected with 85 m resolution using λex=685 nm and λem=720 nm. Images were analyzed with custom software (Image Studio, Li-Cor Biosciences). The normal colon region with an equal area adjacent to the polyps was used to measure background. Prism software (v6.02, GraphPad) was used to plot data. Increased cMet Expression in CPC;Apc Mouse Colonic Adenoma and Human Proximal Colonic Neoplasia with IHC Serial formalin-fixed sections were prepared with 10 m thickness, deparaffinized, and antigen retrieval accomplished using standard methods. Briefly, sections were incubated in xylene for 3 min 3 times, washed with 100% ethanol for 2 min 2 times, and washed with 95% ethanol for 2 min 2 times. Sections were incubated in $dH_2O$ for 5 min 2 times for rehydration. Antigen unmasking was performed in boiled 10 mM 1× pH6.0 citric acid buffer for 10 min. After cooling at room temperature (RT) for 20-30 min, the sections were washed in $dH_2O$ for 2 min 3 times. The sections were incubated in 3% $H_2O_2$ for 10 min to block endogenous peroxidase activity. The sections were washed in $dH_2O$ for 5 min three times and in phosphate-buffered saline with Tween 20 (PBST) for 5 min. Blocking was performed with 10% normal goat serum or DAKO protein blocking agent (X0909, DAKO) for 45 min at RT. The sections were incubated overnight with 1:100 dilution of monoclonal rabbit anti-cMet antibody (Abcam, EP1454Y, ab51067) containing 2.5% normal goat serum at 4° C. and washed in 0.1% TBST for 5 min 3 times. A 1:200 dilution of secondary goat anti-rabbit antibody (Abcam, ab150077) was applied to each section and incubated for 30 min at RT. Controls were prepared using the same method but without addition of the primary anti-cMet antibody. Secondary antibody was removed by washing in 0.1% TBST for 5 min 3 times. Sections were then incubated in premixed Elite Vectastain ABC reagent (Vector Labs, PK-6100) for 30 min at RT. The sections were washed in 0.1% TBST for 5 min 3 times and developed with 3,3'-diaminobenzidine substrate. The reaction was monitored for 1-3 min, and then quenched by immersing the slides in $dH_2O$ as soon as the sections developed. Hematoxylin was added as a counterstain for about 20 seconds, and the sections were dehydrated in increasing concentrations of ethyl alcohol (70%, 80%, 95%, 95%, 100%, 100%). Coverslips were attached using Permount™ mounting medium (Fisher, Pittsburgh, PA, #SP15-100) in xylene. Serial sections were processed for histology (H&E). Controls were prepared using same method without primary anti-cMet antibody. Serial sections were processed for routine histology (H&E).

Immunofluorescence Staining of cMet with QQT*-Cy5.5/Antibody in CPC;Apc Mouse Colonic Adenoma and Human Proximal Colonic Neoplasia Specimens of mouse colonic adenoma were harvested, formalin-fixed, and paraffin-embedded. Specimens of tubular adenomas (n=21), sessile serrated adenomas (n=13), hyperplastic polyps (n=7), and normal colonic mucosa (n=10) from human proximal colon were obtained from the archived tissue bank in the University of Michigan Department of Pathology. Human specimens were treated as same as mouse colonic specimens. Sections (5-mm thick) were cut and mounted onto glass slides (Superfrost Plus; Fischer Scientific). Serial 5 m sections were deparaffinized, and antigen retrieval was performed as described above. The sections were blocked with 10% goat normal serum (Fisher Scientific, 50062Z) for 10 min at RT followed by rinsing with PBS. Sections were incubated with 5 μM QQT*-Cy5.5 with 2% BSA for 10 min at RT. The sections were then washed 3 times with 0.1% PBST and further incubated with a 1:200 dilution of anti-cMet primary antibody (Cell Signaling Technology, #8198) with 2% BSA for 2 hours at RT in the dark. Sections were washed 3 times with 0.1% PBST for 3 min each, and then incubated with 1:500 AF488-labeled goat anti rabbit secondary antibody (Abcam, ab150077) with 2% BSA for 1 hour at RT in the dark. After washing 3 times with 0.1% PBST for 3 min each, the sections were mounted with Prolong Gold reagent containing DAPI (Invitrogen). Adjacent sections were processed for histology (H&E). We placed 3 boxes with dimensions of $20 \times 20\ \mu m^2$ completely within colonic epithelium in each image, and measured the mean fluorescence intensities using custom Matlab software. Regions of saturated intensities were avoided.

Example 2

Peptide Specific for cMet

Figure 1:
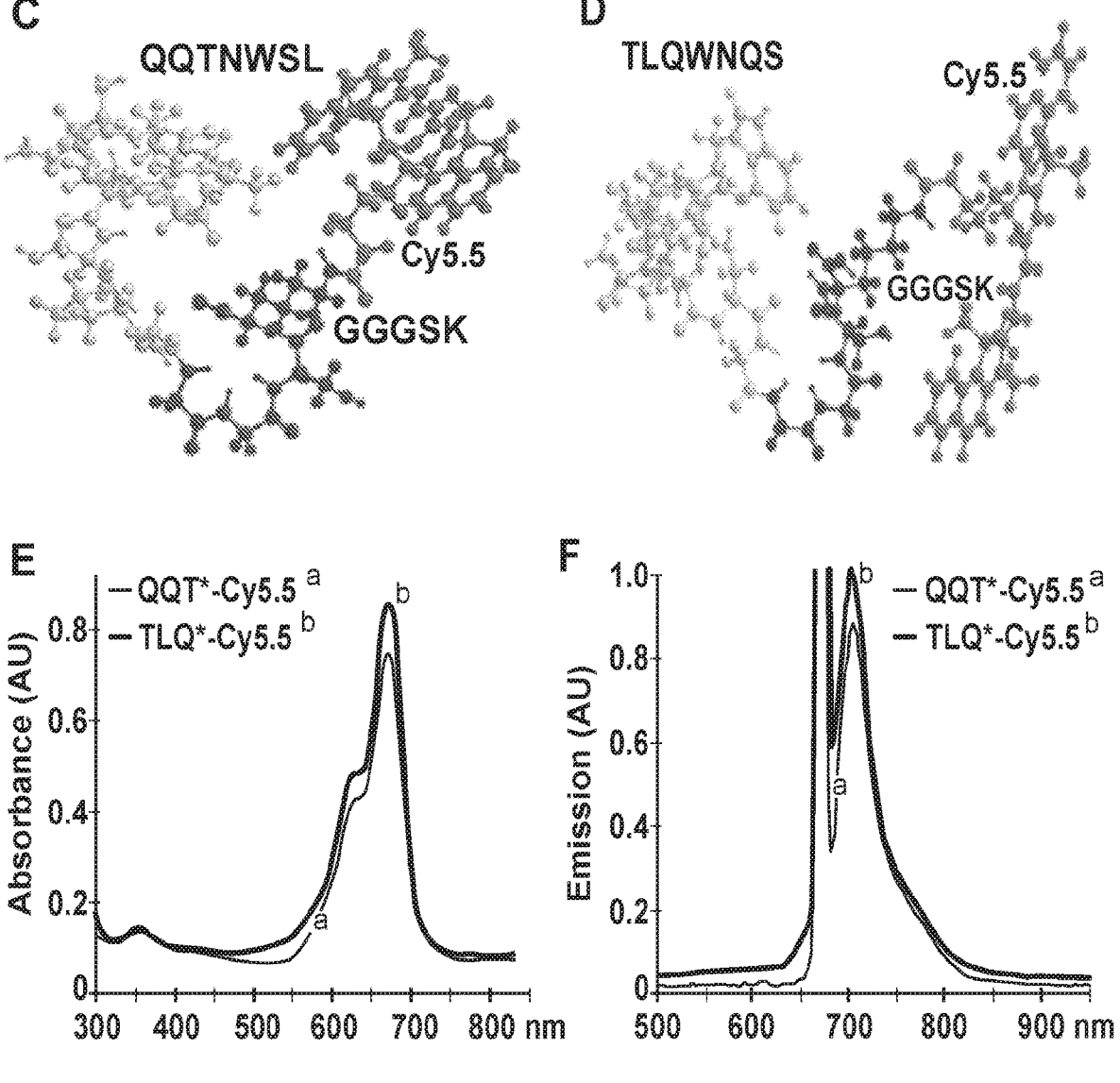
FIG. 1. Peptide specific for cMet. Biochemical structures are shown for A) the exemplary target peptide sequence QQTNWSL (SEQ ID NO:1), and B) the scrambled control peptide sequence TLQWNQS (SEQ ID NO:3). A GGGSK linker (SEQ ID NO:2) separates the Cy5.5 fluorophore from the amino acid sequence of a peptide being labeled to prevent steric hindrance. C and D) Three-dimensional mod-

The linear, heptapeptide sequence QQTNWSL (SEQ ID NO:1) was identified by biopanning a high diversity phage display library of linearized heptapeptides against the extracellular domain (ECD) of cMet. The peptide showed the lowest P-value for binding interactions using a structural model for cMet. The C-terminus of this peptide (black) is covalently linked with the fluorophore Cy5.5 (red) via a GGGSK linker (blue), hereafter QQT*-Cy5.5, FIG. 1A. The linker separates the peptide from the fluorophore to prevent steric hindrance. The scrambled sequence TLQWNQS (SEQ ID NO:3) is also labeled with Cy5.5 for use as control, hereafter TLQ*-Cy5.5, FIG. 1B. Three-dimensional models show differences in biochemical structures, FIG. 1C,D. Peak absorbance and emission of the Cy5.5-labeled peptides occur in the near-infrared (NIR) spectrum, FIG. 1E,F, where hemoglobin absorption, tissue scattering, and tissue autofluorescence are minimal. Tissue penetration depth is maximum, and hemoglobin absorption, tissue scattering, and tissue autofluorescence have the least effects in this regime. The peptides were synthesized with greater than 95% purity by HPLC, and an experimental mass-to-charge (m/z) ratio of 1827.67 was measured using mass spectrometry, which agrees with expected values, FIG. 9.

Example 3

Validation of Binding with Cells In Vitro siRNA knockdown experiments were performed using HT29 human colorectal cancer cells to validate specific binding of QQT*-Cy5.5 to cMet. On confocal microscopy, QQT*-Cy5.5 (red) and AF488-labeled anti-cMet antibody (green) bind strongly to the surface (arrows) of control HT29 cells transfected with siCL (control), FIG. 2A,B, while TLQ*-Cy5.5 shows minimal binding, FIG. 2C. Reduced fluorescence intensities were observed with HT29 knockdown cells (sicMet), FIG. 2D,E, and TLQ*-Cy5.5 showed little signal, FIG. 2F. Quantified results showed this decrease to be significant, FIG. 2G. Western blot showed the effect of cMet expression knockdown in the cells, FIG. 2H. Also, significantly greater fluorescence intensity was observed for binding of QQT*-Cy5.5 and anti-cMet-AF488 to HT29 cells (cMet+) compared with SW480 human colorectal cancer cells (cMet−) cells, FIG. 10. Similar results were found using mouse S114 (cMet+) and NIH3T3 (cMet−) cells, FIG. 11.

Example 4

Peptide Characterization

Specific binding of QQT*-Cy5.5 to cMet was confirmed by adding unlabeled QQT* to compete for binding. Fluorescence intensities were observed to decrease significantly in a concentration dependent manner, FIG. 3A. These results indicate that the peptide rather than either the linker or fluorophore mediates the binding interaction. By comparison, fluorescence intensities from binding of QQT*-Cy5.5 to HT29 cells did not change with addition of hepatocyte growth factor (HGF), a known ligand for cMet, at concentrations ranging from 0 to 100 ng/mL, FIG. 17A. A pull-down assay showed a strong band from QQT* binding to mouse cMet-ECD by comparison with that for TLQ*, FIG. 17B. Co-localization of binding by QQT*-Cy5.5 (red) and anti-cMet-AF488 (green) to the surface (arrows) of HT29 cells was observed on the merged image with a Pearson's correlation coefficient of $\rho = 0.73$, FIG. 3B. An apparent dissociation constant of $k_d = 57$ nM was measured for binding by QQT*-Cy5.5 to HT29 cells using flow cytometry, FIG. 3C, and an apparent association time constant of k=0.62 min$^{-1}$ (1.6 min) was measured for the same cells, supporting rapid binding with topical administration, FIG. 3D.

Example 5

Effect of Peptide on Cell Signaling

Hepatocyte growth factor (HGF) is a known ligand for cMet, and was incubated with HT29 cells (cMet+) as a positive control. Strong phosphorylation activity was observed for cMet (p-cMet), downstream AKT (p-AKT), and ERK1/2 (p-ERK1/2) on Western blot, FIG. 4. Addition of QQT* at a concentration of either 5 or 100 μM, however, resulted in no change in phosphorylation of any of these downstream markers of cell signaling.

More particularly, no competition was observed between QQT* and HGF, supporting a lack of interaction and effect on downstream signaling, FIG. 17A. These results indicate that the peptide and HGF bind to different sites on the cMet target. Western blots were performed to evaluate markers for activation of downstream cell signaling, FIG. 4A. Incubation of HGF (positive control) with HT29 cells showed strong phosphorylation activity for cMet (p-cMet), downstream AKT (p-AKT), and ERK1/2 (p-ERK1/2). By comparison, addition of QQT*-Cy5.5 at concentrations of 5 and 100 μM resulted in no change in phosphorylation of any substrate. An alamar blue assay showed no effect on growth of HT29 and CCD841 cells with addition of QQT*-Cy5.5 at concentrations of either 5 or 100 μM for 48 hours by comparison with HGF, FIG. 4B,C. CCD841 normal colon cells were used to evaluate the effect of the peptide on the cell phenotype in non-tumor cells.

Example 6

In Vivo Imaging of Genetically Engineered CRC Mice

The results of a pull-down assay supported specific binding of QQT*-Cy5.5 to mouse cMet-ECD, FIG. 17B. A rigid small animal endoscope was used to collect in vivo images in CPC;Apc mice. A white light image collected with that small animal endoscope showed no grossly visible polyps (arrow) in the colon of a CPC;Apc mouse, FIG. 12A. This mouse was genetically engineered to somatically delete an Apc allele under Cre regulation, and developed both flat and polyploid adenomas spontaneously. QQT*-Cy5.5 was then topically administered, allowed to incubate for about 5 min, and the unbound peptides were rinsed away. A NIR fluorescence image was collected after staining with QQT*-Cy5.5 showed the presence of a flat lesion (arrow), FIG. 12B. Reflectance images registered with fluorescence were acquired, FIG. 12C. The fluorescence image collected from the same lesion 3 days later using TLQ*-Cy5.5 (control) showed little signal, FIG. 12D. Similar results were obtained from a representative polyploid lesion, FIG. 5E-H. A ratio of fluorescence and reflectance images from the flat lesion was determined to correct for differences in distance and geometry over the image field-of-view (FOV) to allow for image intensities to be accurately quantified, FIG. 51. Fluorescence, reflectance, and ratio values from the dashed line in FIG. 51 were shown, FIG. 5J. Images collected from polyps were processed similarly. A white light image collected in a different mouse showed the presence of a polyp (arrow), FIG. 12E (see also, FIG. 14A). The fluorescence image collected showed strong intensity from the pre-malignant lesion (arrow), FIG. 12F. Reflectance images registered with fluorescence were acquired, FIG. 12G. Fluorescence image collected from the same polyp 3 days later with TLQ*-Cy5.5 showed minimal signal, FIG. 12H. The ratio of the fluorescence and reflectance images from the flat lesion in FIG. 12A was used to correct for differences in distance and geometry over the image field-of-view, and allowed for the image intensities to be accurately quantified, FIG. 12I. Fluorescence, reflectance, and ratio values from dashed lines in FIG. 12I were shown, FIG. 12J. The mean T:B ratio for QQT*-Cy5.5 was found to be significantly greater than the T:B ratio for TLQ*-Cy5.5 for polyps and flat lesions, FIGS. 12K and 14G. Histology (H&E) of the flat lesion and polyp was shown adjacent to normal colonic mucosa, and displayed features of low-grade dysplasia, FIG. 12L, M.

Example 7

Macroscopic Validation in Mouse Colon Ex Vivo

After imaging was completed, the CPC;Apc mice were euthanized, and the colon was excised and divided longitudinally to expose the mucosal surface for collection of macroscopic white light and fluorescence images, FIGS. 5 L,M and 13A, B. The polyp locations co-localized on white light and fluorescence images, FIG. 13C. In n=5 mice, significantly greater mean fluorescence intensities from dysplasia were found, compared with adjacent normal colonic mucosa in n=10 regions, FIG. 13D. Immunohistochemistry was performed with a known antibody to validate increased expression of cMet in mouse dysplasia, FIG. 13E, by comparison with normal colonic mucosa, FIG. 13F.

This ex vivo imaging validated the specific binding by QQT*-Cy5.5 to cMet. The colon was excised and divided longitudinally to expose the mucosal surface. Co-localization at the polyps was seen on the merged image, FIG. 5N. The adenoma borders were clearly seen. The mean fluorescence intensity was significantly greater for polyps versus adjacent normal colonic mucosa, FIG. 5O. Expression of cMet was increased in mouse adenoma versus normal colon using immunohistochemistry (IHC), FIG. 5P,Q.

Example 8

Microscopic Validation in Mouse Colon Ex Vivo

Increased fluorescence staining of QQT*-Cy5.5 and anti-cMet-AF488 on the surface of dysplastic colonocytes (arrow) was observed in sections of CPC;Apc mouse colon using confocal microscopy, FIG. 15A, B. The merged image showed co-localization of peptide and antibody binding (arrow) with a correlation of ρ=0.78, FIG. 15C. Minimal staining was observed for peptide and antibody binding to normal colonic mucosa, FIG. 15D-F. Quantified results showed significantly greater mean fluorescence intensity for dysplasia versus normal colonocytes, FIG. 15G. ROC curve showed 93% sensitivity and 87% specificity with an area under curve (AUC) of 0.96 for QQT*-Cy5.5, to distinguish dysplasia from normal tissue. Histology (H&E) for mouse adenoma and normal colon are shown, FIG. 15H,I.

Example 9

In Vivo Imaging of Patient-Derived Colonic Organoids

A white light image collected with a small animal endoscope showed the presence of two human normal (arrow, FIG. 19A) and one tubular adenoma organoids (arrow, FIG. 19E) implanted in the colon of immunocompromised mice. QQT*-Cy5.5 was then topically administered, allowed to incubate for about 5 min, and the unbound peptides were rinsed away. Fluorescence images showed minimal signal from the normal organoids (arrow, FIG. 19B) and strong intensity from the pre-malignant tubular adenoma organoid (arrow, FIG. 19F). Reflectance images registered with fluorescence were acquired (FIG. 19C, G). The fluorescence images collected from normal and adenoma organoids 3 days later using TLQ*-Cy5.5 (control) showed little signal (FIG. 19D, H). The statistical mean T:B ratio for QQT*-Cy5.5 in vivo on adenoma was found to be significantly greater than that on normal organoids, FIG. 19L. H&E histology staining of normal and adenoma organoids is shown in FIG. 19J, M. IHC staining of human specific hCytokeratin on the same slides demonstrated the successful transplantation of human organoids (FIG. 19K, N). Using these tissue sections, IF co-staining of cMet antibody and QQT*-Cy5.5 showed minimal signal to normal colon (FIG. 19K) while strong intensity to adenoma organoids (FIG. 19O), establishing that QQT*-Cy5.5 specifically bound to cMet-overexpressed human tissues. The statistical results are shown in FIG. 19P. Using tissue sections, QQT*-Cy5.5 showed strong staining to adenoma and minimal staining to normal crypts using immunofluorescence, FIG. 19I.

To investigate whether QQT*-Cy5.5 also bound to SSA, we generated an SSA transplanted mouse model using the same method. White light of normal and SSA organoids are shown in FIG. 16A, E (arrow). The fluorescence images collected from normal and SSA organoids are shown in FIG. 16B, F (arrow). QQT*-Cy5.5 showed significantly higher signal on SSA than normal organoids. Reflectance images registered with fluorescence were acquired (FIG. 16C, G). Fluorescence images were collected from these two types of organoids 3 days later using TLQ*-Cy5.5 (control), which showed minimal signal. The statistical mean T:B ratio for QQT*-Cy5.5 in vivo on SSA was found to be significantly greater than that on normal organoids, FIG. 19L. H&E histology staining of normal and SSA organoids is shown in FIG. 16I, M. IHC staining of human specific hCytokeratin on the same slides demonstrated the successful transplantation of human organoids (FIG. 16J, N). Using these tissue sections, IF co-staining of cMet antibody and QQT*-Cy5.5 showed minimal signal to normal colon (FIG. 19K) while strong intensity to SSA organoids (FIG. 16O). In conclusion, these in vivo imaging results showed that, compared to normal organoids, QQT*-Cy5.5 could specifically bind to adenoma and SSA human organoids that expressed cMet at high levels.

Example 10

Validation of cMet Expression in Human Colon

Staining of human colon with QQT*-Cy5.5 and anti-cMet-AF488 was evaluated in n=42 formalin-fixed, paraffin-embedded (FFPE) specimens of human colon, including tubular adenoma, sessile serrated adenoma (SSA), hyperplastic polyp (HP), and normal mucosa. Merged fluorescence images are shown for representative sections of adenoma, SSA, hyperplastic polyp (HP), and normal colonic mucosa, collected with confocal microscopy, FIG. 6A-D. Co-localization of peptide and antibody binding was strong for each histological classification. Immunofluorescence of SSA specimens showed large, dilated crypts with numerous goblet cells, indicative of abnormal maturation. Immuno-histochemistry was performed to validate cMet expression. Strong staining (2+/3+) was observed for adenoma and SSA, while weak staining (0+/1+) was seen for HP and normal, FIG. 6E-H. Representative histology (H&E) was shown, FIG. 6I-L. The mean fluorescence intensity from staining with QQT*-Cy5.5 was significantly greater for either adenoma or SSA versus either HP or normal colon, FIG. 6M. A total of n=11 SSA lesions were described endoscopically with a flat appearance, and n=2 were documented to be slightly protruding from colonoscopy reports. Representative histology (H&E) is shown for each histological classification, FIG. 6K-N.

REFERENCES

1. Favoriti, P., et al. Worldwide burden of colorectal cancer: a review. Updates Surg 68, 7-11(2016).
2. Torre, L. A., et al. Global cancer statistics, 2012. CA Cancer J Clin 65, 87-108 (2015).
3. Ferlay, J., et al. Estimates of worldwide burden of cancer in 2008: GLOBOCAN 2008. Int J Cancer 127, 2893-2917 (2010).
4. Ferlay, J., et al. Cancer incidence and mortality worldwide: sources, methods and major patterns in GLOBOCAN 2012. Int J Cancer 136, E359-386 (2015).
5. Brown, S. C., Abraham, J. S., Walsh, S. & Sykes, P. A. Risk factors and operative mortality in surgery for colorectal cancer. Ann R Coll Surg Engl 73, 269-272 (1991).
6. Carraro, P. G., Segala, M., Cesana, B. M. & Tiberio, G. Obstructing colonic cancer: failure and survival patterns over a ten-year follow-up after one-stage curative surgery. Dis Colon Rectum 44, 243-250 (2001).
7. Winawer, S. J., et al. Prevention of colorectal cancer by colonoscopic polypectomy. The National Polyp Study Workgroup. N Engl J Med 329, 1977-1981 (1993).
8. Winawer, S. J., et al. Randomized comparison of surveillance intervals after colonoscopic removal of newly diagnosed adenomatous polyps. The National Polyp Study Workgroup. N Engl J Med 328, 901-906 (1993).
9. Heresbach, D., et al. Miss rate for colorectal neoplastic polyps: a prospective multicenter study of back-to-back video colonoscopies. Endoscopy 40, 284-290 (2008).
10. Soetikno, R. M., et al. Prevalence of nonpolyploid (flat and depressed) colorectal neoplasms in asymptomatic and symptomatic adults. Jama 299, 1027-1035 (2008).
11. van Rijn, J. C., et al. Polyp miss rate determined by tandem colonoscopy: a systematic review. Am J Gastroenterol 101, 343-350 (2006).
12. Clapper, M. L., et al. Detection of colorectal adenomas using a bioactivatable probe specific for matrix metalloproteinase activity. Neoplasia 13, 685-691 (2011).
13. Marten, K., et al. Detection of dysplastic intestinal adenomas using enzyme-sensing molecular beacons in mice. Gastroenterology 122, 406-414 (2002).
14. Naran, S., Zhang, X. & Hughes, S. J. Inhibition of HGF/MET as therapy for malignancy. Expert Opin Ther Targets 13, 569-581 (2009).
15. Sattler, M. & Salgia, R. cMet and hepatocyte growth factor: potential as novel targets in cancer therapy. Curr Oncol Rep 9, 102-108 (2007).
16. Uehara, Y., et al. Placental defect and embryonic lethality in mice lacking hepatocyte growth factor/scatter factor. Nature 373, 702-705 (1995).
17. Christensen, J. G., Burrows, J. & Salgia, R. cMet as a target for human cancer and characterization of inhibitors for therapeutic intervention. Cancer Lett 225, 1-26 (2005).
18. Birchmeier, C., Birchmeier, W., Gherardi, E. & Vande Woude, G. F. Met, metastasis, motility and more. Nat Rev Mol Cell Biol 4, 915-925 (2003).
19. Maulik, G., et al. Role of the hepatocyte growth factor receptor, cMet, in oncogenesis and potential for therapeutic inhibition. Cytokine Growth Factor Rev 13, 41-59 (2002).
20. Di Renzo, M. F., et al. Overexpression and amplification of the met/HGF receptor gene during the progression of colorectal cancer. Clin Cancer Res 1, 147-154 (1995).
21. Fearon, E. R. & Vogelstein, B. A genetic model for colorectal tumorigenesis. Cell 61, 759-767 (1990).
22. Lu, R. M., Chang, Y. L., Chen, M. S. & Wu, H. C. Single chain anti-cMet antibody conjugated nanoparticles for in vivo tumor-targeted imaging and drug delivery. Biomaterials 32, 3265-3274 (2011).
23. Towner, R. A., et al. In vivo detection of cMet expression in a rat C6 glioma model. J Cell Mol Med 12, 174-186 (2008).
24. Joshi, B. P., et al. Design and Synthesis of Near-Infrared Peptide for in Vivo Molecular Imaging of HER2. Bioconjug Chem 27, 481-494 (2016).
25. Zhou, J., et al. EGFR Overexpressed in Colonic Neoplasia Can be Detected on Wide-Field Endoscopic Imaging. Clin Transl Gastroenterol 6, e101 (2015).
26. Burggraaf, J., et al. Detection of colorectal polyps in humans using an intravenously administered fluorescent peptide targeted against cMet. Nat Med 21, 955-961 (2015).
27. Sturm, M. B., et al. Targeted imaging of esophageal neoplasia with a fluorescently labeled peptide: first-in-human results. Sci Transl Med 5, 184ra161 (2013).
28. Hsiung, P. L., et al. Detection of colonic dysplasia in vivo using a targeted heptapeptide and confocal microendoscopy. Nat Med 14, 454-458 (2008).
29. Lee, S., Xie, J. & Chen, X. Peptides and peptide hormones for molecular imaging and disease diagnosis. Chem Rev 110, 3087-3111 (2010).
30. Sato, T., et al. Single Lgr5 stem cells build crypt-villus structures in vitro without a mesenchymal niche. Nature 459, 262-265 (2009).
31. Sugimoto, S., et al. Reconstruction of the Human Colon Epithelium In Vivo. Cell Stem Cell 22, 171-176 e175 (2018).
32. Li, M., et al. Affinity peptide for targeted detection of dysplasia in Barrett's esophagus. Gastroenterology 139, 1472-1480 (2010).
33. Fields, G. B. & Noble, R. L. Solid phase peptide synthesis utilizing 9-fluorenylmethoxycarbonyl amino acids. Int J Pept Protein Res 35, 161-214 (1990).
34. Thomas, R., et al. In vitro binding evaluation of 177Lu-AMBA, a novel 177Lu-labeled GRP-R agonist for systemic radiotherapy in human tissues. Clin Exp Metastasis 26, 105-119 (2009).
35. Joshi, B. P., Liu, Z., Elahi, S. F., Appelman, H. D. & Wang, T. D. Near-infrared-labeled peptide multimer functions as phage mimic for high affinity, specific targeting of colonic adenomas in vivo (with videos). Gastrointest Endosc 76, 1197-1206 e1191-1195 (2012).
36. Dame, M. K., et al. Identification, isolation and characterization of human LGR5-positive colon adenoma cells. Development 145(2018).

37. Sato, T., et al. Long-term expansion of epithelial organoids from human colon, adenoma, adenocarcinoma, and Barrett's epithelium. Gastroenterology 141, 1762-1772 (2011).

38. Tsai, Y. H., et al. A Method for Cryogenic Preservation of Human Biopsy Specimens and Subsequent Organoid Culture. Cell Mol Gastroenterol Hepatol 6, 218-222 e217 (2018).

39. Miyoshi, H. & Stappenbeck, T. S. In vitro expansion and genetic modification of gastrointestinal stem cells in spheroid culture. Nat Protoc 8, 2471-2482 (2013).

40. Shultz, L. D., et al. Human lymphoid and myeloid cell development in NOD/LtSz-scid IL2R gamma null mice engrafted with mobilized human hemopoietic stem cells. J Immunol 174, 6477-6489 (2005).

41. Ishikawa, F., et al. Development of functional human blood and immune systems in NOD/SCID/IL2 receptor {gamma} chain(null) mice. Blood 106, 1565-1573 (2005).

42. Yui, S., et al. Functional engraftment of colon epithelium expanded in vitro from a single adult Lgr5(+) stem cell. Nat Med 18, 618-623 (2012).

43. Xue, X., et al. Iron Uptake via DMT1 Integrates Cell Cycle with JAK-STAT3 Signaling to Promote Colorectal Tumorigenesis. Cell Metab 24, 447-461 (2016).

44. Hinoi, T., et al. Mouse model of colonic adenoma-carcinoma progression based on somatic Apc inactivation. Cancer Res 67, 9721-9730 (2007).

45. Liu, Z., Miller, S. J., Joshi, B. P. & Wang, T. D. In vivo targeting of colonic dysplasia on fluorescence endoscopy with near-infrared octapeptide. Gut 62, 395-403 (2013).

46. Joshi, B. P., et al. Detection of Sessile Serrated Adenomas in the Proximal Colon Using Wide-Field Fluorescence Endoscopy. Gastroenterology 152, 1002-1013 e1009 (2017).

47. Rex, D. K. Reducing costs of colon polyp management. Lancet Oncol 10, 1135-1136 (2009).

48. Hay, R. V., et al. Nuclear imaging of Met-expressing human and canine cancer xenografts with radiolabeled monoclonal antibodies (MetSeek). Clin Cancer Res 11, 7064s-7069s (2005).

49. Jagoda, E. M., et al. Immuno-PET of the hepatocyte growth factor receptor Met using the 1-armed antibody onartuzumab. J Nucl Med 53, 1592-1600 (2012).

50. Chen, K. & Chen, X. Design and development of molecular imaging probes. Curr Top Med Chem 10, 1227-1236 (2010).

51. Song, E. K., et al. Potent antitumor activity of cabozantinib, a cMet and VEGFR2 inhibitor, in a colorectal cancer patient-derived tumor explant model. Int J Cancer 136, 1967-1975 (2015).

52. Matsumura, A., et al. HGF regulates VEGF expression via the cMet receptor downstream pathways, PI3K/Akt, MAPK and STAT3, in CT26 murine cells. Int J Oncol 42, 535-542 (2013).

53. Bardelli, A., et al. Amplification of the MET receptor drives resistance to anti-EGFR therapies in colorectal cancer. Cancer Discov 3, 658-673 (2013).

54. Boccaccio, C., Luraghi, P. & Comoglio, P. M. MET-mediated resistance to EGFR inhibitors: an old liaison rooted in colorectal cancer stem cells. Cancer Res 74, 3647-3651 (2014).

55. Chen, J., et al. Multiplexed Targeting of Barrett's Neoplasia with a Heterobivalent Ligand: Imaging Study on Mouse Xenograft in Vivo and Human Specimens ex Vivo. J Med Chem 61, 5323-5331 (2018).

56. Su et al., Science 256(5057):668-670 (1992).

57. Hinoi et al., Cancer Res., 67(20): 9721-9730 (2007).

58. Alencar et al., Radiology, 244: 232-238 (2007).

59. Hung et al., Proc. Natl. Acad. Sci. USA, 107: 1565-1570 (2010).

60. Li et al., Gastroenterology, 139:1472-80 (2010).

61. Hsiung et al., Nat. Med., 14: 454-458 (2008).

62. Joyce et al., Cancer Cell, 4: 393-403 (2003).

63. Essler et al., Proc. Natl. Acad. Sci. USA, 99: 2252-2257 (2002).

64. Lee et al., Mol. Cancer Res., 5(1): 11-19 (2007).

65. Ludtke et al., Drug Deliv., 14: 357-369 (2007).

All publications and patents mentioned in the application are herein incorporated by reference in their entireties or in relevant part, as would be apparent from context. Various modifications and variations of the disclosed subject matter will be apparent to those skilled in the art without departing from the scope and spirit of the disclosure. Although the disclosure has been described in connection with specific embodiments, it should be understood that the invention as claimed should not be unduly limited to such specific embodiments. Various modifications of the described modes for making or using the disclosed subject matter that are obvious to those skilled in the relevant field(s) are intended to be within the scope of the following claims.

What is claimed is:

1. A peptide consisting of the amino acid sequence QQTNWSL set forth in SEQ ID NO:1.

\*    \*    \*    \*    \*